(12) United States Patent
Kaumaya

(10) Patent No.: US 8,470,333 B2
(45) Date of Patent: *Jun. 25, 2013

(54) CHIMERIC PEPTIDES COMPRISING HER-2 B-CELL EPITOPES AND T-HELPER EPITOPES

(75) Inventor: Pravin Kaumaya, Westerville, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/697,578

(22) Filed: Feb. 1, 2010

(65) Prior Publication Data

US 2011/0086055 A1 Apr. 14, 2011

Related U.S. Application Data

(63) Continuation of application No. 11/424,526, filed on Jun. 15, 2006, now Pat. No. 7,691,396.

(60) Provisional application No. 60/690,574, filed on Jun. 15, 2005.

(51) Int. Cl.
*A61K 39/00* (2006.01)

(52) U.S. Cl.
USPC ............ 424/192.1; 424/185.1; 424/194.1; 514/2; 530/300

(58) Field of Classification Search
None
See application file for complete search history.

(56) References Cited

U.S. PATENT DOCUMENTS

| | | | |
|---|---|---|---|
| 5,601,989 A | 2/1997 | Cheever et al. | 435/7.23 |
| 5,726,023 A | 3/1998 | Cheever et al. | 435/7.1 |
| 5,773,230 A | 6/1998 | Cheever et al. | 435/7.23 |
| 5,801,005 A | 9/1998 | Cheever et al. | 435/7.024 |
| 5,840,525 A | 11/1998 | Vandlen et al. | 435/69.1 |
| 5,846,538 A | 12/1998 | Cheever et al. | 424/185.1 |
| 5,869,445 A | 2/1999 | Cheever et al. | 514/2 |
| 5,876,712 A | 3/1999 | Cheever et al. | 424/93.7 |
| 6,015,567 A | 1/2000 | Hudziak et al. | 424/277.1 |
| 6,075,122 A | 6/2000 | Cheever et al. | 530/350 |
| 6,165,464 A | 12/2000 | Hudziak et al. | 424/131.1 |
| 6,339,139 B1 | 1/2002 | Gu et al. | 530/300 |
| 7,060,284 B1 | 6/2006 | Kaumaya et al. | 424/277.1 |
| 7,666,430 B2 | 2/2010 | Kaumaya et al. | 424/185.1 |
| 7,691,396 B2 | 4/2010 | Kaumaya et al. | 424/277.1 |
| 7,892,549 B2 | 2/2011 | Paton et al. | 424/143.1 |
| 8,080,253 B2 | 12/2011 | Kaumaya et al. | 424/192.1 |
| 8,110,657 B2 | 2/2012 | Kaumaya | |
| 2003/0170235 A1 | 9/2003 | Cohen et al. | 424/193.1 |
| 2003/0235594 A1 | 12/2003 | Humphreys et al. | 424/192.1 |
| 2006/0110400 A1 | 5/2006 | Glover et al. | 424/185.1 |
| 2006/0188976 A1 | 8/2006 | Takeshita et al. | 435/183 |
| 2010/0234283 A1 | 9/2010 | Kaumaya et al. | |
| 2012/0121626 A1 | 5/2012 | Kaumaya et al. | |
| 2012/0201841 A1 | 8/2012 | Kaumaya et al. | |

FOREIGN PATENT DOCUMENTS

| | | |
|---|---|---|
| AU | 2005213457 | 2/2005 |
| AU | 2006261342 | 6/2005 |
| AU | 2006261342 | 6/2006 |
| CA | 2555274 | 2/2005 |
| CA | 2612394 | 6/2005 |
| CA | 2612394 | 6/2006 |
| EP | 00953823.2 | 8/2000 |
| EP | 05722777.9 | 2/2005 |
| EP | 06785065.1 | 6/2005 |
| EP | 06785065.1 | 6/2006 |
| EP | 12170985.1 | 6/2012 |
| JP | 2001-513369 | 8/2000 |
| JP | 2003520781 | 7/2003 |
| JP | 2004522412 | 7/2004 |
| JP | 2008-517193 | 6/2005 |
| JP | 2012-93680 | 6/2005 |
| JP | 2008-517193 | 6/2006 |
| JP | 2012-93680 | 4/2012 |
| NZ | 564951 | 6/2005 |
| NZ | 564951 | 6/2006 |
| WO | WO 94/00153 | 1/1994 |
| WO | WO 94/07530 | 4/1994 |
| WO | WO 94/07531 | 4/1994 |
| WO | WO 95/17210 | 6/1995 |
| WO | WO 96/02555 | 2/1996 |
| WO | WO 96/33739 | 10/1996 |
| WO | WO 96/34888 | 11/1996 |
| WO | WO 97/38011 | 10/1997 |
| WO | WO 98/17797 | 4/1998 |
| WO | WO 99/31140 | 6/1999 |
| WO | WO 00/34337 | 6/2000 |
| WO | WO 01/08636 | 2/2001 |
| WO | WO 01/21193 | 3/2001 |
| WO | WO 02/14503 | 2/2002 |
| WO | PCT/US2000/021222 | 8/2003 |
| WO | WO 2004/030616 | 4/2004 |
| WO | WO 2004/078907 | 9/2004 |
| WO | WO 2004/113380 | 12/2004 |
| WO | PCT/US2005/003747 | 2/2005 |
| WO | WO 2005/039616 | 5/2005 |
| WO | PCT/US2006/023672 | 6/2005 |
| WO | WO 2005/076972 | 8/2005 |
| WO | WO 2006/138675 | 6/2006 |
| WO | WO 2006/138675 | 12/2006 |

OTHER PUBLICATIONS

Dakappagari et al (J Biological Chemistry, Jan. 2005, 280:54-63).*
U.S. Appl. No. 60/690,574, filed Jun. 15, 2005, Pravin T.P. Kaumaya.
U.S. Appl. No. 60/146,869, filed Aug. 3, 1999, Pravin T.P. Kaumaya.
U.S. Appl. No. 13/366,546, filed Feb. 6, 2012, Pravin T.P. Kaumaya.
U.S. Appl. No. 13/331,891, filed Dec. 20, 2012, Pravin T.P. Kaumaya.
U.S. Appl. No. 61/149,959, filed Feb. 4, 2009, Pravin T.P. Kaumaya.
U.S. Appl. No. 12/700,388, Feb. 4, 2010, Pravin T.P. Kaumaya.
U.S. Appl. No. 13/662,024, filed Oct. 26, 2012, Pravin T.P. Kaumaya.
Abe, Y. et al., Disulfide bond structure of humanepidermal growth factor receptor. J Biol Chem, 1998. 273(18): p. 11150-7.
Agus, D.B. et al., Phase I Clinical Study of Pertuzumab, a Novel HER Dimerization Inhibitor, in Patients With Advanced Cancer. J Clin Oncol, 2005. 23(11): p. 2534-43.
Agus, D.B. et al., Targeting ligand-activated ErbB2 signaling inhibits breast and prostate tumor growth. Cancer Cell, 2002. 2(2): p. 127-37.
Allred, D.C. et al., Overexpression of HER-2/neu and its relationship with other prognostic factors change during the progression of in situ to invasive breast cancer. Hum Pathol, 1992. 23(9): p. 974-9.

(Continued)

Primary Examiner — Laura B Goddard
(74) Attorney, Agent, or Firm — Ballard Spahr LLP

(57) ABSTRACT

Compositions, methods, and vaccines that may stimulate the immune system and that may be used for treating malignancies associated with overexpression of the HER-2 protein are provided. Such compositions include epitopes of the HER-2 proteins.

20 Claims, 22 Drawing Sheets

OTHER PUBLICATIONS

Amici, A. et al, DNA vaccination with full-length or truncated neu induces protective immunity against the development of spontaneous mammary tumors in HER-2/neu transgenic mice. Gene Ther, 2000. 7(8): p. 703-6.

Amici, A. et al, Genetic immunization against neulerbB2 transgenic breast cancer. Cancer Immunol Immunother, 1998. 47(4): p. 183-90.

Baselga, J., et al., Phase II study of weekly intravenous recombinant humanized anti-p185HER2 monoclonal antibody in patients with HER2/neu-overexpressing metastatic breast cancer. J. Clin. Oncol. 14:737-44, 1996.

Baxevanis, C.N. et al., Tumor-specific CD4+ T lymphocytes from cancer patients are required for optimal induction of cytotoxic T cells against the autologous tumor. J Immunol, 2000. 164(7): p. 3902-12.

Bennasroune, A. et al., Transmembrane Peptides as Inhibitors of ErbB Receptor Signaling. Mol. Bioi. Cell, 2004. 15(7): p. 3464-3474.

Berchuck, A. et al., Overexpression of HER-2/neu is associated with poor survival in advanced epithelial ovarian cancer. Cancer Res, 1990. 50(13): p. 4087-91.

Berezov, A. et al., Disabling receptor ensembles with rationally designed interface peptidomimetics. J Bioi Chem, 2002. 277(31): p. 28330-9.

Berezov, A. et at., Structure-based approaches to inhibition of erbB receptors with peptide mimetics. Immunol Res, 2003. 27(2-3): p. 303-8.

Bernards, R., et al., Effective tumor immunotherapy directed against an oncogene-encoded product using a vaccinia virus vector. Proc. Natl. Acad. Sci. USA, 84:6854-8, 1987.

Binetruy-Toumaire, R. et al., Identification of a peptide blocking vascular endothelial growth factor (VEGF)-mediated angiogenesis. Embo J, 2000. 19(7): p. 1525-33.

Boggio, K. et al., Ability of systemic interleukin-12 to hamper progressive stages of mammary carcinogenesis in HER2/neu transgenic mice. Cancer Res, 2000. 60(2): p. 359-64.

Boggio, K. et al., Interleukin 12-mediated prevention of spontaneous mammary adenocarcinomas in two lines of Her-2/neu transgenic mice. J Exp Med, 1998. 188(3): p. 589-96.

Boocock et al., Expression of vascular endothelial growth factor and its receptors fit and KDR in ovarian carcinoma. J. Natl. Cancer Inst., 1995. 87: p. 506-516.

Bowie, J.U. et al., Deciphering the message in protein sequences: Tolerance to amino acid substitutions. Science, 1990. 247: p. 1306-1309.

Carmeliet, P. et al., Angiogenesis in cancer and other diseases. Nature, 2000. 407(6801): p. 249-57.

Cefai, D. et al., Targeting HER-2/neu for active-specific immunotherapy in a mouse model of spontaneous breast cancer. Int J Cancer, 1999. 83(3): p. 393-400.

Chang, S.Y. et al., Enhanced efficacy of DNS vaccination against Her-2/neu tumor antigen by genetic adjuvants. Int J Cancer, 2004. 111 (1): p. 86-95.

Chen et al., Monoclonal antibodies against vascular endothelial growth factor165 ($VEGF_{165}$): Neutralization of biological activity Biochemistry and recognition of the epitope and. Biochemistry and Molecular Biology International, 1999. 47(2): p. 161-169.

Cho, H.S. et al., Structure of the extracellular region of HER2 alone and in complex with the Herceptin Fa b. Nature, 2003. 421(6924): p. 756-60.

Chorev, M. et al., Recent developments in retro peptides and proteins-an ongoing topochemical exploration. Trends Biotechnol, 1995. 13(10): p. 438-45.

Chou et al., Prediction of the secondary structure of proteins from their amino acid sequence. Adv Enzymol Relat Subj Biochem, 1978. 47: p. 45-148.

Choudhury, A. et al., Small interfering RNA (siRNA) inhibits the expression of the Her2/neu gene, upregulates HLA class I and induces apoptosis of Her2/neu positive tumor eel/lines. Int J Cancer, 2004. 108(1): p. 71-7.

Cifaldi, L. et al., A light, nontoxic interleukin 17 protocol inhibits HER-2/neu mammary carcinogenesis in BALB/c transgenic mice with established hyperplasia. Cancer Res, 2001. 61(7): p. 2809-12.

Clynes, R.A. et al., Inhibitory Fc receptors modulate in vivo cytoxicity against tumor targets [see comments]. Nature Medicine, 2000. 6(4): p. 443-6.

Cobleigh, M.A. et al., A phase III dose-escalation trial of bevacizumab in previously treated metastatic breast cancer. Semin Oncol, 2003. 30(5 Suppl16): p. 117-24.

Cole et al., The EBV-Hybridoma Technique and its application to human lung cancer. Monoclonal Antibodies and Cancer Therapy, 1985. p. 77-96.

Cuadros, C. et al., Cooperative effect between immunotherapy and antiangiogenic therapy leads to effective tumor rejection in tolerant Her-2/neumice. Cancer Res, 2003. 63(18): p. 5895-901.

Dakappagari, NK et al,, Peptide Vaccine Strategies for Immunotherapy of HER-2/NEU Overexpressing Cancers, Americanc Peptide Symposium, 1999. Abstract P752.

Dakappagari, N.K. et al., Prevention of mammary tumors with a chimeric HER-2 B-cell epitope peptide vaccine. Cancer Res, 2000. 60(14): p. 3782-9.

Dakappagari, N.K. et al., Evalution of Chimeric B-Cell Epitope of HER-2: Application to Cancer Patients. Dissertation at Ohio State University, 2001.

Dakappagari, N.K. et al., Evaluation of synergistic interaction between cytokines and peptide epitope vaccines in protection against HER-2 expressing lung metastases. American Peptide Symposium, 2001. Abstract P1012.

Dakappagari, N.K. et al., A chimeric multi-human epidermal growth factor receptor-2 B cell epitope peptide vaccine mediates superior anti-tumor responses. J Immunol, 2003. 170(8): p. 4242-53.

Dakappagari, N.K. et al., Conformational HER-2/neu. B-cell Epitope Peptide Vaccine Designed to Incorporate Two Native Disulfide Bonds Enhances Tumor Cell Binding and Antitumor Activities. J Bioi Chern, 2005. 280(1): p. 54-63.

Dakappagari, N.K. et al., Intracellular delivery of a novel multiepitope peptide vaccine by an amphipathic peptide carrier enhances cytotoxic T-cell responses in HLA-A *201 mice. J Pept Res, 2005. 65(2): p. 189-99.

Dankert, D. et al., Grb2 and Shc adapter proteins play distinct roles in Neu (ErbB-2)-induced mammary tumorigenesis: implications for human breast cancer. Mol Cell Bioi, 2001. 21 (5): p. 1540-51.

De Giovanni, C. et al., Inununoprevention of HER-2/neu transgenic mammary carcinoma through an interleukin 12-engineered allogeneic cell vaccine. Cancer Res, 2004. 64(11): p. 4001-9.

De Groot et at., Developing an epitope-driven tuberculosis (TB) vaccine. J Vaccine, 2005. 23(17-18): p. 2121-31.

De Lorenzo, C. et at., A fully human antitumor immunoRNase selective for ErbB-2-positive carcinomas. Cancer Res, 2004. 64(14): p. 4870-4.

DelaCruz, J.S. et al., Protein vaccination with the HER2/neu extracellular domain plus anti-HER2/neu antibody-cytokine fusion proteins induces a protective anti-HER2/neu immune response in mice. Vaccine, 2003. 21(13-14): p. 1317-26.

Deulofeut et al., Cellular recognition and HLA restriction of a midsequence HBsAg peptide in hepatitis B vaccinated individuals. Mol. Immunol, 1993. 30: p. 941-948.

DiCarlo, E. et al., Analysis of mammary carcinoma onset and progression in HER-2/neu oncogene transgenic mice reveals a lobular origin. Lab Invest, 1999. 79(10): p. 1261-9.

Disis, M.L. et al., Existent T-cell and antibody immunity to HER-2/neu protein in patients with breast cancer. Cancer Res, 1994. 54(1): p. 16-20.

Disis, M.L. et al., Immunization of oncogenic HER-s/neu protein with peptide based vaccines. Proceedings of the Annual Meeting of the American Association for Cancer Research, 1995. 36: p. 251.

Disis, M.L. et al., Peptide-based, but not whole protein, vaccines elicit immunity to HER-2/neu, oncogenic self-protein. J Immunol, 1996. 156(9): p. 3151-8.

Disis, M.L. et al,, Granulocyte-Macrophage colony stimulating factor: An effective adjuvant for protein and peptide-based vaccines. Blood, 1996. 88(1): p. 202-210.

Disis, M.L. et al., Generation of immunity to the HER-2/neuoncogenic protein in patients with breast and ovarian cancer using a peptide-based vaccine. Clin Cancer Res, 1999. 5(6): p. 1289-97.

Disis, M.L. et al., High-titer HER-2/neu protein-specific antibody can be detected in patients with early-stage breast cancer. J Clin Oncol, 1997. 15(11): p. 3363-7.

Drebin, J.A. et al., Inhibition of tumor growth by monoclonal antibody reactive with an oncogene-encoded tumor antigen. Proc Natl Acad Sci, 1986. 83: p. 9129-9133.

Drebin, J.A. et al., Monoclonal antibodies reactive with distinct domains of the neu oncogene-encoded p185 molecule exert synergistic anti-tumor effects in vivo. Oncogene, 1988. 2(3): p. 273-7.

Drebin, J.A. et al., Monoclonal antibodies specific for the neu oncogene product directly mediate anti-tumor effects in vivo. Oncogene, 1988. 2(4): p. 387-394.

El-Mousawi, M. et al., Alakhov, A vascular endothelial growth factor high affinity receptor 1-specific peptide with antiangiogenic activity identified using a phage display peptide library. J Bioi Chem, 2003. 278(47): p. 46681-91.

Esserman, L. J. et al., Vaccination with the extracellular domain p185neu prevents mammary tumor development in neu transgenic mice. Cancer Immunol. Immunother., 1999. 47:337-42.

Fairbrother, W.J. et al., Novel peptides selected to bind vascular endothelial growth factor target the receptor-binding site. Biochemistry, 1998. 37(51): p. 17754-64.

Fendly, B.M. et al., Characterization of murine monoclonal antibodies reactive to either the human epidermal growth factor receptor or HER21neu gene product. Cancer Res, 1990. 50(5): p. 1550-8.

Ferrara, N. et al., Pituitary follicular cells secrete a novel heparin-binding growth factor specific for vascular endothelial cells. Biochem Biophys Res Commun, 1989. 161(2): p. 851-8.

Ferrara, N. et al., Discovery and development of bevacizumab, an anti-VEGF antibody for treating cancer. Nat Rev Drug Discov, 2004. 3(5): p. 391-400.

Ferrara, N., Vascular endothelial growth factor as a target for anticancer therapy. Oncologist, 2004. 9 Suppl1: p. 2-10.

Ferrara, N., Vascular endothelial growth factor: basic science and clinical progress. Endocr Rev, 2004. 25(4): p. 581-611.

Ferrara, N., Vascular endothelial growth factor and age-related macular degeneration: from basic science to therapy. Nature Medicine, 2010. 16(10): p. 1107-1111.

Fisk, B. et al., Existent proliferative responses of peripheral blood mononuclear cells from healthy donors and ovarian cancer patients to HER-2 peptides. Anticancer Res, 1997. 17(1A): p. 45-53.

Fisk, B. et al., Identification of an immunodominant peptide of HER-2/neu protooncogene recognized by ovarian tumor-specific cytotoxic T lymphocyte lines. J Exp Med, 1995. 181(6): p. 2109-17.

Franovic, A. et al., Human cancers converge at the HIF-2α oncogenic axis. Proc. Natl. Acad. Sci., 2009. 106(50): 21306-21311.

Frangione-Beebe et al., Enhanced immunogenicity of a conformational epitope of human T-lymphotropic virus type 1 using a novel chimeric peptide. Vaccine, 2001. 19: p. 1068-1081.

Franklin, M.C. et al., Insights into ErbB signaling from the structure of the ErbB2-pertuzumab complex. Cancer Cell, 2004. 5(4): p. 317-28.

Gan, Y.H. et al., Antitumour immunity of Bacillus CalmetteGuerin and interferon alpha in murine bladder cancer. European Journal of Cancer, 1999. 35(7): p. 1123-9.

Garrett, T.P. et al., Crystal structure of a truncated epidermal growth factor receptor extracellular domain bound to transforming growth factor alpha. Cell, 2002. 110(6): p. 763-73.

Garrett, T.P. et al., The crystal structure of a truncated ErbB2 ectodomain reveals an active conformation, poised to interact with other ErbB receptors. Mol Cell, 2003. 11 (2): p. 495-505.

GenBank Accession No. P04626, NCBI, p. 1-23.

Gentz et al., Bioassay for trans-activation using purified human immunodeficiency virus tat-encoded protein: Trans-activation requires mRNA synthesis. Proc Natl Acad Sci, 1989. 86: p. 821-824.

Goodman, M. et al., Topochemical design of bioactive peptides and peptidomimetics. Bioorg Khim, 1992. 18(10-11): p. 1375-93.

Gordon et al., Phase I safety and pharmacokinetic study of recombinant human anti-vascular endothelial growth factor in patients wit advanced cancer. J Clin Oncol, 2001. 19: p. 843-850.

Gu, X. G., et al., A novel hydrophobized polysaccharide/oncoprotein complex vaccine induces in vitro and in vivo cellular and humoral immune responses against HER-2-expressing murine sarcomas. Cancer Res., 58: 3385-90, 1998.

Guy, C.T. et al., Expression of the neu protooncogene in the mammary epithelium of transgenic mice induces metastatic disease. Proc Natl Acad Sci U S A, 1992. 89(22): p. 1 0578-82.

Hanahan et al., Patterns and emerging mechanisms of the angiogenic switch during tumorogenesis. Cell, 1996. 86: p. 853-864.

Harwerth, I.M. et al., Monoclonal antibodies directed to the erbB-2 receptor inhibit in vivo tumour cell growth. Br J Cancer, 1993. 68(6): p. 1140-5.

Hennighausen, L. et al., Mouse models for breast cancer. Oncogene, 2000. 19(8): p. 966-7.

Heroult, M. et al., Heparin affin regulatory peptide binds to vascular endothelial growth factor (VEGF) and inhibits VEGF-induced angiogenesis. Oncogene, 2004. 23(9): p. 17 45-53.

Herrera et al., Antigenicity and immunogenicity of multiple antigen peptides (MAP) containing P. vivax CS epitopes in Aotus monkeys. Parasite Immunology, 1997. 19: p. 161-170.

Hetian, L. et al., A novel peptide isolated from a phage display library inhibits tumor growth and metastasis by blocking the binding of vascular endothelial growth factor to its kinase domain receptor. J Bioi Chem, 2002. 277(45): p. 43137-42.

Hoeben, A. et al., Vascular endothelial growth factor and angiogenesis. Pharmacol Rev, 2004. 56(4): p. 549-80.

Holash, J. et al., VEGF-Trap: a VEGF blocker with potent antitumor effects. Proc Natl. Acad Sci U S A, 2002. 99(17): p. 11393-8.

Hollingsworth et al., Tumor angiogenesis in advanced stage ovarian carcinoma. Am J Pathol, 1995. 147: p. 33-41.

Hopp et al., Prediction of protein antigenic determinants from amino acid sequences. Proc Nati Acad Sci, 1981. 78: p. 3824-3828.

Houck, K.A. et al, The vascular endothelial growth factor family: identification of a fourth molecular species and characterization of alternative splicing of RNA. Mol Endocrinol, 1991. 5(12): p. 1806-14.

Hudziak, R.M. et al., p185H ER2 monoclonal antibody has anti proliferative effects in vitro and sensitizes human breast tumor cells to tumor necrosis factor. Mol Cell Bioi, 1989. 9(3): p. 1165-72.

Hynes, N.E. et al., The biology of erbB-2/neu/HER-2 and its role in cancer. Biochim Biophys Acta, 1994. 1198(2-3): p. 165-84.

Izumi, Y. et al., Tumour biology: herceptin acts as an antiangiogenic cocktail. Nature, 2002. 416(6878): p. 279-80.

Jain, R.K., Tumor angiogenesis and accessibility: role of vascular endothelial growth factor. Semin Oncol, 2002. 29(6 Suppl 16): p. 3-9.

Jasinska, J. et al., Inhibition of tumor cell growth by antibodies induced after vaccination with peptides derived from the extracellular domain of Her-2/neu. Int J Cancer, 2003. 107(6): p. 976-83.

Jemal et al., Cancer Statistics, 2003. CA Cancer J Clin, 2003. 53: p. 5-26.

Jiang et al., The immunogenicity of peptide versus DNA vaccine of an HER-2 CTL Epitope for breast and ovarian cancers. American Peptide Symposium, 1999. Abstract P751.

Jiang et al., Evaluation of the immunogenicity of peptide and DNA constructs for HER-2/neu epitopes. Peptides for the New Millennium (Editors: Fields, GB, Tam, TP and Batany), Kluwer Acadmeic Publisher, 2000. p. 695-696.

Jiang, B. et al., A Novel Peptide Isolated from a Phage Display Peptide Library with Trastuzumab Can Mimic Antigen Epitope of HER-2. J Bioi Chem, 2005. 280(6): p. 4656-62.

Karplus et al., Prediction of chain flexibility in proteins, a tool for the selection of peptide antigens. Naturwiss, 1985. 72: p. 212-213.

Kasprzyk, P.G. et al., Therapy of an animal model of human gastric cancer using a combination of anti-erbB-2 monoclonal antibodies. Cancer Research, 1992. 52(10): p. 2771-6.

Kaumaya et al., Synthesis and biophysical characterization of engineered topographic immunogenic determinants with aa topology. Biochemistry, 1990. 29: p. 13-23.

Kaumaya et al., Peptide Vaccines incorporating a "promiscuous" T-cell epitope bypass certain halotype restricted immune responses and provide broad spectrum immunogenicity. Journal of Molecular Recognition, 1993. 6: p. 81-94.

Kaumaya, P.T.P. et al., Denovo Engineering of Protein Immunogenic & Antigenic Determinants., in PEPTIDES, G.M.B. Anantharamaiah, C., Editor. 1994, Springer-Verlag. p. 133-164.

Kaumaya et al., "Synthetic Peptides: Dream or Reality." Published in Peptides in Immunology, Wiley and Sons, Ltd. (1996).

Kaumaya et al., A combination of HER-2 peptide epitope vaccines mediate superior biological effects. American Peptide Symposium, 2001. Abstract P1004.

Kaumaya et al., HER-2/neu cancer vaccines: Present status and Future. International Journal of Peptide Research and Therapeutics, 2006. 12(1): p. 65-77.

Kawashima et al., Identification of HLA-A3-restricted cytotoxic T lymphocyte epitopes from Carcinoembryonic Antigen and HER-2/neu by primary in vitro immunization with peptide-pulsed dendritic cells. Cancer Research, 1999. 59: p. 431-435.

Ke, N. et al., One-week 96-well soft agar growth assay for cancer target validation. Biotechniques, 2004. 36(5): p. 826-8, 830, 832-3.

Kelly et al., T-cell, adhesion, and B-cell epitopes of the cell surface streptococcus mutans protein antigen I/II. Infection and Immunity, 1995. 63(9): p. 3649-3658.

Kerbel, R. et al., Clinical translation of angiogenesis inhibitors. Nat Rev Cancer, 2002. 2(10): p. 727-39.

Kern, J.A. et al., p185neu expression in human lung adenocarcinomas predicts shortened survival. Cancer Res, 1990. 50(16): p. 5184-7.

Kim et al., Vascular endothelial growth factor proteins: Identification of biologically relevant regions by neutralizing monoclonal antibodies. Growth Factors, 1992. 7: p. 53-64.

Kim et al., Inhibtion of vascular endothelial growth vactor-induced angiogenesis suppresses tumor growth in vivo. Nature, 1993. 326: p. 841-844.

Kim, J.Y. et al., The role of ErbB2 signaling in the onset of terminal differentiation of oligodendrocytes in vivo. J Neurosci, 2003. 23(13): p. 5561-71.

Kobayashi, H. et al., Defining promiscuous MHC class II helper T-ee// epitopes for the HER2/neu tumor antigen. Cancer Res, 2000. 60(18): p. 5228-36.

Kobs-Conrad et al., Engineered topographic determinants with aB, BaB, and BaBa topologies show high affinity binding to native protein antigen (Lactate Dehydrogenase-C4). The Journal of Biological Chemistry, 1993. 268(34): p. 25285-25295.

Kohler et al., Continuous cultures of fused cells secreting antibody of predefined specificity. Nature, 1975. 256: p. 495-497.

Konecny, G.E. et al., Association between HER-2/neu and vascular endothelial growth factor expression predicts clinical outcome in primary breast cancer patients. Clin Cancer Res, 2004. 1 0(5): p. 1706-16.

Kono et al., Identification of Her-2/neu-derived peptide epitopes recognized by gastric cancer-specific cytotoxic T lymphocytes. Int. J. Cancer, 1998. 78: p. 202-208.

Kostler, W.J. et al., Single-agent trastuzumab versus trastuzumab plus cytotoxic chemotherapy in metastatic breast cancer: a single-institution experience. Anticancer Drugs, 2005. 16(2): p. 185-190.

Kozbor et al., The production of monoclonal antibodies from human lymphocytes. Immunology Today, 1983. 4: p. 72-79.

Kremer, C. et al., Up-regulation offlk-l/vascular endothelial growth factor receptor 2 by its ligand in a cerebral slice culture system. Cancer Res, 1997. 57(17): p. 3852-9.

Krishan, A., Rapid flow cytofluorometric analysis of mammalian cell cycle by propidium iodide staining J Cell Bioi, 1975. 66(1): p. 188-93.

Kumagai, T. et al., Role of extracellular subdomains of p. 185c-neu and the epidermal growth factor receptor in ligandindependent association and transactivation. Proc Natl Acad Sci U S A, 2003. 1 00(16): p. 9220-5.

Kuo, C.J. et al., Comparative evaluation of the antitumor activity of antiangiogenic proteins delivered by gene transfer. Proc Natl Acad Sci U S A, 2001. 98(8): p. 4605-10.

Kyngas, J. et al., Unreliability of the Chou-Fasman parameters in predicting protein secondary structure. Protein Engineering, 1998. 11(5): pp. 345-348.

Lairmore, M.D. et al., Human T-lymphotropic virus type 1 peptides in chimeric and multivalent constructs with promiscuous T-cell epitopes enhance immunogenicity and overcome genetic restriction. Journal of Virology, 1995. 69(10): pp. 6077-6089.

Le, X.F. et al., Roles terminal kinase, phosphoinositide of human epidermal growth factpr receptor 2, c-jun NH2—terminal kinase, phosphoinositide 3-kinase, and p70 S6 kinase pathways in regulation of cyclin G2 expression in human breast cancer cells. Molecular Cancer Therapeutics, 2007. 6: 2843-2857.

LeCouter et al., Identification of an angiogenic mitogen selective for endocrine gland endothelium. Nature, 2001. 412: p. 877-884.

Leung et al., Vascular endothelial growth factor is a secreted angiogenic mitogen. Science, 1989. 246: p. 1306-1309.

Lewis, G.D. et al., Differential responses of human tumor eel/lines to anti-p 185HER2 monoclonal antibodies. Cancer Immunol Immunother, 1993. 37(4): p. 255-63.

Li, M. et al., Reconstitution of human Fe gamma Rill cell type specificity in transgenic mice. J Exp Med, 1996. 183(3): p. 1259-63.

Lindencrona, J.A. et al., CD4+ T cell-mediated HER-2/neu-specific tumor rejection in the absence of B cells. Int J Cancer, 2004. 1 09(2): p. 259-64.

Lu et al., Identification of the residues in the extracellular region of KDR important for the interaction with vascular endothelial growth factor and neutralizing anti-KDR antibodies. Journal of Biological Chemistry, 2000. 275(19): p. 14321-14330.

Margolin et al., Phase lb trial of intravenous recombinant humanized monoclonal antibody to vascular endothelial growth factor in combination with chemotherapy in patients with advanced cancer: Pharmacologic and long-term safety data. J Clin Oncol, 2001. 19: p. 851-856.

Markman et al., Phase Ill randomized trial of 12 versus 3 months of maintenance paclitaxel in patients with advanced ovarian cancer after complete response to platinum and paclitaxel-based chemotherapy: a Southwest Oncology Group and Gynecologic Oncology Group trial. J Clin Oncol, 2003. 21: p. 2460-5.

Marmor, M.D. et al., Signal transduction and oncogenesis by ErbB/HER receptors. Int J Radiat Oncol Bioi Phys, 2004. 58(3): p. 903-13.

McGuire et al., Cyclophosphamide and cisplatin compared with paclitaxel and cisplatin in patients with stage Ill and stage IV ovarian cancer. N Engl J Med, 1996. 334: p. 1-6.

Montgomery, R.B. et al., Endogenous anti-HER2 phosphorylation and signaling through extracellular Cancer Res, 2005. 65(2): p. 650-6. antibodies block HER2 signal-regulated kinase.

Moriyama, M. et al., Expression of c-erbB-2 gene product in urinary bladder cancer. J Urol, 1991. 145(2): p. 423-7.

Morris, M.C. et al., A peptide carrier for the delivery of biologically active proteins into mammalian cells. Nat Biotechnol, 2001. 19(12): p. 1173-6.

Muller, Y.A. et al., Vascular endothelial growth factor: crystal structure and functional mapping of the kinase domain receptor binding site. Proc Natl Acad Sci US A, 1997. 94(14): p. 7192-7.

Muller, V.A. et al., VEGF and the Fab fragment of a humanized neutralizing antibody: crystal structure of the complex at 2.4 A resolution and mutational analysis of the interface. Structure, 1998. 6(9): p. 1153-67.

Nahta, R. et al., In vitro effects oftrastuzumab and vinorelbine in trastuzumab-resistant breast cancer cells. Cancer Chemother Pharmacol, 2004. 53(2): p. 186-90.

Nahta, R. et al., The HER-2-targeting antibodies trastuzumab and pertuzumab synergistically inhibit the survival of breast cancer cells. Cancer Res, 2004. 64(7): p. 2343-6.

Nair, S. et al., Synergy between tumor immunotherapy and antiangiogenic therapy. Blood, 2003. 102(3): p. 964-71.

Nanni, P. et al., Combined allogeneic tumor cell vaccination and systemic interleukin 12 prevents mammary carcinogenesis in HER-2/neu transgenic mice. J Exp Med, 2001.194(9): p. 1195-205.

Noguchi, Y. et al., Influence of interleukin 12 on p53 peptide vaccination against established Meth A sarcoma. Proceedings of the National Academy of Sciences of the United States of America, 1995. 92(6): p. 2219-23.

Ogiso, H. et al., Crystal structure of the complex of human epidermal growth factor and receptor extracellular domains. Cell, 2002. 11 0(6): p. 775-87.

Okugawa et al., A novel human HER-2-derived peptide homologous to the mouse $K^d$-restricted tumor rejection antigen can induce HLA- A24-restricted cytotoxic T lymphocytes in ovarian cancer patients and healthy individuals. Eur. J. Immunol, 2000. 30: p. 3338-3346.

Olson et al., Vascular permeability factor gene expression in normal and neoplastic human ovaries. Cancer Res, 1994. 54: p. 276-80.

Oshima, R.G. et al., Angiogenic acceleration of Neu induced mammary tumor progression and metastasis. Cancer Res, 2004. 64(1): p. 169-79.

Pal, D. et al., Beta-Sheet propensity and its correlation with parameters based on conformation. Acta Crystallographica Section D, 2000. D56: pp. 589-594.

Paley et al., Vascular endothelial growth factor expression in early stage ovarian Cancer. Cancer, 1997. 80: p. 98-106.

Park, J.B. et al., Amplification, overexpression, and rearrangement of the erbB-2 protooncogene in primary human stomach carcinomas. Cancer Res, 1989. 49(23): p. 6605-9.

Partidos, C.D. et al., Specificity of the T-cell responses in covalently linked peptides each comprising of a T helper epitope. Molecular Immunology, 1997. 34(16-17): pp. 1105-1111.

Passaniti et al., A simple, quantitative method for assessing angiogenesis and antiangiogenic agents using reconstituted basement membrane, heparin, and fibroblast growth factor. Lab Invest, 1992. 67: p. 519-528.

Pegram, M.D. et al., Combined biological therapy of breast cancer using monoclonal antibodies directed against HER2/neu protein and vascular endothelial growth factor. Semin Oncol, 2002. 29(3 Suppl 11): p. 29-37.

Pegram, M.D., et al., Phase II study of receptor-enhanced chemosensitivity using humanized anti-p185HER2/neu monoclonal antibody plus cisplatin in patients with HER2/neu-overexpressing metastatic breast cancer refractory to chemotherapy treatment. J. Clin. Oncol., 1998. 16:2659-71.

Peoples et al., Breast and ovarian cancer-specific cytotoxic T lymphocytes recognize the same HER2/neu-derived peptide. Proc. Natl. Acad. Sci. USA, 1995. 92: p. 432-436.

Perez, S.A. et al., HER-2/neu-derived peptide 884-899 is expressed by human breast, colorectal and pancreatic adenocarcinomas and is recognized by in-vitro-induced specific CD4(+) T cell clones. Cancer Immunol Immunother, 2002. 50(11): p. 615-24.

Piechocki, M.P. et al., Complementary antitumor immunity induced by plasmid DNA encoding secreted and cytoplasmic human ErbB-2. J Immunol, 2001. 167(6): p. 3367-74.

Piechocki, M.P. et al., Wei, Human ErbB-2 (Her-2) transgenic mice: a model system for testing Her-2 based vaccines. J Immunol, 2003. 171 (11): p. 5787-94.

Press, M.F. et al., Amplification and overexpression of HER-2/neu in carcinomas of the salivary gland: correlation with poor prognosis. Cancer Res, 1994. 54(21): p. 5675-82.

Pupa, S.M. et al., Prevention of spontaneous neu-expressing mammary tumor development in mice transgenic for rat proto-neu by DNA vaccination. Gene Ther, 2001. 8(1): p. 75-9.

Pupa, S.M. et al., Inhibition of Mammary Carcinoma Development in HER-2/neu Transgenic Mice through Induction of Autoimmunity by Xenogeneic DNA Vaccination. Cancer Res, 2005. 65(3): p. 1071-8.

Quaglino, E. et al., Electroporated DNA vaccine clears away multifocal mammary carcinomas in her-2/neu transgenic mice. Cancer Res, 2004. 64(8): p. 2858-64.

Reilly, R.T. et al., The collaboration of both humoral and cellular HER-2/neu-targeted immune responses is required for the complete eradication of HER-2/neu-expressing tumors. Cancer Res, 2001. 61 (3): p. 880-3.

Reilly, R.T. et al., HER-2/neu is a tumor rejection target in tolerized HER-2/neu transgenic mice. Cancer Research, 2000. 60(13): p. 3569-76.

Riemer, A.B. et al., Generation of Peptide mimics of the epitope recognized by trastuzumab on the oncogenic protein Her-2/neu. J Immunol, 2004. 173(1): p. 394-401.

Rose et al., Hydrophobicity of Amino Acid Residues in Globular Proteins. Science, 1985. 229: p. 834-838.

Rovero, S. et al., DNA vaccination against rat her-2/Neu p185 more effectively inhibits carcinogenesis than transplantable carcinomas in transgenic BALB/c mice. J Immunol, 2000. 165(9): p. 5133-42.

Rugo, H.S., Bevacizumab in the treatment of breast cancer: rationale and current data. Oncologist, 2004. 9 Suppl 1: p. 43-9.

Saito, H. et al., Relationship between the expression of vascular endothelial growth factor and the density of dendritic cells in gastric adenocarcinoma tissue. Br J Cancer, 1998. 78(12): p. 1573-7.

Sakaguchi, Regulatory T cells: key controllers of immunologic self-tolerance. Cell, 2000. 101: p. 455-8.

Sakai, Y. et al., Vaccination by genetically modified dendritic cells expressing a truncated neu oncogene prevents development of breast cancer in transgenic mice. Cancer Res, 2004. 64(21): p. 8022-8.

Salazar, L.G. et al , Immunization of cancer patients with HER-2/neu-derived peptides demonstrating high-affinity binding to multiple class II alleles. Clinical Cancer Research, 2003. 9: p. 5559-5565.

Samuelsson, A. et al., Anti-inflammatory activity of IVIG mediated through the inhibitory Fc receptor. Science, 2001. 291 (5503): p. 484-6.

Saucier, C. et al., The Shc adaptor protein is critical for VEGF induction by MET/HGF and ErbB2 receptors and for early onset of tumor angiogenesis. Proc Natl Acad Sci US A, 2004. 101(8): p. 2345-50.

Schaller, G. et al., Therapy of metastatic breast cancer with humanized antibodies against the HER2 receptor protein. J Cancer Res Clin Oncol, 1999. 125(8-9): p. 520-4.

Schirle, M. et al., Combining computer algorithms with experimental approaches permits the rapid and accurate identification of T cell epitopes from defined antigens. Journal of Immunological Methods, 2001. 257: p. 1-16.

Scholl, S. et al., Targeting HER2 in othertumortypes. Ann Oncol, 2001. 12 Suppll: p. S81-7.

Skolnick, J. et al. From genes to protein structure and function: novel applications of computational approaches in the genomic era. TIBTECH, 2000. 18: p. 34-39.

Slamon, D.J. et al., Studies of the HER-2/neu proto-oncogene in human breast and ovarian cancer. Science, 1990. 244(4905): p. 707-12.

Sliwkowski, M.X. et al., Nonclinical studies addressing the mechanism of action of trastuzumab (Herceptin). Seminars In Oncology, 1999. 26(4 Suppl 12): p. 60-70.

Sotiriadou, R. et al., Peptide HER2(776-788) represents a naturally processed broad MHC class II-restricted T cell epitope. Br J Cancer, 2001. 85(10): p. 1527-34.

Spadaro, M. et al., Immunological inhibition of carcinogenesis. Cancer Immunol Immunother, 2004. 53(3): p. 204-16.

Spiridon, C. I. et al., Targeting multiple Her-2 epitopes with monoclonal antibodies results in improved antigrowth activity of a human breast cancer eel/line in vitro and in vivo. Clin Cancer Res, 2002. 8(6): p. 1720-30.

Spiridon, C. I. et al., A comparison of the in vitro and in vivo activities of IgG and Fab2 fragments of a mixture of three monoclonal anti-Her-2 antibodies. Clin Cancer Res, 2004. 10(10): p. 3542-51.

Srinivasan, M. et al., Suppression of experimental autoimmune encephalomyelitis using peptide mimics of C02 B. J Immunol, 2002. 169(4): p. 2180-8.

Srinivasan, M. et al., A retro-inverso peptide mimic of CD28 encompassing the MYPPPY motif adopts a polyproline type II helix and inhibits encephalitogenic T cells in vitro. J Immunol, 2001. 167(1): p. 578-85.

Stedman's Medical Dictionary, entry for "Vaccine." p. 1.

Street, A.G. et al., Intrinsic Beta-Sheet propensities result from van der Waals interactions between side chains and the local backbone. Proc Natl Acad Sci, 1999. 96: 9074-9076.

Sun, J. et al., Blocking angiogenesis and tumorigenesis with GFA-116, a synthetic molecule that inhibits binding of vascular endothelial growth factor to its receptor. Cancer Res, 2004. 64(1 0): p. 3586-92.

Sun, X. et al., Angiostatin enhances 87. 1-mediated cancer immunotherapy independently of effects on vascular endothelial growth factor expression.

Tagliabue et al., Selection of monoclonal antibodies which induce internalization and phosphorylation of p185HER2 and growth inhibition of cells with HERs/neu gene amplification. International Journal of Cancer, 1991. 47: p. 933-937.

Tempfer et al., Vascular endothelial growth factor serum concentrations in ovarian cancer. Obstet Gynecol, 1998. 92: p. 360-3.

Thornton et al., Location of "continuous" antigenic determinants in the protruding regions of proteins. The EMBO Journal, 1986. 5(2): p. 409-413.
Tischer, E. et al., the human gene for vascular endothelial growth factor. Multiple protein forms are encoded through alternative exon splicing. J Bioi Chern, 1991. 266(18): p. 11947-54.
Tokuda, Y. et al., In vitro and in vivo anti-tumour effects of a humanised monoclonal antibody against cerbB-2 product. BrJ Cancer, 1996. 73(11): p. 1362-5.
Triozzi et al., Subunit peptide cancer vaccines targeting activating mutations of the p21 RAS proto-oncogene. Biomedical Peptides, Proteins, and Nucleic Acids, 1995. 1: p. 185-192.
Tuttle, T.M. et al., Proliferative and cytokine responses to class II HER-2/neuassociated peptides in breast cancer patients. Clin Cancer Res, 1998. 4(8): p. 2015-24.
Vaisman, N. et al., Specific inhibition of the reaction between a tumor-inhibitory antibody and the ErbB-2 receptor by a mimotope derived from a phage display library. Immunol Lett, 2000. 75(1): p. 61-7.
Vicari D. Evaluation of VEGF peptide mimics as inhibitors of angiogenesis, Dissertation, The Ohio State University, 2008.
Vicari, et al. VEGF peptidomimetics: an alternate approach for angiogenesis targeted therapy, ACS Conference, Jun. 13, 2008.
Vinter-Jensen, L., Pharmacological effects of epidermal growth factor (EGF) with focus on the urinary and gastrointestinal tracts. APMIS Suppl, 1999. 93: p. 1-42.
Wagner et al., Immunological Consolidation of Ovarian Carcinoma Recurrences with Monoclonal Anti-ldiotype Antibody ACA125: Immune Responses and Sruvival in Palliative Treatment. Clinical Cancer Research, 2001. 7: p. 1154-1162.
Wei et al., Immunogene therapy of tumors with vaccine based on Xenopus homologous vascular endothelial growth factor as a model antigen. Proc Natl Acad Sci, 2001. 98: p. 11545-11550.
Welling et al., Prediction of sequential antigenic regions in proteins. FEBS Lett., 1985. 188: p. 215-218.
Wolff et al., Direct gene transfer into mouse muscle in vivo. Science, 1990. 247: p. 1465-1468.
Woodbine et al., Peptide vaccine strategy for immunotherapy of human breast cancer using HER-2/neu oncogene. The American Peptide Symposium, 1995. Abstract MS009.
Woodbine et al., Biological effects of peptide antibodies raised to HER-2/neu. Implications for therapy of human breast cancer. The American Peptide Symposium, 1997. Abstract P442.
Woodbine et al., Biological effects of anti-peptide antibodies against HER-2/neu receptor tyrosine kinase: Implications for therapy of human breast cancer. Dissertation at Ohio State University, 1998.
Xu, F. et al., Antibody-induced growth inhibition is mediated through immunochemically and functionally distinct epitopes on the extracellular domain of the c-erbB-2 (HER-2/neu) gene product p185. Int J Cancer, 1993. 53(3): p. 401-8.
Yang et al., Design and synthesizing of human vascular endothelial growth factor (VEGF) peptide. US National Library of Medicine; Bethesda, MD, USA (English Abstract Only). 1999.
Yang, J.C. et al., A randomized trial of bevacizumab, an anti-vascular endothelial growth factor antibody, for metastatic renal cancer. N Engl J Med, 2003. 349(5): p. 427-34.
Ye, D. et al., Augmentation of ahumanized anti-HER2 mAb 405 induced growth inhibition by a human-mouse chimeric anti-EGF receptor mAb C225. Oncogene, 1999. 18(3): p. 731-8.
Yen, L. et al., Heregulin selectively upregulates vascular endothelial growth factor secretion in cancer cells and stimulates angiogenesis. Oncogene, 2000. 19(31): p. 3460-9.
Yip, Y.L. et al., Anti-ErbB-2 monoclonal antibodies and ErbB-2-directed vaccines. Cancer Immunol Immunother, 2002. 50(11): p. 569-87.
Yip, Y.L. et al., Identification of epitope regions recognized by tumor inhibitory and stimulatory anti-ErbB-2 monoclonal antibodies: implications for vaccine design. J Immunol, 2001. 166(8): p. 5271-8.
Zilberberg, L. et al., Structure and inhibitory effects on angiogenesis and tumor development of a new vascular endothelial growth inhibitor. J Bioi Chem, 2003. 278(37): p. 35564-73.
Preliminary Amendment filed on Mar. 4, 2008, for Australian application No. 2006261342, which claims priority to PCT/US2006/023672 filed on Jun. 15, 2006 (Applicant—The Ohio State University Research Foundation// Inventor—Kaumaya et al.) (27 pages).
Direction to request examination issued Oct. 16, 2009 for Australian application No. 2006261342, which claims priority to PCT/US2006/023672 filed on Jun. 15, 2006 (Applicant—The Ohio State University Research Foundation// Inventor—Kaumaya et al.) (1 page).
Request for examination filed Jan. 5, 2011 Request for change of inventorship filed Apr. 24, 2009 for Australian application No. 2006261342, which claims priority to PCT/US2006/023672 filed on Jun. 15, 2006 (Applicant—The Ohio State University Research Foundation// Inventor—Kaumaya et al.) (2 pages).
Office action issued Jan. 5, 2011 for Australian application No. 2006261342, which claims priority to PCT/US2006/023672 filed on Jun. 15, 2006 (Applicant—The Ohio State University Research Foundation// Inventor—Kaumaya et al.) (3 pages).
Request to enter Canadian national phase filed 12/17/07 for PCT/US2006/023672 filed Jun. 15, 2006 (Applicant—The Ohio State University Research Foundation// Inventor—Kaumaya et al.) (3 pages).
Communication regarding possible amendment to claims issued Mar. 1, 2010 for European application No. 06785065.1, which claims priority to PCT/US2006/023672 filed on Jun. 15, 2006 (Applicant—The Ohio State University Research Foundation// Inventor—Kaumaya et al.) (2 pages).
Preliminary Amedned filed Apr. 12, 2010 for European application No. 06785065.1, which claims priority to PCT/US2006/023672 filed on Jun. 15, 2006 (Applicant—The Ohio State University Research Foundation// Inventor—Kaumaya et al.) (8 pages).
Supplementary European search report issued Aug. 19, 2010 for European application No. 06785065.1 , which claims priority to PCT/US2006/023672 filed on Jun. 15, 2006 (Applicant—The Ohio State University Research Foundation// Inventor—Kaumaya et al.) (8 pages).
Invitation to declare maintenance of the application and to correct deficiencies in the Written Opinion/amend application issued Sep. 7, 2010 for European application No. 06785065.1 , which claims priority to PCT/US2006/023672 filed on Jun. 15, 2006 (Applicant—The Ohio State University Research Foundation// Inventor—Kaumaya et al.) (1 page).
Withdrawl of application issued May 6, 2011 for European application No. 06785065.1, which claims priority to PCT/US2006/023672 filed on Jun. 15, 2006 (Applicant—The Ohio State University Research Foundation// Inventor—Kaumaya et al.) (2 pages).
Request for further processing filed Jul. 18, 2011 for European application No. 06785065.1 , which claims priority to PCT/US2006/023672 filed on Jun. 15, 2006 (Applicant—The Ohio State University Research Foundation//, Inventor—Kaumaya et al.) (8 pages).
Decision to allow further processing issued Sep. 7, 2011, for European application No. 06785065.1, which claims priority to PCT/US2006/023672 filed on Jun. 15, 2006 (Applicant—The Ohio State University Research Foundation// Inventor—Kaumaya et al.) (1 page).
Office Action issued on Dec. 22, 2011 for European application No. 06785065.1 filed on Jun. 15, 2006 which claims priority to PCT/US2006/023672 filed on Jun. 15, 2006 (Applicant—The Ohio State University Research Foundation//, Inventor—Kaumaya et al.) (3 pages).
Response to Office Action filed on Jul. 2, 2012 for European application No. 06785065.1, which claims priority to PCT/US2006/023672 filed on Jun. 15, 2006 (Applicant—The Ohio State University Research Foundation//, Inventor—Kaumaya et al.) (18 pages).
Amendment of claims filed on Jun. 1, 2009 for Japanese application No. 2008-517193, which claims priority to PCT/US2006/023672 filed on Jun. 15, 2006 (Applicant—The Ohio State University Research Foundation// Inventor—Kaumaya et al.) (7 pages).
Office Action issued Oct. 17, 2011 for Japanese application No. 2008-517193 , which claims priority to PCT/US2006/023672 filed on Jun. 15, 2006 (Applicant—The Ohio State University Research Foundation// Inventor—Kaumaya et al.) (12 pages).
Response to office action filed Apr. 17, 2012 for Japanese application No. 2008-517193 , which claims priority to PCT/US2006/023672 filed on Jun. 15, 2006 (Applicant—The Ohio State University Research Foundation// Inventor—Kaumaya et al.) (6 pages).

English translation of pending claims of divisional of Japanese application No. 2008-517193 issued for Japanese application No. 2012-93680 filed Apr. 17, 2012 (Applicant—The Ohio State University Research Foundation// Inventor—Kaumaya et al.) (1 page).

Amendment to specification filed Mar. 4, 2008 for New Zeland application No. 564951, which claims priority to PCT/US2006/023672 filed on Jun. 15, 2006 (Applicant—The Ohio State University Research Foundation// Inventor—Kaumaya et al.) (27 pages).

International preliminary report on patentability issue Dec. 17, 2009 for PCT/US2006/23672 filed Jun. 15, 2006 (Applicant—The Ohio State University Research Foundation// Inventor—Kaumaya et al.) (5 pages).

Written opinion of international search report issued Jan. 17, 2008 for PCT/US2006/23672 filed Jun. 15, 2006 (Applicant—The Ohio State University Research Foundation/,% Inventor—Kaumaya et al.) (4 pages).

Preliminary amendment filed Jun. 15, 2006 for U.S. Appl. No. 11/424,526, filed on Jun. 15, 2006 (Inventor—Kaumaya et al.) (15 pages).

Restriction requirement issued Jan. 11, 2007 for U.S. Appl. No. 11/424,526, filed on Jun. 15, 2006 (Inventor—Kaumaya et al.) (15 pages).

Response to restriction requirement filed Feb. 1, 2008 for U.S. Appl. No. 11/424,526, filed on Jun. 15, 2006 (Inventor—Kaumaya et al.) (15 pages).

Non-final Office Action issued Apr. 15, 2008 for U.S. Appl. No. 11/424,526, filed on Jun. 15, 2006 (Inventor—Kaumaya et al.) (19 pages).

Response to Office Action filed Oct. 15, 2008 for U.S. Appl. No. 11/424,526, filed on Jun. 15, 2006 (Inventor—Kaumaya et al.) (14 pages).

Non-final Office Action issued Jan. 7, 2009 for U.S. Appl. No. 11/424,526, filed on Jun. 15, 2006 (Inventor—Kaumaya et al.) (9 pages).

Response to Office Action filed Jul. 7, 2009 for U.S. Appl. No. 11/424,526, filed on Jun. 15, 2006 (Inventor—Kaumaya et al.) (8 pages).

Notice of allowance issed Oct. 3009 for U.S. Appl. No. 11/424,526, filed on Jun. 15, 2006 (Inventor—Kaumaya et al.) (7 pages).

Preliminary Amendment filed Apr. 15, 2002 for U.S. Appl. No. 09/632,036, filed on Aug. 3, 2000 (Inventor—Kaumaya et al.) (34 pages).

Preliminary Amendment filed Dec. 12, 2002 for U.S. Appl. No. 09/632,036, filed on Aug. 3, 2000 (Inventor—Kaumaya et al.) (8 pages).

Restriction requirement issued Oct. 2, 2002 for U.S. Appl. No. 09/632,036, filed on Aug. 3, 2000 (Inventor—Kaumaya et al.) (6 pages).

Response to restriction requirement filed Dec. 9, 2002 for U.S. Appl. No. 09/632,036, filed on Aug. 3, 2000 (Inventor—Kaumaya et al.) (1 page).

Second Preliminary Amendment filed Apr. 15, 2002 for U.S. Appl. No. 09/632,036, filed on Aug. 3, 2000 (Inventor—Kaumaya et al.) (8 pages).

Miscellaneous Action issued Feb. 26, 2006 for U.S. Appl. No. 09/632,036, filed on Aug. 3, 2000 (Inventor—Kaumaya et al.) (2 pages).

Response to Miscellaneous Action issued Mar. 31, 2003 for U.S. Appl. No. 09/632,036, filed on Aug. 3, 2000 (Inventor—Kaumaya et al.) (2 pages).

Amendment filed May 27, 2003 for U.S. Appl. No. 09/632,036, filed on Aug. 3, 2000 (Inventor—Kaumaya et al.) (21 pages).

Restriction requirement issued Aug. 6, 2003 for U.S. Appl. No. 09/632,036, filed on Aug. 3, 2000 (Inventor—Kaumaya et al.) (13 pages).

Response to restriction requirement filed Dec. 10, 2003 for U.S. Appl. No. 09/632,036, filed on Aug. 3, 2000 (Inventor—Kaumaya et al.) (2 pages).

Communication Regarding Non-Responsive Election issued May 5, 2004 for U.S. Appl. No. 09/632,036, filed on Aug. 3, 2000 (Inventor—Kaumaya et al.) (6 pages).

Response to restriction requirement filed Jun. 9, 2004 for U.S. Appl. No. 09/632,036, filed on Aug. 3, 2000 (Inventor—Kaumaya et al.) (2 pages).

Office Action issued Oct. 15, 2004 for U.S. Appl. No. 09/632,036, filed on Aug. 3, 2000 (Inventor—Kaumaya et al.) (46 pages).

Response to Office Action filed Mar. 17, 2005 for U.S. Appl. No. 09/632,036, filed on Aug. 3, 2000 (Inventor—Kaumaya et al.) (30 pages).

Notice of Non-compliant amendment issued Jun. 17, 2005 for U.S. Appl. No. 09/632,036, filed on Aug. 3, 2000 (Inventor—Kaumaya et al.) (3 pages).

Response to Notice of Non-complient amendment issued Jun. 24, 2005 for U.S. Appl. No. 09/632,036, filed on Aug. 2, 2000 (Inventor—Kaumaya et al.) (21 pages).

Office Action issued Sep. 21, 2005 for U.S. Appl. No. 09/632,036, filed on Aug. 3, 2000 (Inventor—Kaumaya et al.) (23 pages).

Response to Office Action filed Nov. 14, 2005 for U.S. Appl. No. 09/632,036, filed on Aug. 3, 2000 (Inventor—Kaumaya et al.) (7 pages).

Notice of Allowance issued Jan. 25, 2006 for U.S. Appl. No. 09/632,036, filed on Aug. 3, 2000 (Inventor—Kaumaya et al.) (9 pages).

Restriction Requirement issued Apr. 10, 2008 for U.S. Appl. No. 11/423,194, filed on Jun. 9, 2006 (Inventor—Kaumaya et al.) (45 pages).

Response to Restriction Requirement filed Apr. 17, 2009 for U.S. Appl. No. 11/423,194, filed on Jun. 9, 2006 (Inventor—Kaumaya et al.) (2 pages).

Voluntary Amendment filed Aug. 10, 2009 for U.S. Appl. No. 11/423,194, filed on Jun. 9, 2006 (Inventor—Kaumaya et al.) (11 pages).

Notice of Allowance issued Oct. 6, 2009 for U.S. Appl. No. 11/423,194, filed on Jun. 9, 2006 (Inventor—Kaumaya et al.) (4 pages).

Restriction Requirement issued Nov. 16, 2010 for U.S. Appl. No. 12/683,114, filed on Jan. 6, 2010 (Inventor—Kaumaya et al.) (16 pages).

Response to Restriction Requirement filed Feb. 16, 2011 for U.S. Appl. No. 12/683,114, filed on Jan. 6, 2010 (Inventor—Kaumaya et al.) (2 pages).

Office Action issued Mar. 30, 2011 for U.S. Appl. No. 12/683,114, filed on Jan. 6, 2010 (Inventor—Kaumaya et al.) (9 pages).

Response to Office Action filed Aug. 26, 2011 for U.S. Appl. No. 12/683,114, filed on Jan. 6, 2010 (Inventor—Kaumaya et al.) (11 pages).

Notice of Allowance issued Sep. 29, 2011 for U.S. Appl. No. 12/683,114, filed on Jan. 6, 2010 (Inventor—Kaumaya et al.) (8 pages).

Communication regarding possible amendment to claims issued Mar. 28, 2002 for European application No. 00953823.2, which claims priority to PCT/US2000/021222 filed on Aug. 3, 2000 (Applicant—The Ohio State University Research Foundation// Inventor—Kaumaya et al.) (2 pages).

Preliminary Amendment filed May 7, 2002 for European application No. 00953823.2, which claims priority to PCT/U52000/021222 filed on Aug. 3, 2000 (Applicant—The Ohio State University Research Foundation// Inventor—Kaumaya et al.) (43 pages).

Preliminary Amendment filed May 8, 2002 for European application No. 00953823.2, which claims priority to PCT/US2000/021222 filed on Aug. 3, 2000 (Applicant—The Ohio State University Research Foundation// Inventor—Kaumaya et al.) (18 pages).

Supplementary European Search Report issued Aug. 10, 2004 for European application No. 00953823.2, which claims priority to PCT/US2000/021222 filed on Aug. 3, 2000 (Applicant—The Ohio State University Research Foundation// Inventor—Kaumaya et al.) (7 pages).

Office Action issued Nov. 18, 2005 for European application No. 00953823.2, which claims priority to PCT/US2000/021222 filed on Aug. 3, 2000 (Applicant—The Ohio State University Research Foundation// Inventor—Kaumaya et al.) (16 pages).

Request for extentsion of time filed Mar. 27, 2006 for European application No. 00953823.2, which claims priority to PCT/US2000/

021222 filed on Aug. 3, 2000 (Applicant—The Ohio State University Research Foundation// Inventor—Kaumaya et al.) (1 page).
Grant of extentsion of time issued Mar. 31, 2006 for European application No. 00953823.2, which claims priority to PCT/US2000/021222 filed on Aug. 3, 2000 (Applicant—The Ohio State University Research Foundation// Inventor—Kaumaya et al.) (1 page).
Application deemed withdrawn Jul. 7, 2006 for European application No. 00953823.2, which claims priority to PCT/US2000/021222 filed on Aug. 3, 2000 (Applicant—The Ohio State University Research Foundation// Inventor—Kaumaya et al.) (1 page).
Request to allow further processing filed Sep. 18, 2006 for European application No. 00953823.2, which claims priority to PCT/US2000/021222 filed on Aug. 3, 2000 (Applicant—The Ohio State University Research Foundation// Inventor—Kaumaya et al.) (26 pages).
Decision to allow further processing issued Oct. 9, 2006 for European application No. 00953823.2, which claims priority to PCT/US2000/021222 filed on Aug. 3, 2000 (Applicant—The Ohio State University Research Foundation// Inventor—Kaumaya et al.) (1 page).
Office Action issued Mar. 4, 2008 for European application No. 00953823.2, which claims priority to PCT/US2000/021222 filed on Aug. 3, 2000 (Applicant—The Ohio State University Research Foundation// Inventor—Kaumaya et al.) (5 pages).
Request for extentsion of time filed Jul. 11, 2008 for European application No. 00953823.2, which claims priority to PCT/US2000/021222 filed on Aug. 3, 2000 (Applicant—The Ohio State University Research Foundation// Inventor—Kaumaya et al.) (2 pages).
Grant of extentsion of time issued Jul. 16, 2008 for European application No. 00953823.2, which claims priority to PCT/US2000/021222 filed on Aug. 3, 2000 (Applicant—The Ohio State University Research Foundation// Inventor—Kaumaya et al.) (1 page).
Application deemed withdrawn Oct. 17, 2008 for European application No. 00953823.2, which claims priority to PCT/US2000/021222 filed on Aug. 3, 2000 (Applicant—The Ohio State University Research Foundation// Inventor—Kaumaya et al.) (1 page).
Request to allow further processing filed Dec. 29, 2008 for European application No. 00953823.2, which claims priority to PCT/US2000/021222 filed on Aug. 3, 2000 (Applicant—The Ohio State University Research Foundation// Inventor—Kaumaya et al.) (12 pages).
Decision to allow further processing issued Jan. 28, 2009 for European application No. 00953823.2, which claims priority to PCT/US2000/021222 filed on Aug. 3, 2000 (Applicant—The Ohio State University Research Foundation// Inventor—Kaumaya et al.) (1 page).
Office Action issued Sep. 28, 2009 for European application No. 00953823.2, which claims priority to PCT/US2000/021222 filed on Aug. 3, 2000 (Applicant—The Ohio State University Research Foundation// Inventor—Kaumaya et al.) (4 pages).
Request for extentsion of time filed Feb. 5, 2010 for European application No. 00953823.2, which claims priority to PCT/US2000/021222 filed on Aug. 3, 2000 (Applicant—The Ohio State University Research Foundation// Inventor—Kaumaya et al.) (1 page).
Grant of extentsion of time issued Feb. 11, 2010 for European application No. 00953823.2, which claims priority to PCT/US2000/021222 filed on Aug. 3, 2000 (Applicant—The Ohio State University Research Foundation// Inventor—Kaumaya et al.) (1 page).
Application deemed withdrawn May 17, 2010 for European application No. 00953823.2, which claims priority to PCT/US2000/021222 filed on Aug. 3, 2000 (Applicant—The Ohio State University Research Foundation// Inventor—Kaumaya et al.) (1 page).
Request to allow further processing filed Jul. 16, 2010 for European application No. 00953823.2, which claims priority to PCT/US2000/021222 filed on Aug. 3, 2000 (Applicant—The Ohio State University Research Foundation// Inventor—Kaumaya et al.) (11 pages).
Decision to allow further processing issued Aug. 6, 2010 for European application No. 00953823.2, which claims priority to PCT/US2000/021222 filed on Aug. 3, 2000 (Applicant—The Ohio State University Research Foundation// Inventor—Kaumaya et al.) (1 page).
Office Action issued Jan. 18, 2011 for European application No. 00953823.2, which claims priority to PCT/US2000/021222 filed on Aug. 3, 2000 (Applicant—The Ohio State University Research Foundation// Inventor—Kaumaya et al.) (6 pages).
Response to Office Action issued May 26, 2011 for European application No. 00953823.2, which claims priority to PCT/US2000/021222 filed on Aug. 3, 2000 (Applicant—The Ohio State University Research Foundation// Inventor—Kaumaya et al.) (39 pages).
Telephone communication with Office Dec. 28, 2011 for European application No. 00953823.2, which claims priority to PCT/US2000/021222 filed on Aug. 3, 2000 (Applicant—The Ohio State University Research Foundation// Inventor—Kaumaya et al.) (3 pages).
Response to communication with Office Mar. 5, 2012 for European application No. 00953823.2, which claims priority to PCT/US2000/021222 filed on Aug. 5, 2012 (Applicant—The Ohio State University Research Foundation// Inventor—Kaumaya et al.) (13 pages).
Telephone communication with Office Jun. 14, 2012 for European application No. 00953823.2, which claims priority to PCT/US2000/021222 filed on Aug. 3, 2000 (Applicant—The Ohio State University Research Foundation// Inventor—Kaumaya et al.) (3 pages).
Response to communication with Office Aug. 10, 2012 for European application No. 00953823.2, which claims priority to PCT/US2000/021222 filed on Aug. 3, 2000 (Applicant—The Ohio State University Research Foundation// Inventor—Kaumaya et al.) (4 pages).
Office Action issued Aug. 29, 2012 for European application No. 00953823.2, which claims priority to PCT/US2000/021222 filed on Aug. 3, 2000 (Applicant—The Ohio State University Research Foundation// Inventor—Kaumaya et al.) (4 pages).
Telephone communication with Office Sep. 4, 2012 for European application No. 00953823.2, which claims priority to PCT/US2000/021222 filed on Aug. 3, 2000 (Applicant—The Ohio State University Research Foundation// Inventor—Kaumaya et al.) (4 pages).
Request for extentsion of time filed Nov. 2, 2012 for European application No. 00953823.2, which claims priority to PCT/US2000/021222 filed on Aug. 3, 2000 (Applicant—The Ohio State University Research Foundation// Inventor—Kaumaya et al.) (2 pages).
Grant of extentsion of time issued Nov. 12, 2012 for European application No. 00953823.2, which claims priority to PCT/US2000/021222 filed on Aug. 3, 2000 (Applicant—The Ohio State University Research Foundation// Inventor—Kaumaya et al.) (1 page).
Request for Examination and Voluntary Amendment filed Aug. 3, 2007 for Japanese application No. 2001-513369, which claims priority to PCT/US2000/021222 filed on Aug. 3, 2000 (Applicant—The Ohio State University Research Foundation// Inventor—Kaumaya et al.) (23 pages).
Office Action issued Jun. 23, 2010 for Japanese application No. 2001-513369, which claims priority to PCT/US2000/021222 filed on Aug. 3, 2000 (Applicant—The Ohio State University Research Foundation// Inventor—Kaumaya et al.) (7 pages).
Response to Office Action as shown by amended claims filed Sep. 22, 2010 for Japanese application No. 2001-513369, which claims priority to PCT/US2000/021222 filed on Aug. 3, 2000 (Applicant—The Ohio State University Research Foundation// Inventor—Kaumaya et al.) (9 pages).
Notice of Allowance issued Nov. 29, 2010 for Japanese application No. 2001-513369, which claims priority to PCT/US2000/021222 filed on Aug. 3, 2000 (Applicant—The Ohio State University Research Foundation// Inventor—Kaumaya et al.) (3 pages).
International Preliminary Examination Report issued Jun. 28, 2001 for PCT/US2000/021222 filed on Aug. 3, 2000 (Applicant—The Ohio State University Research Foundation// Inventor—Kaumaya et al.) (5 pages).
Preliminary amendment filed Jun. 21, 2005 for U.S. Appl. No. 11/052,721, filed on Feb. 7, 2005 (Inventor—Kaumaya et al.) (11 pages).
Restriction Requirement issued Jun. 5, 2007 for U.S. Appl. No. 11/052,721, filed on Feb. 7, 2005 (Inventor—Kaumaya et al.) (7 pages).
Response To Restriction Requirement issued Aug. 6, 2007 for U.S. Appl. No. 11/052,721, filed on Feb. 7, 2005 (Inventor—Kaumaya et al.) (3 pages).
Office Action issued Oct. 2, 2007 for U.S. Appl. No. 11/052,721, filed on Feb. 7, 2005 (Inventor—Kaumaya et al.) (11 pages).
Response to Office Action filed Apr. 2, 2008 for U.S. Appl. No. 11/052,721, filed on Feb. 7, 2005 (Inventor—Kaumaya et al.) (15 pages).

Office Action issued Jul. 11, 2008 for U.S. Appl. No. 11/052,721, filed on Feb. 7, 2005 (Inventor—Kaumaya et al.) (11 pages).
Response to Office Action filed Jan. 12, 2009 for U.S. Appl. No. 11/052,721, filed on Feb. 7, 2005 (Inventor—Kaumaya et al.) (12 pages).
Office Action issued Apr. 15, 2009 for U.S. Appl. No. 11/052,721, filed on Feb. 7, 2005 (Inventor—Kaumaya et al.) (8 pages).
Response to Office Action filed Jul. 15, 2009 for U.S. Appl. No. 11/052,721, filed on Feb. 7, 2005 (Inventor—Kaumaya et al.) (6 pages).
Office Action issued Nov. 20, 2009 for U.S. Appl. No. 11/052,721, filed on Feb. 7, 2005 (Inventor—Kaumaya et al.) (7 pages).
Response to Office Action filed May 20, 2010 for U.S. Appl. No. 11/052,721, filed on Feb. 7, 2005 (Inventor—Kaumaya et al.) (10 pages).
Office Action issued Jun. 29, 2010 for U.S. Appl. No. 11/052,721, filed on Feb. 7, 2005 (Inventor—Kaumaya et al.) (10 pages).
Response to Office Action filed Dec. 29, 2010 for U.S. Appl. No. 11/052,721, filed on Feb. 7, 2005 (Inventor—Kaumaya et al.) (5 pages).
Ex Parte Quayle Action issued Feb. 25, 2011 for U.S. Appl. No. 11/052,721, filed on Feb. 7, 2005 (Inventor—Kaumaya et al.) (4 pages).
Response to Ex Parte Quayle Action filed Apr. 19, 2011 for U.S. Appl. No. 11/052,721, filed on Feb. 7, 2005 (Inventor—Kaumaya et al.) (5 pages).
Notice of Allowance issued Jun. 16, 2011 for U.S. Appl. No. 11/052,721, filed on Feb. 7, 2005 (Inventor—Kaumaya et al.) (6 pages).
Request for Continued Examination with an IDS filed Jul. 26, 2011 for U.S. Appl. No. 11/052,721, filed on Feb. 7, 2005 (Inventor—Kaumaya et al.) (3 pages).
Notice of Allowance issued Aug. 17, 2011 for U.S. Appl. No. 11/052,721, filed on Feb. 7, 2005 (Inventor—Kaumaya et al.) (5 pages).
Preliminary Amendment filed Jan. 30, 2012 for U.S. Appl. No. 13/331,891, filed on Dec. 20, 2011 (Inventor—Kaumaya et al.) (57 pages).
Restriction Requirement issued Mar. 5, 2012 for U.S. Appl. No. 13/331,891, filed on Dec. 20, 2011 (Inventor—Kaumaya et al.) (5 pages).
Response to Restriction Requirement filed May 29, 2012 for U.S. Appl. No. 13/331,891, filed on Dec. 20, 2011 (Inventor—Kaumaya et al.) (6 pages).
Office Action issued Nov. 5, 2012 for U.S. Appl. No. 13/331,891, filed on Dec. 20, 2011 (Inventor—Kaumaya et al.) (8 pages).
Office Action issed Jun. 15, 2009 for Australian application No. 2005213457, which claims priority to PCT/US2005/003747 filed on Feb. 7, 2005 (Applicant—The Ohio State University Research Foundation// Inventor—Kaumaya et al.) (2 pages).
Request for examination filed Feb. 5, 2010 for Canadian application No. 2555274, which claims priority to PCT/US2005/003747 filed on Feb. 7, 2005 (Applicant—The Ohio State University Research Foundation// Inventor—Kaumaya et al.) (2 pages).
Office Action issed Nov. 23, 2011 for Canadian application No. 2555274, which claims priority to PCT/US2005/003747 filed on Feb. 7, 2005 (Applicant—The Ohio State University Research Foundation// Inventor—Kaumaya et al.) (3 pages).
Response to Office Action filed May 23, 2012 for Canadian application No. 2555274, which claims priority to PCT/US2005/003747 filed on Feb. 7, 2005 (Applicant—The Ohio State University Research Foundation// Inventor—Kaumaya et al.) (12 pages).
Communication regarding possible amendment of claims issued Apr. 14, 2009 for European application No. 05722777.9, which claims priority to PCT/US2005/003747 filed on Feb. 7, 2005 (Applicant—The Ohio State University Research Foundation// Inventor—Kaumaya et al.) (2 pages).
Invitation to correct deficientcies issued Jun. 30, 2009 for European application No. 05722777.9, which claims priority to PCT/US2005/003747 filed on Feb. 7, 2005 (Applicant—The Ohio State University Research Foundation// Inventor—Kaumaya et al.) (3 pages).
Response to Invitation to correct deficientcies filed Aug. 24, 2009 for European application No. 05722777.9, which claims priority to PCT/US2005/003747 filed on Feb. 7, 2005 (Applicant—The Ohio State University Research Foundation// Inventor—Kaumaya et al.) (3 pages).
Supplemental European Search Report issued Feb. 3, 2010 for European application No. 05722777.9, which claims priority to PCT/US2005/003747 filed on Feb. 7, 2005 (Applicant—The Ohio State University Research Foundation// Inventor—Kaumaya et al.) (6 pages).
Communication from Examining Division issued May 27, 2010 for European application No. 05722777.9, which claims priority to PCT/US2005/003747 filed on Feb. 7, 2005 (Applicant—The Ohio State University Research Foundation// Inventor—Kaumaya et al.) (5 pages).
Request for extentsion of time filed Oct. 5, 2010 for European application No. 05722777.9, which claims priority to PCT/US2005/003747 filed on Feb. 7, 2005 (Applicant—The Ohio State University Research Foundation// Inventor—Kaumaya et al.) (1 page).
Grant of extentsion of time issued Oct. 14, 2010 for European application No. 05722777.9, which claims priority to PCT/US2005/003747 filed on Feb. 7, 2005 (Applicant—The Ohio State University Research Foundation// Inventor—Kaumaya et al.) (1 page).
Application deemed withdrawn Jan. 12, 2011 for European application No. 05722777.9, which claims priority to PCT/US2005/003747 filed on Feb. 7, 2005 (Applicant—The Ohio State University Research Foundation// Inventor—Kaumaya et al.) (1 page).
Request to allow further processing filed Mar. 16, 2011 for European application No. 05722777.9, which claims priority to PCT/US2005/003747 filed on Feb. 7, 2005 (Applicant—The Ohio State University Research Foundation// Inventor—Kaumaya et al.) (9 pages).
Decision to allow further processing issued Mar. 28, 2012 for European application No. 05722777.9, which claims priority to PCT/US2005/003747 filed on Feb. 7, 2005 (Applicant—The Ohio State University Research Foundation// Inventor—Kaumaya et al.) (1 page).
Communication from Examining Division issued Oct. 28, 2011 for European application No. 05722777.9, which claims priority to PCT/US2005/003747 filed on Feb. 7, 2005 (Applicant—The Ohio State University Research Foundation// Inventor—Kaumaya et al.) (4 pages).
Response to Communication from Examining Division filed Mar. 7, 2012 for European application No. 05722777.9, which claims priority to PCT/US2005/003747 filed on Feb. 7, 2005 (Applicant—The Ohio State University Research Foundation// Inventor—Kaumaya et al.) (27 pages).
Communication from Examining Division issued Mar. 22, 2012 for European application No. 05722777.9, which claims priority to PCT/US2005/003747 filed on Feb. 7, 2005 (Applicant—The Ohio State University Research Foundation// Inventor—Kaumaya et al.) (3 pages).
Response to Communication from Examining Division filed Jul. 31,212 for European application No. 05722777.9, which claims priority to PCT/US2005/003747 filed on Feb. 7, 2005 (Applicant—The Ohio State University Research Foundation// Inventor—Kaumaya et al.) (5 pages).
Communication from Examining Division issued Sep. 13, 2012 for European application No. 05722777.9, which claims priority to PCT/US2005/003747 filed on Feb. 7, 2005 (Applicant—The Ohio State University Research Foundation// Inventor—Kaumaya et al.) (4 pages).
International Search Report issued Mar. 26, 2009 for PCT/US2005/003747 filed on Feb. 7, 2005 (Applicant—The Ohio State University Research Foundation// Inventor Kaumaya et al.) (5 pages).
Written International Search Authority issued Feb. 20, 2009 for PCT/US2005/003747 filed on Feb. 7, 2005 (Applicant—The Ohio State University Research Foundation// Inventor—Kaumaya et al.) (6 pages).
International Preliminary Report on Patentability issued Feb. 24, 2009 for PCT/US2005/003747 filed on Feb. 7, 2005 (Applicant—The Ohio State University Research Foundation// Inventor—Kaumaya et al.) (7 pages).
Requirement for Restriction/Election issued May 24, 2012 for U.S. Appl. No. 12/700,388, filed Feb. 4, 2010 (Inventor—Kaumaya) (9 pages).

Response to Requirement for Restriction/Election filed Jun. 21, 212 with the USPTO for U.S. Appl. No. 12/700,388, filed Feb. 4, 2010 (1st Named Inventor—Kaumaya) (9 pages).

Non-final Rejection issued Jul. 5, 2012 for U.S. Appl. No. 12/700,388, filed Feb. 4, 2010 (Inventor—Kaumaya) (10 pages).

Applicant-initiated Interview Summary filed Oct. 25, 2012 for U.S. Appl. No. 12/700,388, filed Feb. 4, 2010 (Inventor—Kaumaya) (3 pages).

Preliminary Amendment filed Oct. 26, 2012 for U.S. Appl. No. 13/662,024. (Inventor—Kaumaya) (7 pages).

U.S. Appl. No. 60/690,574, filed Jun. 15, 2005, Pravin Kaumaya.

Boggio, K. et al., Interleukin 12-mediated prevention of spontaneous mammary adenocarcinomas in two lines of Her-2/neu transgenic mice. J Exp Med, 1998. 188(3): 589-596.

DiCarlo, E. et al., Analysis of mammary carcinoma onset and progression in HER-2/neu oncogene transgenic mice reveals a lobular origin. Lab Invest, 1999. 79(10): 1261-1269.

Fisk, B. et al., Existent proliferative responses of peripheral blood mononuclear cells from healthy donors and ovarian cancer patients to HER-2 peptides. Anticancer Res, 1997. 17(1A): 45-53.

Goodman, M. et al., Topochemical design of bioactive peptides and peptidomimetics. Bioorg Khim, 1992. 18(10-11): 1375-1393.

Houck, K.A. et al, The vascular endothelial growth factor family: identification of a fourth molecular species and characterization of alternative splicing of RNA. Mol Endocrinol, 1991. 5(12): 1806-1814.

Hynes, N.E. et al., The biology of erbB-2/neu/HER-2 and its role in cancer. Biochim Biophys Acta, 1994. 1198(2-3): 165-184.

Izumi, Y. et al., Tumour biology: herceptin acts as an antiangiogenic cocktail. Nature, 2002. 416(6878): 279-280.

Kaumaya et al., "Synthetic Peptides: Dream or Reality." Published in Peptides in Immunology, Wiley and Sons, Ltd. (1996) (pp. 117-148).

Kostler, W.J. et al., Single-agent trastuzumab versus trastuzumab plus cytotoxic chemotherapy in metastatic breast cancer: a single-institution experience. Anticancer Drugs, 2005. 16(2): 185-190.

Moriyama, M. et al., Expression of c-erbB-2 gene product in urinary bladder cancer. J Urol, 1991. 145(2): 423-427.

Sliwkowski, M.X. et al., Nonclinical studies addressing the mechanism of action of trastuzumab (Herceptin). Seminars In Oncology, 1999. 26(4 Suppl 12): 60-70.

Xu F. et al., Antibody-induced growth inhibition is mediated through immunochemically and functionally distinct epitopes on the extracellular domain of the c-erbB-2 (HER-2/neu) gene product p185. Int J Cancer, 1993. 53(3): 401-40.

* cited by examiner

```
   1 melaalcrwg lllallppga astqvctgtd mklrlpaspe thldmlrhly qgcqvvqgnl
  61 eltylptnas lsflqdiqev qgyvliahnq vrqvplqrlr ivrgtqlfed nyalavldng
 121 dplnnttpvt gaspgglrel qlrslteilk ggvliqrnpq lcyqdtilwk difhknnqla
 181 ltlidtnrsr achpcspmck gsrcwgesse dcqsltrtvc aggcarckgp lptdccheqc
 241 aagctgpkhs dclaclhfnh sgicelhcpa lvtyntdtfe smpnpegryt fgascvtacp
 301 ynylstdvgs ctlvcplhnq evtaedgtqr cekcskpcar vcyglgmehl revravtsan
 361 iqefagckki fgslaflpes fdgdpasnta plqpeqlqvf etleeitgyl yisawpdslp
 421 dlsvfqnlqv irgrilhnga ysltlqglgi swlglrslre lgsglalihh nthlcfvhtv
 481 pwdqlfrnph qallhtanrp edecvgegla chqlcarghc wgpgptqcvn csqflrgqec
 541 veecrvlqgl preyvnarhc lpchpecpq ngsvtcfgpe adqcvacahy kdppfcvarc
 601 psgvkpdlsy mpiwkfpdee gacqpcpinc thscvdlddk gcpaeqrasp ltsivsavvg
 661 illvvvlgvv fgilikrrqq kirkytmrrl lqetelvepl tpsgampnqa qmrilketel
 721 rkvkvlgsga fgtvykgiwi pdgenvkipv aikvlrents pkankeilde ayvmagvgsp
 781 yvsrllgicl tstvqlvtql mpygcllldhv renrgrlgsq dllnwcmqia kgmsyledvr
 841 lvhrdlaarn vlvkspnhvk itdfglarll didetyhad ggkvpikwma lesilrrrft
 901 hqsdvwsygv tvwelmtfga kpydgipare ipdllekger lpqppictid vymimvkcwm
 961 idsecrprfr elvsefsrma rdpqrfvviq nedlgpaspl dstfyrslle dddmgdlvda
1021 eeylvpqqgf fcpdpapgag gmvhhrhrss strsgggdlt lglepseeea prsplapseg
1081 agsdvfdgdl gmgaakglqs lpthdpsplq rysedptvpl psetdgyvap ltcspqpeyv
1141 nqpdvrpqpp spregplpaa rpagatlera ktlspkngv vkdvfafgga venpeyltpq
1201 ggaapqphpp pafspafdnl yywdqdpper gappstfkgt ptaenpeylg ldvpv
```

FIGURE 1

CHIMERIC PEPTIDES COMPRISING HER-2 B-CELL EPITOPES AND T-HELPER EPITOPES

CROSS-REFERENCE TO RELATED APPLICATIONS

This application is a continuation of application Ser. No. 11/424,526, filed Jun. 15, 2006, now U.S. Pat. No. 7,691,396, which claims the benefit of U.S. Provisional Application No. 60/690,574, filed Jun. 15, 2005, the entireties of which are herein incorporated by reference.

GOVERNMENT SUPPORT

The work described in this application was supported, at least in part, by grants NIH 5ROI CA 84356 from the National Institute of Health. The United States government has certain rights in this invention.

BACKGROUND

Currently, the most common approaches to treating breast cancer involve surgery, chemical intervention, and/or radiotherapy. Unless the cancer is restricted to a defined area, surgery alone cannot eliminate the cancer. Accordingly, radiation treatment is often given after surgery to destroy cancer cells that are near the surgical site and that have evaded surgery. The side effects of such treatment include skin sensitivity or itchiness, interference with the immune system, sometimes queasiness and, rarely, radiation fibrosis where an affected portion of the lung becomes fibrous. Chemotherapy may also be employed following surgery. Chemotherapy utilizes drugs that are toxic to cancer cells. Since this is not a perfectly selective system, normal cells are affected as well. Negative side effects include nausea, tiredness, loss of appetite, hair loss and diarrhea.

In view of such present therapies, attempts have been made to find additional approaches for treating breast cancer. One such approach is immunotherapy. One of the targets for an immunotherapeutic approach is the HER-2 protein. The HER-2 protein, a product of the HER-2 oncogene, is overexpressed in a variety of cancers. It is found in 50%-60% of ductal in situ carcinoma and 20%-40% of all breast cancers, as well as a substantial fraction of adenocarcinomas arising in the ovaries, prostate, colon and lung. Overexpression of the HER-2 protein is related to malignant transformation in humans. Overexpression of the HER-2 protein is also intimately associated with the aggressiveness of the malignancy, being found in one-fourth of all invasive breast cancers. Overexpression of HER-2 protein is correlated with a poor prognosis in both breast and ovarian cancer.

In recent studies, antibodies directed against the extracellular binding domain (ECD) of HER-2 have been shown to confer inhibitory effects on tumor growth in vitro and in animal models (Hudziak, R. M., et al., Mol. Cell. Biol., 9:11-65-72, 1989; Tagliabue, E., et al., Int. J. Cancer 47:933-7, 1991; Drebin, J. A., et al., Proc. Natl. Acad. Sci. USA 83:9129-33, 1986; Drebin, J. A., et al., Oncogene, 2:273-7, 1988; Drebin, J. A., et al., Oncogene, 2:387-94, 1988; and Katsumata, M., et al., Nat. Med. 1:644-8. 1995). In addition, Phase II and III clinical trials of a recombinant humanized anti-HER-2 monoclonal antibody, Trastuzumab, in patients with metastatic, HER-2-overexpressing breast cancers produced an overall response rate of 15% as a single agent. Trastuzumab has also been shown to improve survival when combined with cytotoxic chemotherapeutics (Baselga, J., et al., J. Clin. Oncol. 14:737-44, 1996; Pegram, M. D., et al., J. Clin. Oncol., 16:2659-71, 1988). A number of vaccine approaches targeting a recombinant HER-2 protein, the HER-2 ECD, or the ECD of rat neu, which is the rat homolog of HER-2 have also been evaluated. For example, strain NFS mice immunized with a vaccinia virus recombinant that expresses the ECD rat neu developed a protective antibody response against subsequent challenge with neu-transformed NIH 3T3 cells (Bernards, R., et al., Proc. Natl. Acad. Sci. USA, 84:6854-8, 1987). Immunization of BDIX rats with the same immunogen, however, did not result in antibody response nor did it inhibit the growth of syngeneic neu-expressing B 104 neuroblastoma cells, suggesting that this strategy was insufficient to induce immune responses in the rat. A polysaccharide-oncoprotein complex vaccine, consisting of the 147 amino-terminal amino acids of HER-2 ECD complexed with cholesteryl group-bearing mannan and pullulan, induced cellular and humoral immune responses that mediated rejection of HER-2-expressing sarcomas in BALB/c mice (Gu, X. G., et al., Cancer Res., 58: 3385-90, 1998). Partial protection was shown in rat neu transgenic mice destined to develop mammary tumors by immunizing with either a purified rat neu ECD (Esserman, L. J., Cancer Immunol. Immunother., 47:337-42, 1999) or neu-transfected allogeneic mouse fibroblasts (Cefai, D., et al., Int. J. Cancer, 83:393-400, 1999).

Despite the results of the studies described above, it is still uncertain whether effective immune responses can be generated in humans using cell- or protein-based vaccine strategies targeting HER-2 or the HER-2 ECD, as HER-2 is a non-mutated, "self" antigen. Accordingly, it is desirable to have additional immunotherapeutic approaches for treating or preventing breast cancer and other malignancies with which overexpression of the HER-2 protein is associated.

SUMMARY

In accordance with embodiments, HER-2 B epitopes are provided. The epitopes have a sequence of CHPEC-QPQNGSVTCFGPEADQCVACAHYKDPPFCVA (SEQ ID NO: 2); VACAHYKDPPFCVA (SEQ ID NO: 3); VARCPSGVKPDLSYMPIWKFPDEEGACQPL (SEQ ID NO: 4); IWKFPDEEGACQPL (SEQ ID NO: 5); LHCPALV-TYNTDTFESMPNPEGRYTFGASCV (SEQ ID NO: 6); ACPYNYLSTDVGSCTLVCPLHNQEVTAEDGTQRCEK (SEQ ID NO: 7); CPLHNQEVTAEDGTQRCEK (SEQ ID NO: 8); or CPINCTHSCVDLDDKGCPAEQRAS (SEQ ID NO: 9).

Additional embodiments of the invention are described in more detail herein.

BRIEF DESCRIPTION OF THE SEVERAL VIEWS OF THE DRAWINGS

The following detailed description of embodiments of the present invention can be best understood when read in conjunction with the following drawings, where like structure is indicated with like reference numerals and in which:

FIG. 1 shows the HER-2 protein sequence (SEQ ID NO: 1);

DETAILED DESCRIPTION OF EMBODIMENTS OF THE INVENTION

Figure 2:
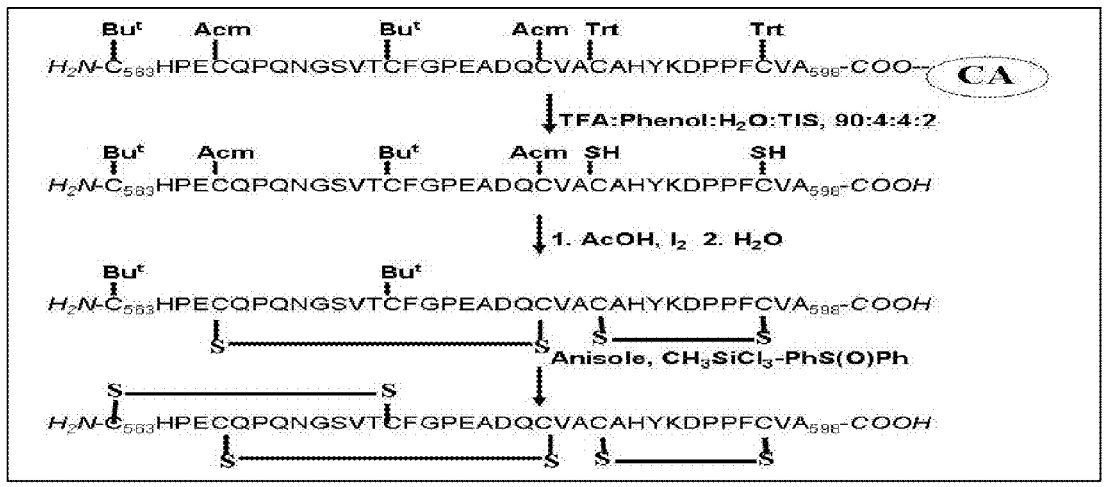
FIG. 2 shows the synthetic strategy for 3 disulfide pairings. Differential cysteine protection and selective removal and oxidation was used to generate the correct disulfide pairings as illustrated (SEQ ID NO: 27)

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

The present invention provides isolated polypeptides of the HER-2 protein, referred to hereinafter as HER-2 B epitopes. In some embodiments, the HER-2 B epitopes are immunogenic. The present invention additionally provides compositions that include one or more chimeric peptides, and the chimeric peptides include the HER-2 B epitopes. Additionally, compositions having one or more multivalent peptides are provided. These multivalent peptides include two or more of the HER-2 B epitopes. Methods of stimulating an immune response and methods of treating cancer in a subject are additionally provided. Vaccines are also provided for therapeutic and prophylactic use. The HER-2 B epitopes, either alone or in the context of chimeric peptides, as described herein, may capable of invoking a humoral response which results in the production of antibodies that are immunoreactive with the extracellular domain of the HER-2 protein. According to some embodiments, the HER-2 B epitopes or chimeric peptides confer a protective effect.

HER-2 protein, and its rat homolog neu, are transmembrane proteins with a relative molecular mass of 185 kd that is approximately 1255 amino acids (aa) in length. HER-2/neu protein has an extracellular binding domain (ECD) of approximately 645 aa, with 40% homology to epidermal growth factor receptor (EGFR), a highly hydrophobic transmembrane anchor domain (TMD), and a carboxyterminal cytoplasmic domain (CD) of approximately 580 aa with n 80% homology to EGFR. The amino acid sequence of the HER-2 protein and a nucleotide sequence which encodes such amino acid sequence are shown GenBank Accession No. M11730. FIG. 1 shows the amino acid sequence of the HER-2 protein (SEQ ID NO: 1).

The HER-2 B epitopes encompass peptides having one of the sequences, referred to hereinafter as the "reference sequences", and the sequences are:

```
                                            SEQ ID NO: 2
CHPECQPQNGSVTCFGPEADQCVACAHYKDPPFCVA,;

SEQ ID NO: 3
VACAHYKDPPFCVA,;

SEQ ID NO: 4
VARCPSGVKPDLSYMPIWKFPDEEGACQPL,;

SEQ ID NO: 5
IWKFPDEEGACQPL,;

SEQ ID NO: 6
LHCPALVTYNTDTFESMPNPEGRYTFGASCV,;
```

-continued

```
                                            SEQ ID NO: 7
ACPYNYLSTDVGSCTLVCPLHNQEVTAEDGTQRCEK,;

SEQ ID NO: 8
CPLHNQEVTAEDGTQRCEK,;
or

SEQ ID NO: 9
CPINCTHSCVDLDDKGCPAEQRAS,.
```

The HER-2 B epitopes may be cyclized or linear. When cyclized, the epitopes may be cyclized in any suitable manner. For example, disulfide bonds may be formed between selected cysteine (Cys) pairs in order to provide a desired confirmation. It is believed that the formation of cyclized epitopes may provide conformations that improve the humoral response, thus improving the protective effect.

The HER-2 B epitopes identified by SEQ ID NOs: 2-5 contain at least one region of the three regions that make contact with trastuzumab in the trastuzumab binding region of the HER-2 extracellular domain (SEQ ID NO: 1). In 2003, the crystal structure of the extracellular region of HER-2 alone and complexed to the Fab fragment of trastuzumab was published. Trastuzumab was shown to interact with three loops in subdomain IV comprising residues from SEQ ID NO: 1 in loop 1:579-583 (2 disulfide pairings between C563-0576, and between C567-0584), loop 2: 592-595 (cysteine disulfide pairing between C587-0596), and loop 3:615-625 (cysteine disulfide between C600-C623). Loops 1 and 3 are further stabilized by interaction with trastuzumab mainly through electrostatic interactions, whereas loop 2 take part in hydrophobic interactions.

The HER-2 B epitope identified by SEQ ID NO: 2 represents positions 563-598 of the HER-2 protein (SEQ ID NO: 1). The HER-2 B epitope identified by SEQ ID NO: 2 may be cyclized by the formation of a disulfide bonds between Cys-563 and Cys-576, Cys-567 and Cys-584, and/or Cys-587 and Cys-596. The HER-2 B epitope identified by SEQ ID NO: 3 represents positions 585-598. The HER-2 B epitope identified by SEQ ID NO: 3 may be cyclized by the formation of a disulfide bond between Cys-587 and Cys-596. The HER-2 B epitope identified by SEQ ID NO: 4 represents positions 597-626, and the underlined leucine (Leu) amino acid was mutated from Cys to Leu in order not to interfere with disulfide bond formation. The HER-2 B epitope identified by SEQ ID NO: 4 may be cyclized by the formation of a disulfide bond between Cys-600 and Cys-623. The HER-2 B epitope identified by SEQ ID NO: 5 represents positions 613-626, and the bold Leu amino acid was mutated from Cys to Leu in order not to interfere with disulfide bond formation as will be discussed further herein. It will be understood that the indicated Leu amino acids in SEQ ID NOs: 4 and 5 may alternatively be Cys.

The HER-2 B epitopes identified by SEQ ID NOs: 6-8 represent sequences designed to elicit antibody similar to the pertuzmab binding site of HER-2 (SEQ ID NO: 1). The HER-2 B epitope identified by SEQ ID NO: 6 represents positions 315-333 of the HER-2 protein (SEQ ID NO: 1). The HER-2 B epitope identified by SEQ ID NO: 6 may be cyclized by the formation of a disulfide bond between Cys-315 and Cys-331. The HER-2 B epitope identified by SEQ ID NO: 7 represents positions 298-333. The HER-2 B epitope identified by SEQ ID NO: 7 may be cyclized by the formation of disulfide bonds between Cys-299 and Cys-311 and/or Cys-315 and Cys-331. The HER-2 B epitope identified by SEQ ID NO: 8 represents positions 266-296. The HER-2 B epitope identified by SEQ ID NO: 8 may be cyclized by the formation of a disulfide bond between Cys-268 and Cys-295.

The HER-2 B epitope identified by SEQ ID NO: 9 represents positions 626-649. This sequence may have disulfide bonds between Cys-626 and Cys-634 and/or Cys-630 and Cys-634. It will be understood that each of epitopes having more than one Cys may be cyclized or linear.

As described herein, the HER-2 B epitopes also encompass peptides that are functional equivalents of the peptides identified by SEQ ID NOs: 2-9. Such functional equivalents have an altered sequence in which one or more of the amino acids in the corresponding HER-2 B epitope sequence is substituted or in which one or more amino acids are deleted from or added to the corresponding reference sequence. For example 1 to 3 amino acids may be added to the amino terminus, carboxy terminus, or both. In some examples, the HER-2 B epitopes are glycosylated.

In other examples, the HER-2 B epitopes may be the retro-inverso isomers of the HER-2 B epitopes. The retro-inverso modification comprises the reversal of all amide bonds within the peptide backbone. This reversal may be achieved by reversing the direction of the sequence and inverting the chirality of each amino acid residue by using D-amino acids instead of the L-amino acids. This retro-inverso isomer form may retain planarity and conformation restriction of at least some of the peptide bonds. For example, the non-retro-inverso form of SEQ ID NO: 5 may be indicated as $NH_2$-L[IWKFPDEEGACQPL]-COOH. The retro-inverso form of SEQ ID NO: 5 may be indicated as $NH_2$-D[LPQCAGEED-PFKWI]-COOH.

Non-conservative amino acid substitutions and/or conservative substitutions may be made. Substitutions are conservative amino acid substitutions when the substituted amino acid has similar structural or chemical properties with the corresponding amino acid in the reference sequence. By way of example, conservative amino acid substitutions involve substitution of one aliphatic or hydrophobic amino acids, e.g., alanine, valine, leucine and isoleucine, with another; substitution of one hydroxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, methionine, and glycine, with another.

In some examples, the deletions and additions are located at the amino terminus, the carboxy terminus, or both, of one of the sequences shown above. For example, the HER-2 B epitope equivalent has an amino acid sequence which is at least 70% identical, at least 80% identical, at least 90% identical, or at least 95% identical to the corresponding HER-2 B epitope sequences. Sequences which are at least 90% identical have no more than 1 alteration, i.e., any combination of deletions, additions or substitutions, per 10 amino acids of the reference sequence. Percent identity is determined by comparing the amino acid sequence of the variant with the reference sequence using MEGALIGN project in the DNA STAR program.

For functional equivalents that are longer than a corresponding HER-2 B epitope sequence, the functional equivalent may have a sequence which is at least 90% identical to the HER-2 B epitope sequence and the sequences which flank the HER-2 B epitope sequences in the wild-type HER-2 protein.

Functional equivalents of the HER-2 B epitopes may be identified by modifying the sequence of the epitope and then assaying the resulting polypeptide for the ability to stimulate an immune response, e.g., production of antibodies. For example, such assays may generally be performed by preparing a chimeric peptide which comprises the modified polypeptide and a Th epitope, injecting the chimeric peptide into a test animal and assaying for antibodies. Such antibodies may be found in a variety of body fluids including sera and ascites. Briefly, a body fluid sample is isolated from a warm-blooded animal, such as a human, for whom it is desired to determine whether antibodies specific for HER-2/neu polypeptide are present. The body fluid is incubated with HER-2/neu polypeptide under conditions and for a time sufficient to permit immunocomplexes to form between the polypeptide and antibodies specific for the protein and then assayed, preferably using an ELISA technique. In such technique, the colorimetric change is measured at 490 nm. Epitopes which induce production of antibodies that exhibit a titer equal to 10,000 or greater for HER-2/neu protein, may be useful. As used herein a titer of 10,000 refers to an absorbance value of 0.2 above background.

In accordance with other embodiments of the present invention, chimeric peptides and compositions comprising one or more chimeric peptides are provided. According to various embodiments, the chimeric peptides comprise a HER-2 B epitope, a T helper (Th) epitope, and a linker joining the HER-2 B epitope to the Th epitope. It will be understood that any suitable Th epitope may be used. For example, a promiscuous Th epitope may be used. As used herein a "promiscuous" Th epitope is one which promotes release of cytokines that assists in bypassing MHC restriction. It will be further understood that any suitable linker may be used. For example, depending upon the Th epitope used, the HER-2 B epitope may be linked to either the amino or the carboxy terminus of the Th epitope. The location and selection of the Th epitope depends on the structural characteristics of the HER-2 B epitope, whether alpha helical or beta-turn or strand. Methods for selecting suitable Th epitopes are described in Kaumaya et al., "De Novo" Engineering of Peptide Immunogenic and Antigenic Determinants as Potential Vaccines, in Peptides, Design, Synthesis and Biological Activity (1994), pp. 133-164, which is specifically incorporated herein by reference. A summary of the immune responses elicited a variety of Th epitopes containing B-cell epitope chimeras was presented in a review titled "Synthetic Peptides: Dream or Reality" by Kaumaya et al., and published in Peptides in Immunology, Wiley and Sons, Ltd. (1996).

In some examples, the Th epitope may be from about 14 to about 22, about 15 to 21, or 16 amino acids in length. In other embodiments, examples of suitable Th epitopes include, but are not limited to:

```
KLLSLIKGVIVHRLEGVE,;           SEQ ID NO: 10

NSVDDALINSTIYSYFPSV,;          SEQ ID NO: 11

PGINGKAIHLVNNQSSE,;            SEQ ID NO: 12

QYIKANSKFIGITEL,;              SEQ ID NO: 13

FNNFTVSFWLRVPKVSASHLE,;        SEQ ID NO: 14

LSEIKGVIVHRLEGV,;              SEQ ID NO: 15
```

```
FFLLTRILTIPQSLN,;              SEQ ID NO: 16
or

TCGVGVRVRSRVNAANKKPE,.         SEQ ID NO: 17
```

In other examples, the linker may be a peptide of from about 2 to about 15 amino acids, about 2 to about 10 amino acids, or from about 2 to about 6 amino acids in length. For example, the linker may be a peptide having the amino acid sequence Gly-Pro-Ser-Leu, SEQ ID NO: 18. The chimeric peptides may be linear or cyclized. Additionally, the HER-2 B epitopes, the Th epitopes, and/or the linker may be in retro-inverso form. Thus the HER-2 B epitope along could be in retro inverso form. Alternatively, the HER-2 B epitope and the Th epitope could be in retro inverso form. In another example, the HER-2 B epitope, the Th epitope, and the linker could be in retro inverso form.

Examples of suitable chimeric peptides include but are not limited to:

```
                                              SEQ ID NO: 19
KLLSLIKGVIVHRLEGVE-GPSL-CHPECQPQNGSVTCFGPEADQCVACA

HYKDPPFCVA,;

SEQ ID NO: 20
KLLSLIKGVIVHRLEGVE-GPSL-VACAHYKDPPFCVA,;

SEQ ID NO: 21
KLLSLIKGVIVHRLEGVE-GPSL-VARCPSGVKPDLSYMPIWKFPDEEGA

CQPL,;

SEQ ID NO: 22
KLLSLIKGVIVHRLEGVE-GPSL-IWKFPDEEGACQPL,;

SEQ ID NO: 23
KLLSLIKGVIVHRLEGVE-GPSL-LHCPALVTYNTDTFESMPNPEGRYTF

GASCV,;

SEQ ID NO: 24
KLLSLIKGVIVHRLEGVE-GPSL-ACPYNYLSTDVGSCTLVCPLHNQEVT

AEDGTQRCEK,;

SEQ ID NO: 25
KLLSLIKGVIVHRLEGVE-GPSL-CPLHNQEVTAEDGTQRCEK,;
or

SEQ ID NO: 26
KLLSLIKGVIVHRLEGVE-GPSL-CPINCTHSCVDLDDKGCPAEQRAS,.
```

The peptides of SEQ ID NOs: 19-26 have a Th epitope, a GPSL (SEQ ID NO: 18) linker and a HER-2 B epitope.

The chimeric peptides and compositions comprising the peptides may be useful immunogens for inducing production of antibodies that interact with and bind to the extracellular domain of the HER-2 protein. The chimeric peptides may also be useful as laboratory tools for detecting antibodies to HER-2 protein in a subject's sera. The chimeric peptides may invoke an antibody response in a subject and that such antibodies may (a) immunoprecipitate HER-2 protein, (b) bind to intact HER 2 receptor on ER-2 overexpressing cells in culture, and (c) reduce proliferation of HER-2 overexpressing cells in vitro. The chimeric peptides may also be used to immunize a subject and retard or prevent tumor development. The chimeric peptides may be used in vaccines to provide a protective effect.

In accordance with additional embodiments of the present invention, compositions comprising a mixture of two or more of the chimeric peptides are provided. In some examples, the HER-2 B epitope of each of the two or more chimeric peptides are different. In other examples, one of the HER-2 B epitopes is selected from SEQ ID NOs: 2-5 and another one of the HER-2 B epitopes is selected from SEQ IDS NOs: 6-8.

The HER-2 B epitopes and chimeric peptides may be synthesized using commercially available peptide synthesizers. For example, the chemical methods described in Kaumaya et al., "De Novo" Engineering of Peptide Immunogenic and Antigenic Determinants as Potential Vaccines, in Peptides, Design, Synthesis and Biological Activity (1994), pp 133-164, which is specifically incorporated herein by reference, may be used.

For example, HER-2 B-cell epitopes may be synthesized co-linearly with the Th epitope to form a chimeric peptide. Peptide synthesis may be performed using Fmoc/t-But chemistry. The HER-2 B epitopes and chimeric peptides may be cyclized in any suitable manner. For example, disulfide bonds may be achieved using differentially protected cysteine residues, iodine oxidation, the addition of water to boost Acm removal and the concomitant formation of a disulfide bond, and/or the silyl chloride-sulfoxide method.

The HER-2 B epitopes and chimeric peptides may also be produced using cell-free translation systems and RNA molecules derived from DNA constructs that encode the epitope or peptide. Alternatively, the epitopes or chimeric peptides are made by transfecting host cells with expression vectors that comprise a DNA sequence that encodes the respective epitope or chimeric peptide and then inducing expression of the polypeptide in the host cells. For recombinant production, recombinant constructs comprising one or more of the sequences which encode the epitope, chimeric peptide, or a variant thereof are introduced into host cells by conventional methods such as calcium phosphate transfection, DEAE-dextran mediated transfection, transvection, microinjection, cationic lipid-mediated transfection, electroporation, transduction, scrape lading, ballistic introduction or infection.

The HER-2 B epitope and chimeric peptide may be expressed in suitable host cells, such as for example, mammalian cells, yeast, bacteria, insect cells or other cells under the control of appropriate promoters using conventional techniques. Suitable hosts include, but are not limited to, *E. coli, P. pastoris*, Cos cells and 293 HEK cells. Following transformation of the suitable host strain and growth of the host strain to an appropriate cell density, the cells are harvested by centrifugation, disrupted by physical or chemical means, and the resulting crude extract retained for further purification of the epitope or chimeric peptide.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, and high performance liquid chromatography (HPLC), and affinity chromatography may be used to isolate the recombinant polypeptide.

To produce glycosylated epitopes and chimeric peptides, recombinant techniques may be used. For example, mammalian cells such as, Cos-7 and Hep-G2 cells be employed in the recombinant techniques. Alternatively, glycosylated epitopes and chimeric peptides may be produced using standard Fmoc/tBut synthesis. For example, one or more sugar units can be added to peptides using a chemoenzymatic approach employing endo-β-N-aceylglucosaminidases as the key enzyme for oligosaccharide transfer.

Naturally occurring variants of the HER-2 B epitopes may also be isolated by, for example, by screening an appropriate cDNA or genomic library with a DNA sequence encoding the polypeptide.

In accordance with further embodiments, multivalent peptides which comprise a plurality, i.e., at least two of the HER 2-B epitopes or functional equivalents thereof and a Th epitope are provided. The HER-2 B epitopes and Th epitope are connected to a template. For example, the HER-2 B epitopes and the Th epitope may be connected to a core β sheet template. In another example, the template may be two strands of alternating leucine and lysine residues, which are connected by a linker. The linker is an amino acid or a peptide of from about 2 to about 15 amino acids, from about 2 to about 10 amino acids, or from about 2 to about 6 amino acids in length. For example, the linker may be the amino acid sequence Gly-Pro-Ser-Leu, SEQ ID NO: 18.

Multivalent peptides may be synthesized in any suitable manner. For example, multivalent peptides may be prepared by employing a combinatorial Fmoc/t-butyl, Fmoc/benzyl and Boc benzyl strategy as well as a fourth level of differential protecting group (Npys) strategy. Details of such approach are presented in Larimore et al. (1995) Journal of Virology 69:6077-6089, which is specifically incorporated herein by reference.

In accordance with yet other embodiments of the present invention, isolated polynucleotides which encode the HER-2 B epitopes and the chimeric peptides discussed herein are provided. The present polynucleotides also encompass polynucleotides having sequences that are capable of hybridizing to the nucleotide sequences of the HER-2 B epitopes or the chimeric peptides under stringent conditions, and/or highly stringent conditions. Hybridization conditions are based on the melting temperature (Tm) of the nucleic acid binding complex or probe, as described in Berger and Kimmel (1987) Guide to Molecular Cloning Techniques, Methods in Enzymology, vol 152, Academic Press. The term "stringent conditions, as used herein, is the "stringency" which occurs within a range from about Tm-5 (5° below the melting temperature of the probe) to about 20° C. below Tm. As used herein "highly stringent" conditions employ at least 0.2×SSC buffer and at least 65° C. As recognized in the art, stringency conditions can be attained by varying a number of factors such as the length and nature, i.e., DNA or RNA, of the probe; the length and nature of the target sequence, the concentration of the salts and other components, such as formamide, dextran sulfate, and polyethylene glycol, of the hybridization solution. All of these factors may be varied to generate conditions of stringency which are equivalent to the conditions listed above.

Polynucleotides comprising sequences encoding a HER-2 B epitope or a chimeric peptide of the present invention may be synthesized in whole or in part using chemical methods or recombinant methods which are suitable. Polynucleotides which encode a HER-2 B epitope may be obtained by screening a genomic library or cDNA library with antibodies immunospecific for the HER-2 protein to identify clones containing such polynucleotide.

The polynucleotides are useful for producing a HER-2 B epitope or a chimeric peptide. For example, an RNA molecule encoding a multivalent chimeric peptide may be used in a cell-free translation systems to prepare such polypeptides. Alternatively, a DNA molecule encoding a HER-2 B epitope or a chimeric peptide may be introduced into an expression vector and used to transform cells. Suitable expression vectors include, but are not limited to, chromosomal, non-chromosomal and synthetic DNA sequences, e.g., derivatives of SV40, bacterial plasmids, phage DNAs; yeast plasmids, vectors derived from combinations of plasmids and phage DNAs, viral DNA such as vaccinia, adenovirus, fowl pox virus, pseudorabies, baculovirus, and retrovirus. The DNA sequence may introduced into the expression vector by any suitable procedure.

In accordance with further embodiments, recombinant constructs comprising one or more of the polynucleotides encoding one or more HER-2 B epitopes or chimeric peptides are provided. Suitable constructs include, for example, vectors, such as a plasmid, phagemid, or viral vector, into which a sequence that encodes the HER-2 B cell epitope or the chimeric peptide has been inserted. In the expression vector, the DNA sequence which encodes the epitope or chimeric peptide is operatively linked to an expression control sequence, i.e., a promoter, which directs mRNA synthesis. Representative examples of such promoters, include the LTR or SV40 promoter, the *E. coli* lac or trp, the phage lambda PL promoter and other promoters known to control expression of genes in prokaryotic or eukaryotic cells or in viruses. The expression vector may also contain a ribosome binding site for translation initiation and a transcription terminator. For example, the recombinant expression vectors also may include an origin of replication and a selectable marker, such as for example, the ampicillin resistance gene of *E. coli* to permit selection of transformed cells, i.e., cells that are expressing the heterologous DNA sequences. The polynucleotide sequence encoding the HER-B cell epitope or the chimeric peptide may be incorporated into the vector in frame with translation initiation and termination sequences. For example, the polynucleotide may further encode a signal sequence which is operatively linked to the amino terminus of the HER-2 B epitope or chimeric peptide.

The polynucleotides encoding the HER-2 B epitope or the chimeric peptides comprising such epitopes may be used to express recombinant peptide using suitable techniques. Such techniques include, but are not limited to, those described in Sambrook, J. et al (1989) Molecular Cloning A Laboratory Manual, Cold Spring Harbor Press, Plainview, N.Y. and Ausubel, F. M. et al. (1989) Current Protocols in Molecular Biology, John Wile & Sons, New York, N.Y. Polynucleotides encoding the HER-2 B epitope or the chimeric peptides comprising such epitopes may also be used to immunize subjects.

In accordance with yet further embodiments, methods of treating cancer are provided. The methods comprise administering a pharmaceutical composition to a subject. In other embodiments, vaccines comprising at least one chimeric peptide, multivalent peptide, or both, of the polynucleotide which encodes the same are provided. The pharmaceutical composition comprises a pharmaceutically acceptable vehicle and at least one chimeric peptide, multivalent peptide, or both, or the polynucleotide which encodes the same, as described herein. Pharmaceutically acceptable vehicles, include, but are not limited to pharmaceutically acceptable carriers, excipients or diluents. These vehicles are generally nontoxic to subjects at the dosages and concentrations employed.

In addition to the epitopes, multivalent peptides, and chimeric peptides or the polynucleotide which encodes the same, other components, such as a vehicle for antigen delivery and immunostimulatory substances designed to enhance the protein's immunogenicity are included in the pharmaceutical composition. Examples of vehicles for antigen delivery include aluminum salts, water-in-oil emulsions, biodegradable oil vehicles, oil-in-water emulsions, biodegradable microcapsules, and liposomes. For the vaccines which comprise the chimeric peptide, a suitable vehicle for antigen delivery is a biodegradable microsphere, which may be comprised of poly(D, L-lactide-co-glycolide) (PLGA).

While any suitable vehicle may be employed in the pharmaceutical compositions of this invention, the type of carrier will vary depending on the mode of administration and whether a substantial release is desired. For parenteral administration, such as subcutaneous injection, the carrier may be water, saline, alcohol, a fat, a wax, or a buffer. Biodegradable microspheres (e.g., polylactic galactide) may also be employed as vehicles for the pharmaceutical compositions of this invention. According to some embodiments, the pharmaceutical composition comprises an adjuvant.

The HER-2 chimeric and multivalent peptides and the polynucleotides which encode the same may be useful for enhancing or eliciting, in a subject or a cell line, a humoral response and, preferably, a cellular immune response (e.g., the generation of antigen-specific cytolytic T cells). In some examples the subject is a human. A subject may be afflicted with cancer or other cancer involving HER-2, such as breast cancer, or may be normal (i.e., free of detectable disease and infection). The pharmaceutical compositions and vaccines may be useful for treating women who have a family history of breast cancer or who have had breast tumors removed. According to some embodiments, "treating" means inhibiting or slowing or retarding the growth of the tumor. Such cancers include, but are not limited to, breast, lung, ovarian, bladder and prostate. In some examples, multiple intramuscular injections, at three week intervals, are used to administer the pharmaceutical composition.

EXAMPLES

Exemplary methods are described below, although methods and materials similar or equivalent to those described herein can be used in the practice or testing of the present peptides, compositions and methods. All publications and other references mentioned herein are incorporated by reference in their entirety. The materials, methods, and examples are illustrative only and not intended to be limiting.

Peptide Synthesis and HPLC Purification. Peptides were synthesized as previously described (Kaumaya 1994). Briefly, peptides were synthesized on a Milligen/Biosearch 9600 peptide synthesizer, using a 4-methylbenzhydrylamine resin as the solid support (substitution 0.54 mm/g). The Fmoc/t-butyl synthetic method was employed using 4-(hydroxymethyl) phenoxyacetic acid as the linker. After the final deprotection step, protecting groups and peptide resin bond were cleaved with 90% TFA, 5% anisole, 3% thioanisole, 2% ethanedithiol. Crude peptide was purified by semi-preparative HPLC using a Vydac C4 (10 mm×25 cm) column at 32.5° C. Buffers were 0.1% TFA in $H_2O$ and 0.1% TFA in acetonitrile. Peptides incorporate a "promiscuous" T cell epitopes MVF 288-302 (Kaumaya 1994): DW1MVF (HER-2 376-395), MVFDW4 (628-647), DW5MVF (115-136), DW6MVF (410-429).

Gel Filtration. 20 mg/ml acidified peptide solution (0.1 mg/ml in DTT) was loaded onto a Sephadex G-25 column and 5 ml fractions eluted with 0.1M HOAc. Peptide samples were measured spectrophotometrically at 235 nm and absorbance values plotted vs. time. Samples with absorbance values above 0.1 and eluting before DTT were pooled and lyophilized. The reaction was monitored for completion by Ellman's reagent at 410 nm.

Capillary Zone Electrophoresis. CZE was performed on a Beckman P/ACE System 2100 interfaced with an IBM computer. Sample was voltage separated (15 kV) in 100 mM sodium borate using a 50 cm capillary over 20 min. Eluant was monitored at 214 nm.

Circular Dichroism and mass spectrometry. Measurements were performed on a JASCO J-500 spectropolarimeter interfaced with an IBM computer. The instrument was calibrated in 0.06% (w/v) solution of ammonium-d-10-camphorsulfonate. The CD spectra of the peptides (62.5-250 uM by dilution of peptide stocks in water) were measured at ambient temperature in a 0.1 cm path length cylindrical quartz cuvette (Hellma). Mean residue ellipticity (mdeg) was calculated using the relationship $[\theta]=100\ \theta/cnl$ where is the ellipticity, c is the peptide concentration (mM), n is the number of amino acids in the peptide, and l is the path length (cm). Fast atom bombardment (FAB) mass spectrometry measurements were carried out on a inneganMat-900 instrument.

Mercuric Acetate. Peptide was dissolved in a minimal amount of water and 100 mg/mm S-tBu solution (2-10 fold excess) added. Peptide was placed under vacuum and precipitated by 2-Mercaptoethanol in a 55° C. water bath under stirring. After filtering through dampened Celite, the filtrate was rotary evaporated, acidified with 0.1% TFA in water and lyophilized.

Biological Procedures

Immunizations and animals. Female New Zealand white rabbits were obtained from Mohican Valley Rabbitry (Loudenville, Ohio). Rabbits were immunized subcutaneously at multiple sites with a total of 1 mg of peptide emulsified in CFA. Subsequent booster injections (1 mg and 500 µg in PBS) were given three and six weeks after the primary immunization. Sera were collected and complement inactivated by heating to 56° C. for 30 min. Sera aliquots were stored at −5 to −15° C. Antibodies were purified by ammonium sulfate precipitation: A stock solution of saturated ammonium sulfate solution (SAS) was prepared, autoclaved and cooled to 4° C. Antibody was allowed to precipitate by slowly adding SAS to 35% v/v under stirring in cold room. Samples were centrifuged 14,000×g 20 min and the supernate stored at −20° C. The pellet was dissolved with 0.1M PBS in ½ original volume. Fractions were then placed in Slide-a-lyzer cassettes (Pierce) and dialyzed against frequent changes of >200 volumes pH 8, 0.15M NaCl. The saline was brought to pH 8 with a few drops of 0.1M NaOH. IgG concentration was determined by radial immunodiffusion (RID) (The Binding Site, UK). Monoclonal antibodies were purchased from Oncogene Science.

Direct ELISA. U-bottom polyvinyl chloride plastic assay plates were coated with 100 µl of antigen at 2 µg/ml in PBS overnight at 4° C. Nonspecific binding sites were blocked for 1 hour with 200 µl PBS-1% BSA and plates were washed with PBT (phosphate-buffered saline containing 0.05% Tween 20 and 1% horse serum). Rabbit antiserum 1/500 or mouse antiserum 1/50 in PBT was added to antigen coated plates, serially diluted 1:2 in PBT, and incubated 2 hr at room temperature. After washing the plates, 50 µl of 1/500 goat anti-rabbit or goat anti-mouse IgG conjugated to horseradish peroxidase (Pierce Chemical Co.) was added to each well. Excess antibody conjugate was removed, and bound antibody was detected using 50 µl of 0.15% $H_2O_2$ in 24 mM citric acid, 5 mM sodium phosphate buffer, pH 5.2, with 0.5 mg/ml 2,2'-aminobis(3-ethylbenzthiazoline-6-sulfonic acid) as the chromophore. Color development was allowed to proceed for 10 min and the reaction was stopped with 25 µl of 1% sodium dodecylsulfate. Absorbance was determined at 410 nm using a Dynatech MR700ELISA reader. Results are expressed as the mean absorbance of duplicate wells after subtraction of background.

Cell Culture. Stock cultures were maintained at 37° C. in a 5% $CO_2$ incubator. All cell culture media, FCS, and supplements were purchased from GEBCO (Grand Island, N.Y.). The human breast adenocarcinoma cell lines SKBR-3 and MCF-7 were obtained from the American Type Culture Collection and was subcultured in McCoy's 5A or DMEM supplemented with 10% FCS and L-glutainine. Cav-1 was maintained in RPMI 1640 with 10% FCS and L-glutamine. Cav-was derived from a fresh colon tumor specimen which was cryopreserved and subsequently cultured; it does not express detectable levels of HER-2/neu. SKBR3 is a breast tumor cell line which overexpresses the HER-2 protein while MCF-7 expresses the normal concentration of protein.

Immunoprecipitation and Western Blotting. On day zero, $1.0×10^7$ SKBR3 cells were plated in 75 $cm^3$ cell culture flasks and allowed to adhere overnight. Anti-peptide antibodies were added (100 µg/ml) for 4 hrs. The reaction was stopped by aspirating the media and immediately adding ice cold 0.1M phosphate buffered saline (PBS). Cells were trypsinized and washed twice with cold Hank's Balanced Salts Solution (HBSS). Cold lysis buffer (150 mM NaCl; 50 mM Tris, pH 8; 10 mM EDTA, 10 mM sodium pyrophosphate, 10 mM sodium fluoride; 1% NP-40, 0.1% SDS) containing 3 mM $Na_3VO_4$, 10 µg/ml each aprotinin and leupeptin was added to cells resuspended in 100 µl HBSS. Lysis was achieved by gentle rotation at 4° C. for 20 min. After centrifugation (14,000×g, 20 min) to remove cell debris, lysates were incubated with 3-5 µg antibody and 30 µl Protein A/Protein G (Oncogene Science) overnight. Beads were pelleted by centrifugation (14,000×g 30 sec), washed twice in lysis buffer containing 1 mM $Na_3VO_4$ and boiled in SDS sample buffer 5 min.

Proteins were resolved by 7.5% SDS-PAGE, transferred to nitrocellulose and probed with antibody. Protein transfer was monitored with prestained molecular mass standards (Bio-Rad). Immunoreactive bands were detected using horse radish peroxidase conjugated goat anti rabbit immunoglobins by enhanced chemiluminescence (Amersham).

Indirect Binding Assay. SKBR3 cells or MCF-7 cells were plated at 5,000 cells/well in V-bottom plates (Linbro, McLean Va.). The cells were incubated with various concentrations of antibodies. After being washed with Hank's Balanced Salts Solution (HBSS) the cells were incubated for one hour with fluorescein isothiocyanate (FITC)-conjugated goat anti-rabbit or goat anti-mouse antibody and fixed with formalin. A mouse monoclonal Ab (Oncogene Science, Cambridge, Mass.) was used as the positive control and an anti-CD3 Ab as the negative control. The cells were analyzed by a Coulter ELITE flow cytometer (Coulter, Hialeah, Fla.), which has an argon laser for excitation at 488 nm, and a 525 run band pass filter for FITC fluorescence $5.0×10^3$ cells were counted for each sample and final processing was performed. Debris, cell clusters and dead cells were gated out by light scatted assessment before single parameter histograms were drawn.

Effect of Abs on cell proliferation. SKBR3, MCF7 and CAVI cells were plated 5,000 cells/well in V-bottom plates along with various concentrations of Ab on day zero. On day 3, cells were pulsed with [3H]thymidine (1 µCi/well) at which time they were placed in a 20° C. freezer for 1 h. After thawing at room temperature cells were harvested an a PHD cell harvester (Cambridge Tech, Inc.). Samples were incubated in 5 ml Ready Safe liquid scintillation cocktail (Beckman) and radioactivity determined by beta counter. Results are expressed as the mean CPM+/− the standard deviation (SD).

CTL Assay: In vitro stimulation. Inguinal and periaortic lymph nodes (LN) are removed 7-10 days after immunization. LN cells ($4×10^6$-$5×10^6$) are then stimulated in vitro by co-culturing with 1.5×10⁵ irradiated (10 000 rad) P815 cells pre-pulsed for 1 h with 1 μM of the appropriate CTL peptide. The culture medium used is cDMEM (DMEM supplemented with 10% FCS). Supernatant containing 30 U/ml (final) of IL-2, 2 mM L-glutamine, 10 mM Hepes and 5×10⁵ M-2-mercaptoethanol).

Seven days after in vitro stimulation, the CTL activity is tested in a standard chromium-release assay. P815 cells (10⁶) are labeled with 150 μCi sodium [$^{51}$Cr]chromate for 1 h at 37° C. in the presence or absence of the appropriate peptide (1 μM) and washed three times. Labeled targets (2×10³) are co-incubated with stimulated LN cells at predetermined ratios in 200 μl volumes in V-bottom 96 well plates. After a 4 h incubation at 37° C., the supernatants (100 μl) are harvested for γ-counting. The % specific lysis is calculated as 100× [(experimental-spontaneous release)/(total-spontaneous release)] (Valmori, et al. 1994).

Effect of antibodies in vivo. HER2 cells (3×10⁶) were suspended in 250 ul PBS, mixed with 250 μl MATRIGEL (Beckton Dickinson) on ice and injected subcutaneously into mice. Polyclonal antibodies to a total concentration of 2 mg/mouse, were injected i.p. on days 9 and 11. Tumor volume was measured twice weekly with calipers and calculated by the formula (length×width×height).

Example 1

A Conformational HER-2 B-Cell Epitope Incorporating of Two Native Disulfide Bonds Show Enhanced Tumor Cell Binding The human EGFR disulfide pairings have been defined. Based on the high homology between EGFR and HER-2, the 628-647 epitope to 626-649 to incorporate two disulfide bonds between Cys-626 and Cys-634, and Cys-630 and Cys-642. Differential side chain protection and a specialized deprotection and oxidation successfully generated the cyclized product with a desired secondary structural characteristics as determined by CD measurements. Both linear and cyclized constructs were highly immunogenic (titers >200,000) in outbred mice. Flow cytometry analysis showed that the antibodies against the cyclized epitope bound the HER-2 protein with a higher affinity than the non-cyclized epitope (mean log fluorescence 2.29 and 1.65 respectively). Antibodies against both the cyclized and non-cyclized epitopes were able to cause a reduction of growth in cells overexpressing HER-2 as measured in an anchorage-independent growth assay (31 and 58% inhibition, respectively). Antibodies against both constructs were able to elicit IFN-γ release in the presence of effector human PBMCs, with the cyclized antibodies inducing 25% higher levels of IFN-γ compared to the linear antibodies. Cyclized antibodies elicited twice the level of specific lysis compared to non-cyclized antibodies in an ADCC assay (11 and 5.6% respectively). To investigate the in vivo effect of these peptide vaccines, inbred FVB/N mice were immunized with the constructs. Both constructs were immunogenic in these mice with the cyclized construct generating higher titers. These mice were then challenged with the NT2.5 tumor cell line which has an FVB/N background. The mice immunized with the cyclized conformational construct had a reduction in tumor volume compared to both the linear and control MVF immunized mice. Cyclized vaccinated mice had the longest doubling time (6.63 days), thereby demonstrating the greatest ability to impede tumor growth compared to linear or MVF control peptide (4.31 and 4.48 days, respectively). Thus, these results show that conformational peptides for eliciting high affinity Abs has immediate application for the design of effective Her-2 vaccines.

Example 2

Design and Synthesis of Novel HER-2 B-Cell Epitopes

Four new constructs were selected for synthesis as shown in Table 1. All four constructs contain as least one region of the three regions that make contact with trastuzumab. HER-2 B epitopes were synthesized co-linearly with the MVF promiscuous Th epitope. Peptide synthesis was performed using Fmoc/t-But chemistry. The formation of three disulfide bonds for epitope 563-598 was achieved using differentially protected cysteine residues shown in FIG. 2. The first disulfide bond is formed using iodine oxidation. The addition of water boosts Acm removal and the concomitant formation of a disulfide bond between C567 and C584. The final disulfide bond between C563 and C576 was formed using the silyl chloride-sulfoxide method.

| Designation | Peptide | Sequence | M. Wt. (da) |
|---|---|---|---|
| MVF 563 SS | 563-598 peptide with 3 disulfide bonds | H₂N-KLLSLIKGVIVHRLEGVE-GPSL-CHPECQPQNGSVTCF⋯⋯CVACAHYK⋯⋯CVA-COOH | 6181 |
| MVF 585 SS | 585-598 peptide with one disulfide bond | H₂N-KLLSLIKGVIVHRLEGVE-GPSL-VACAHYK⋯⋯CVA-COOH | 3856 |
| MVF 597 SS | 597-626 peptide with one disulfide bond | H₂N-KLLSLIKGVIVHRLEGVE-GPSL-VARCPSGVKPDLSYMPIW⋯⋯⋯L-COOH | 5672 |
| MVF 613 | 613-626 peptide | H₂N-KLLSLIKGVIVHRLEGVE-GPSL-IW⋯⋯⋯L-COOH | 3977 |

Table 1 shows candidate peptide vaccines from the HER-2/Herceptin structure (SEQ ID NOs: 19-22 are disclosed respectively in order of appearance). The promiscuous T-helper epitope sequence, shown in italics, is linked to the B-cell epitope via a four residue turn sequence (GPSL; SEQ ID NO: 18). Underlined amino acids were mutated from Cys to Leu so as not to interfere with natural disulfide formation.

Example 3

Immunogenicity of HER-2 Peptides

Figure 3:
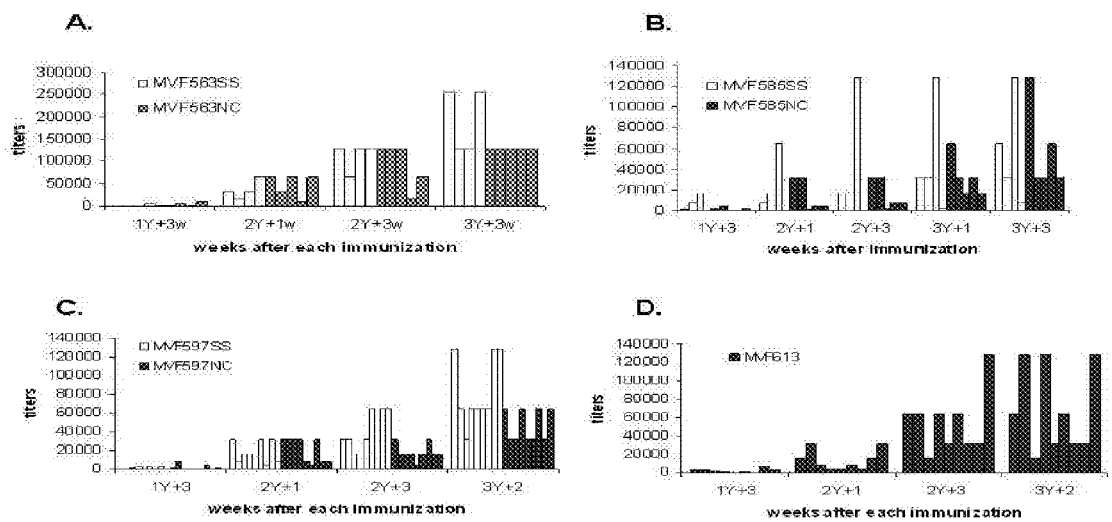
FIG. 3 shows the immune response in FVB/n mice. Groups of four to ten FVB/n mice were immunized with linear (NC) or disulfide-bonded (SS) peptide constructs (A) MVF563-598, (B) MVF585-598, (C) MVF597-626, or the linear peptide (D) MVF613-626. Each mouse is represented as an individual bar. Note that the scale in A is different then B-D.

The immunogenicity of the 4 constructs listed in Table 1 was determined using both the disulfide-bonded and linear constructs by immunizing groups of FVB/n mice (n=4-9) 6-8 weeks old. Both 563-598 cyclized and non-cyclized constructs was highly immunogenic (FIG. 3A); by three weeks after the third immunization all mice had titers above 120,000 and two mice with the cyclized construct (MVF563SS) had titers above 250,000. The 585-598 construct proved to be the least immunogenic (FIG. 3B), three weeks after the third immunization only one mouse from both the cyclized (SS) and linear (NC) groups had a titer above 120,000 with a mean titer around 58,000. Both the 597-626 and 613-626 peptide constructs were highly immunogenic (FIG. 3 C, D). Three mice that received the cyclized form of 597-626 had titers above 120,000, while no mouse that received the linear form had titers above 120,000.

Second, we tested the immunogenicity of the B-cell epitopes in neu-N transgenic mice developed by Guy et al. The neu-N transgenic mice elicited high titers of Abs (data not shown) to the peptide constructs similar to those seen in FVB/n mice even though these mice have low basal levels of neu specific IgG upon vaccination with a neu-specific whole-cell vaccine.

Example 4

Cross Reactivity of Herceptin Binding Peptides with Herceptin (Trastuzumab)

Figure 4:
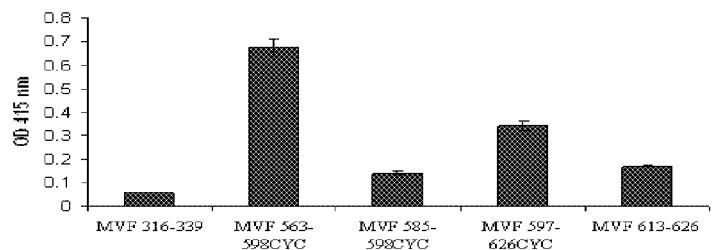
FIG. 4 shows that trastuzmab specifically recognizes peptide epitopes designed to mimic the trastuzmab binding-site of HER-2. The peptide sequences are given on the x-axis. MVF316-339 is an Her-2 irrelevant control peptide.
Figure 5A:
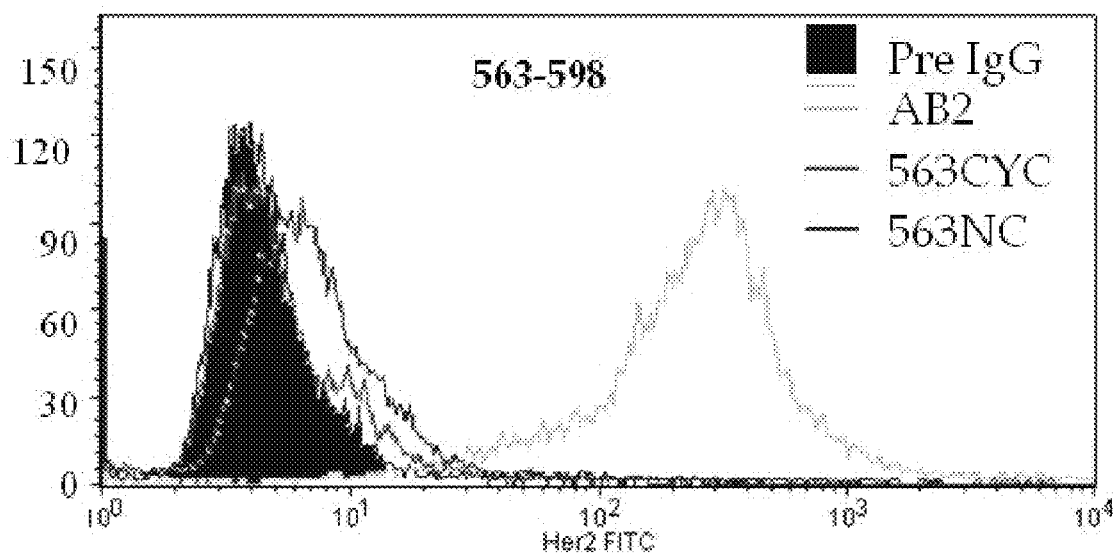
FIG. 5 shows the flow cytometry of peptide-specific antibodies with human breast cancer cells over-expressing HER-2. Flow cytometry was used to assess whether antibodies from FVB/n mice induced by various constructs recognize native HER-2. BT-474 human breast cancer cells (HER-2high) were treated with 10 µg/mL of normal mouse Ig (negative control), mouse monoclonal Ab-2 (positive control), or peptide antibodies raised in FVB/n mice.
Figure 5B:
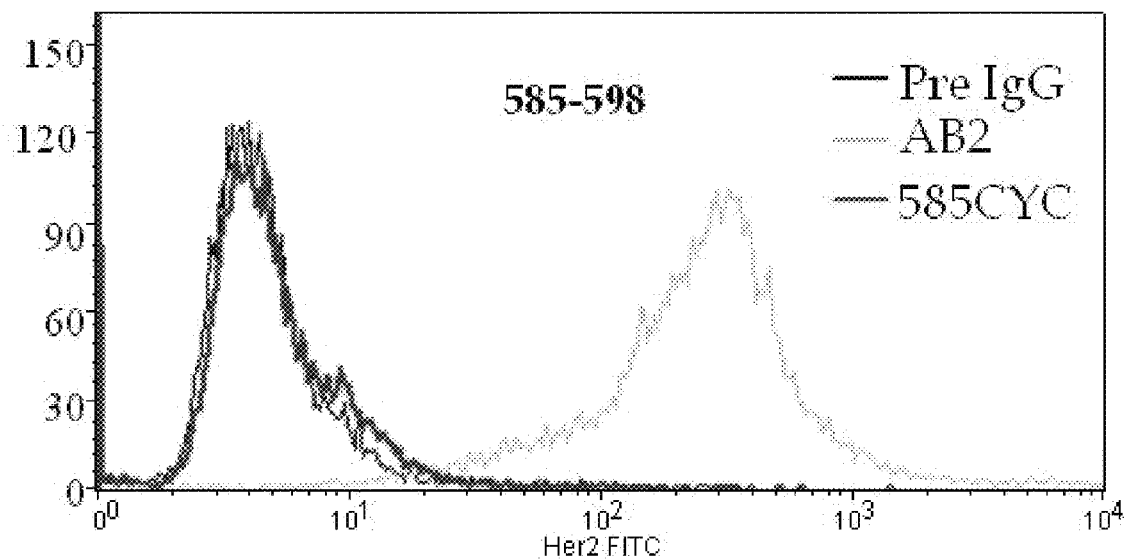
Figure 5C:
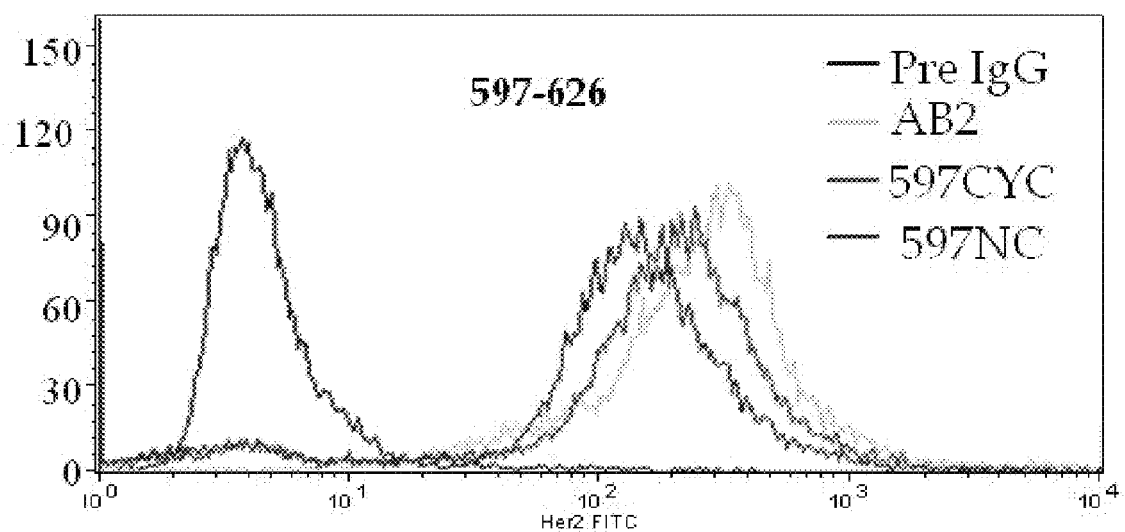
Figure 5D:
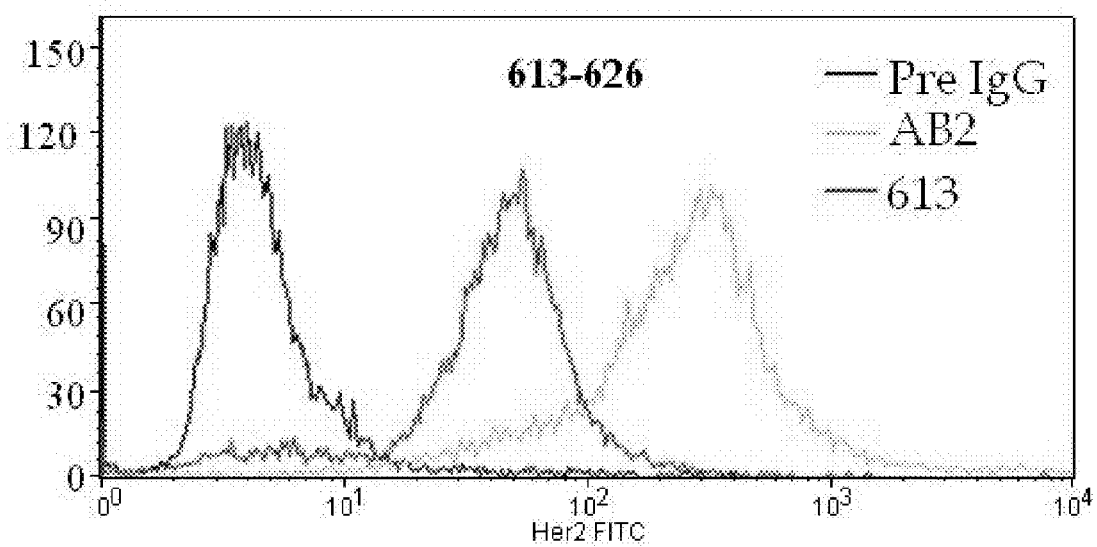
Figure 6:
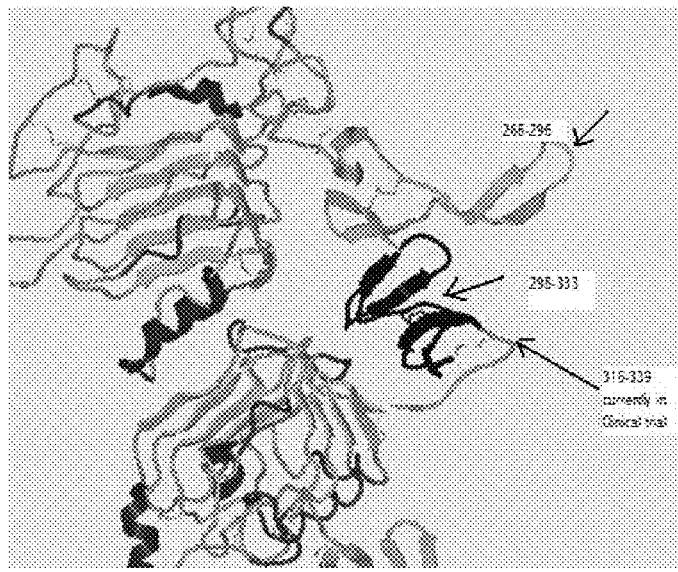
FIG. 6 shows the pertuzumab binding sites with HER-2.
Figure 7:
FIG. 7 shows the 3-dimensional structure of Herceptin Peptide epitopes.
Figure 8:
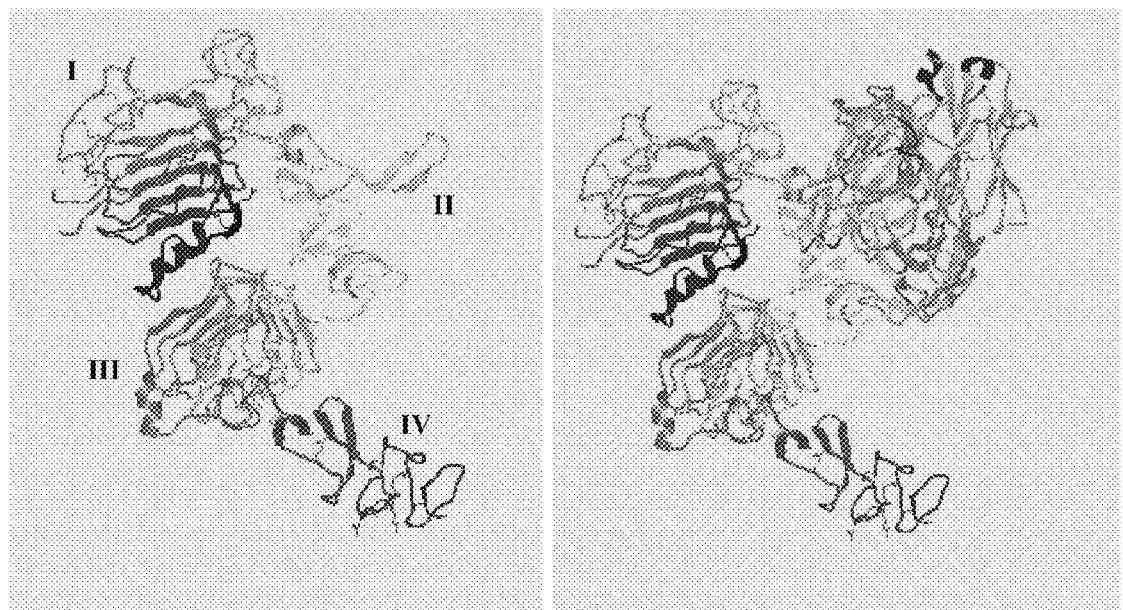
FIG. 8 shows the structure of HER-2 bound to Omnitarg™ (Pertuzumab)
Figure 9:
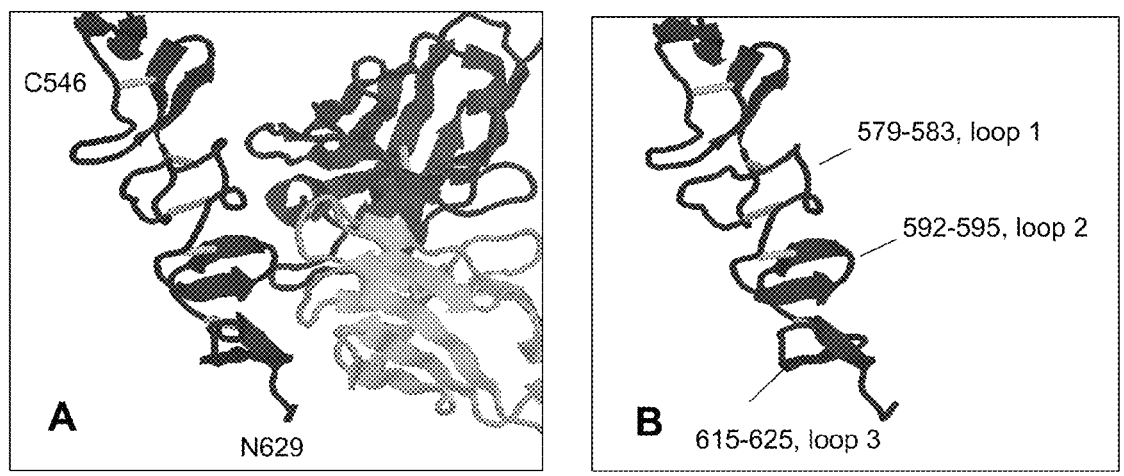
FIG. 9 shows the HER-2-trastuzumab binding site. (A) Ribbon diagram of HER-2 and the heavy and light chain of trastuzumab complex. (B) The trastuzumab binding-site of HER-2. This region is disulfide-rich. The sequences of the three loops that interact with trastuzumab are indicated.
Figure 10:
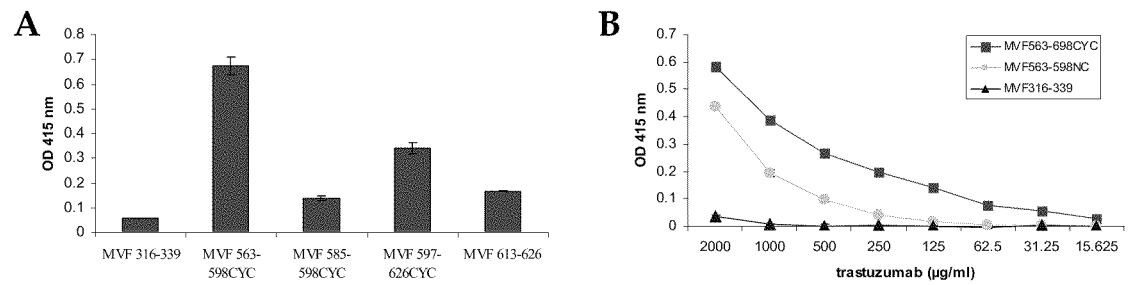
FIG. 10 shows the binding of trastuzumab to peptides. Microtiter wells were coated overnight with 2 µg/ml of various peptides and then blocked with 1% BSA for one hour. Trastuzumab was then added to plates at a concentration of 2000 µg/ml and serially diluted 1:2 with PBT. Bound trastuzumab was detected with HRP-conjugated anti-human IgG and then with substrate. (A) The $OD_{415}$ value for peptides from Table I and an irrelevant control peptide (MVF316-339) using 2000 µg/ml of trastuzumab. Values shown are the mean of duplicate samples. SEM are indicated by error bars. (B) Titration of trastuzumab with the disulfide-bound (CYC) and linear (NC) forms of MVF563-598 along with irrelevant control peptide (MVF316-339).
Figure 11:
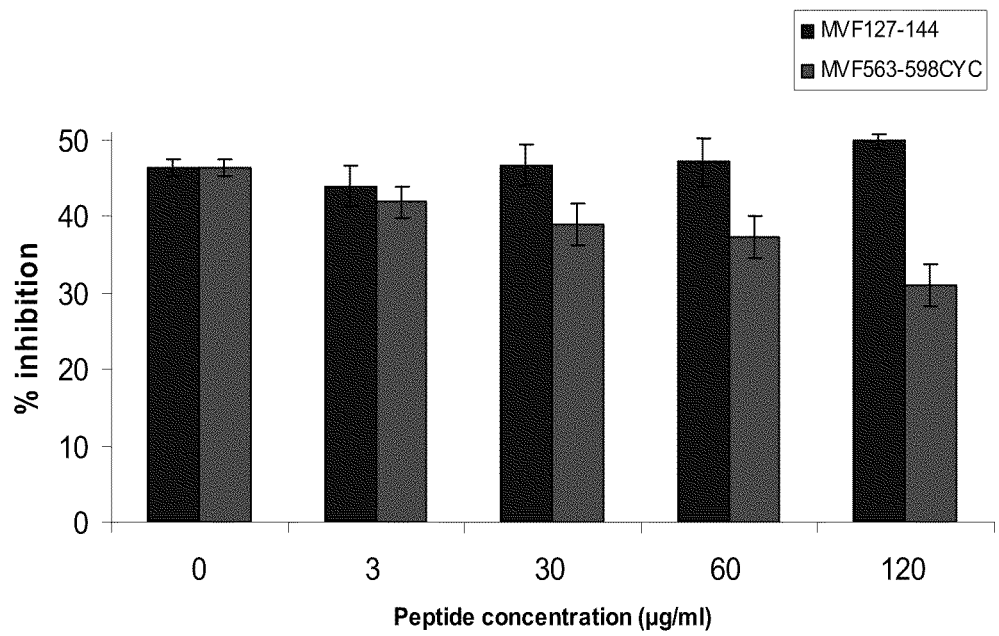
FIG. 11 shows cell proliferation by MTT assay. BT474 cells were plated in 96-well microtiter plates at 2×104 cells/well and incubated overnight at 37° C. PBS containing trastuzumab or normal human IgG (100 µg/ml) with or without peptide at the indicated concentrations was added to the wells. The plates were incubated for three days at 37° C. The number of viable cells was measured with MTT by reading $OD_{570}$. The percentage of inhibition was calculated using the formula $(OD_{normal\ human\ IgG} - OD_{trastuzumab} + peptide) / OD_{normal\ human\ IgG} \times 100$. Values shown are the mean of triplicate samples. SEM are indicated by error bars.
Figure 12:
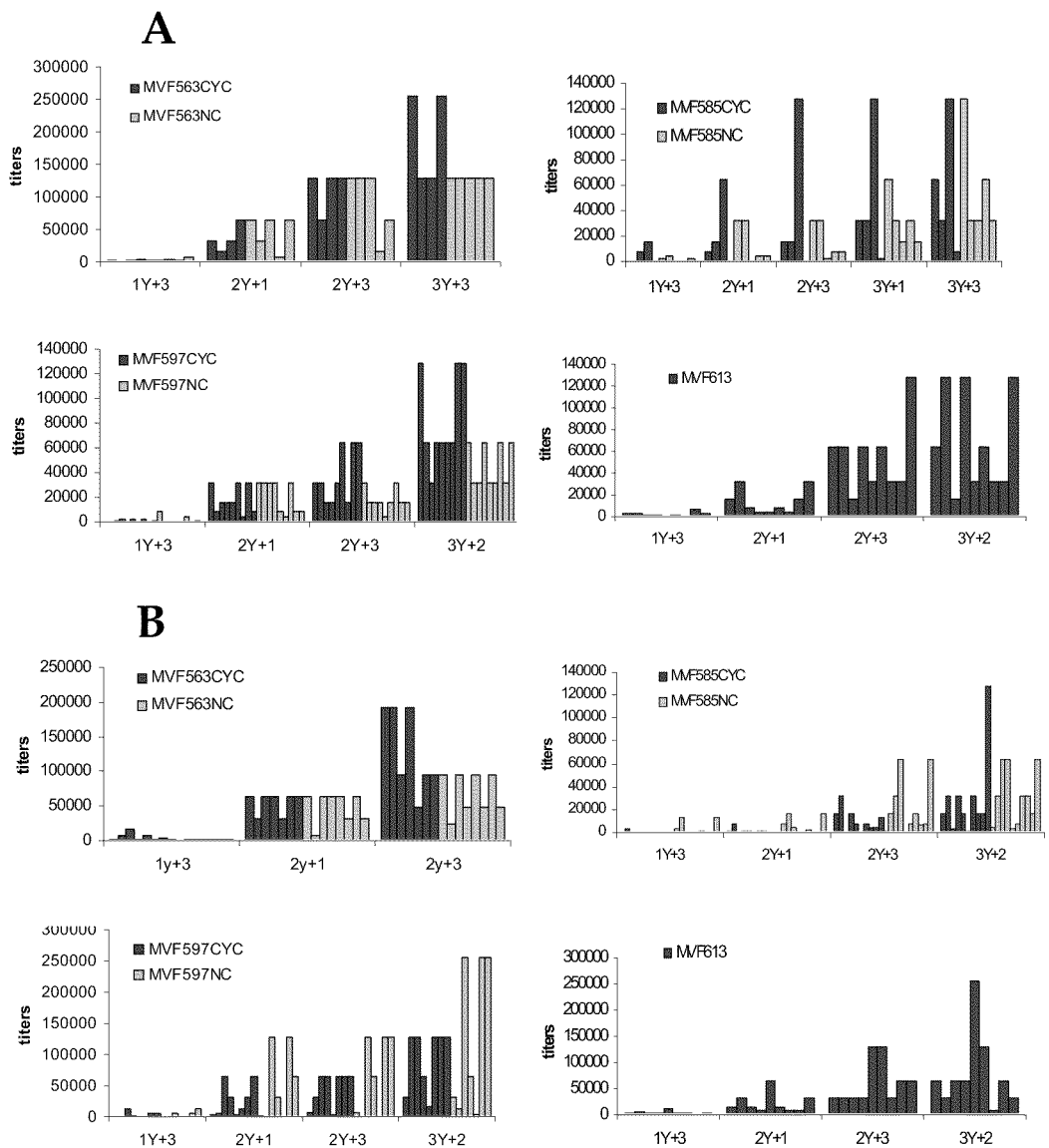
FIG. 12 shows the antibody response against peptides in FVB/n (A) and Neu-N (B) transgenic mice. Direct ELISAs were performed on sera from mice immunized with the cyclized (CYC) and linear (NC) constructs to determine differences in immunogenicity. Antibody titers against the corresponding immunogen were defined as the reciprocal of the highest dilution with absorbance ≧0.2. Each bar represents an individual mouse. Designation on the x-axis represents time at which sera was sampled, e.g. 1y+3 corresponds to serum collected three weeks after the first immunization. Neu-N mice have an FVB/n background and express normal rat neu proto-oncogene under control of a mammary-specific promoter. These mice show tolerance to neu relative to non-transgenic mice (Cancer Research 60, 3569). B demonstrates that although these mice are tolerant to rat neu they are able to generate an immune response against the peptide immunogens.
Figure 13:
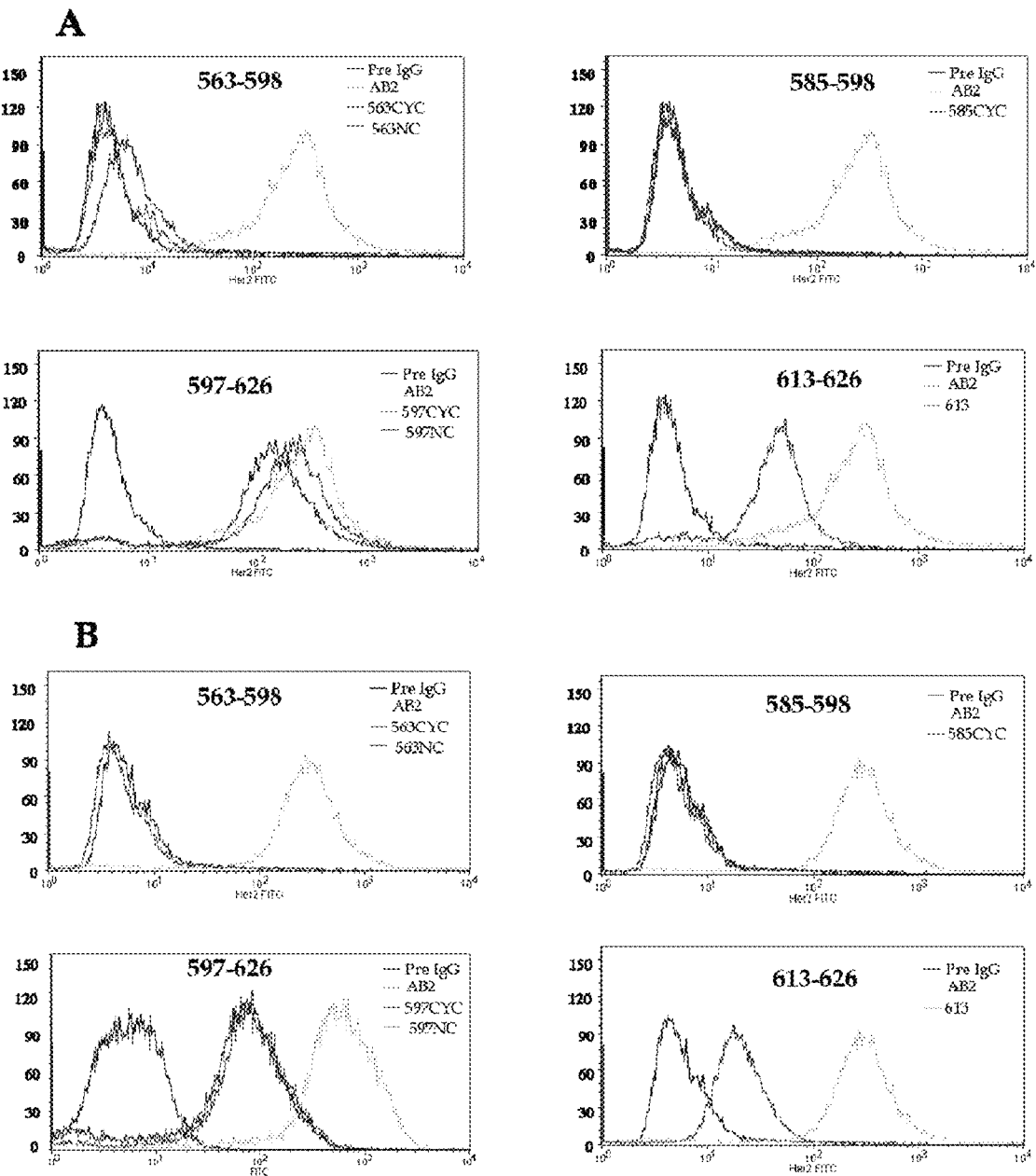
FIG. 13 shows the cross-reactivity of peptide antibodies to HER-2. The reactivity of purified antibodies from immunized mouse sera was tested with (A) BT474 and (B) SKBR-3 breast cancer cell lines using flow cytometric analysis. Ab binding was detected with goat-anti mouse FITC-conjugated abs. The x-axis represents fluorescent intensity, and the y-axis represents relative cell number. Each histogram contains an overlay of mouse pre IgG, peptide antibodies, and AB2, a mouse mAb that binds HER-2. Both cell lines demonstrate that Abs from epitopes 563-598 and 585-598 do not recognize HER-2, while Abs from epitopes 597-626 and 613-626 recognize HER-2.
Figure 14:
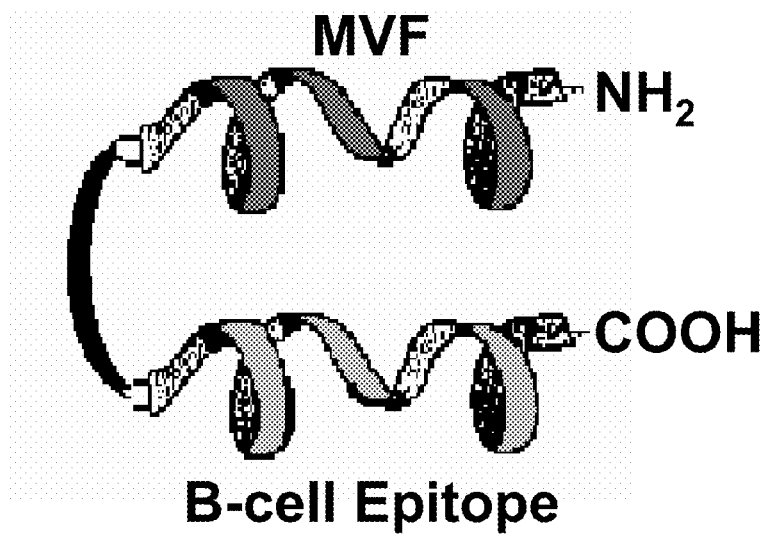
FIG. 14 shows a schematic representation of the chimeric peptide vaccine construct consisting of the 'promiscuous' Th-cell epitope MVF co-linearly synthesized with the B-cell epitope via a flexible linker (GPSL) (SEQ ID NO: 18), allowing independent folding of MVF and the B-cell epitope. This combination may help to elicit optimal antibody production by activation of both the humoral and innate arms of the immune system.
Figure 15:
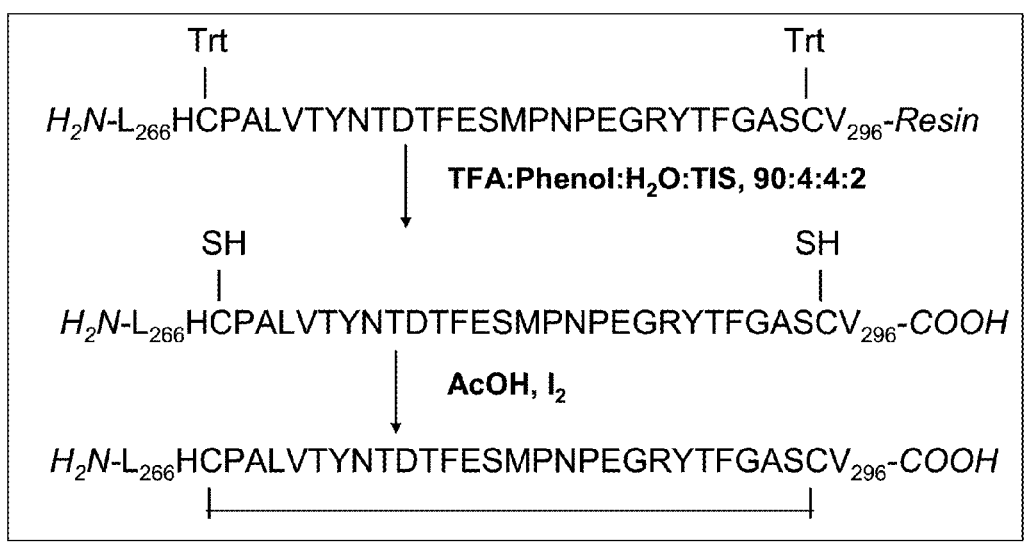
FIG. 15 shows that iodine oxidation was used to form the naturally occurring disulfide bond between Cys268 and Cys295 (SEQ ID NO: 28)
Figure 16:
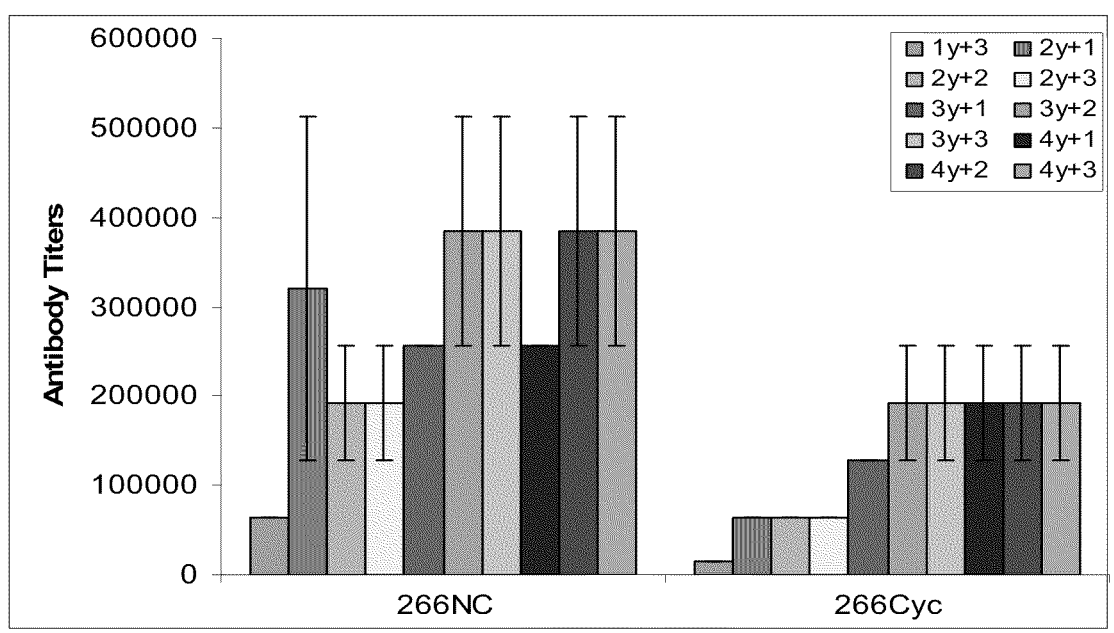
FIG. 16 shows the immunogenicity in NZW rabbits immunized with MVFHER2(266-296) non-cyclized (NC) and cyclized (CYC) peptides. Serum is collected weekly and antibodies purified for use in diagnostic studies. Antibody titers are determined by direct ELISA.
Figure 17:
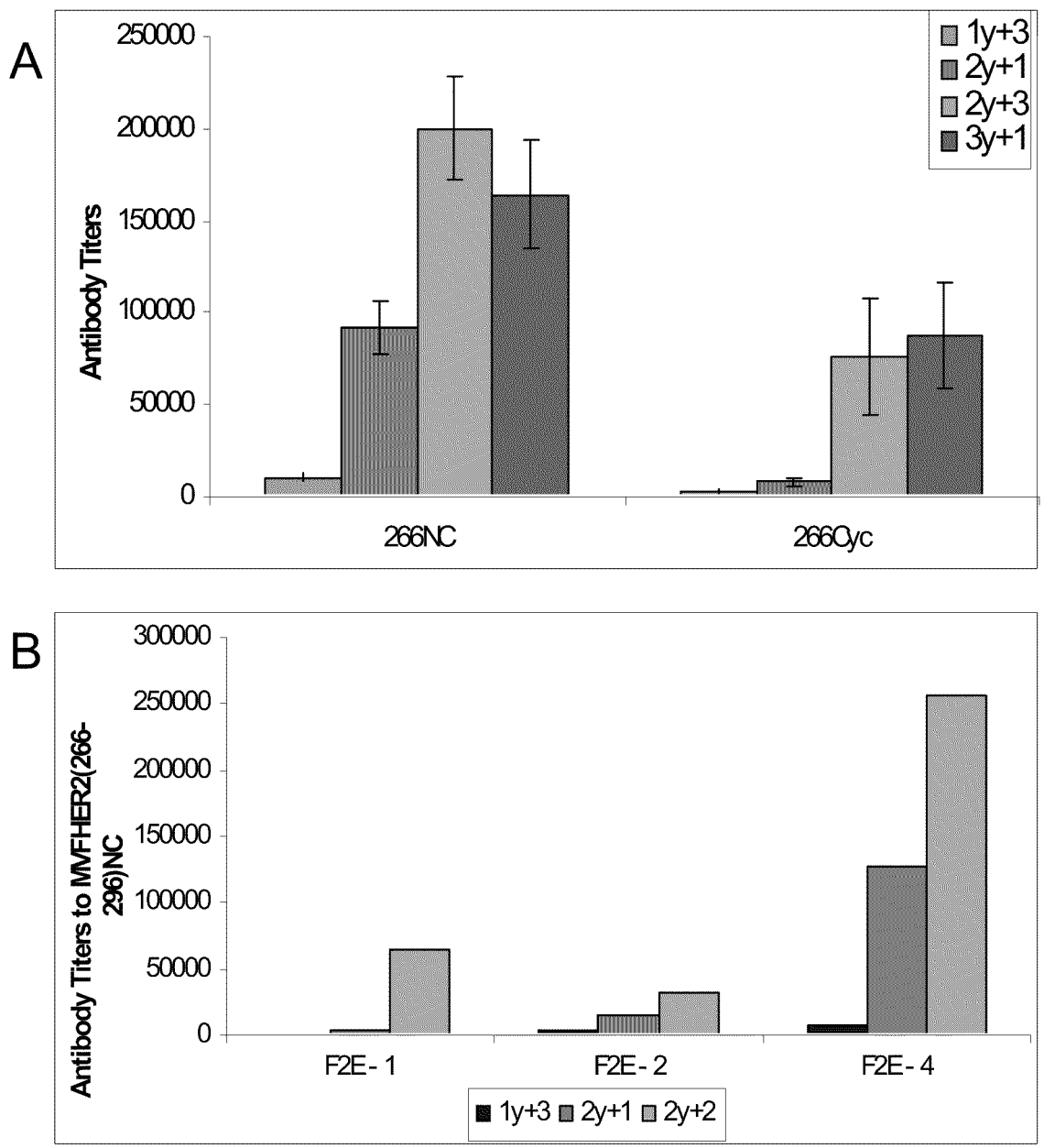
FIG. 17 shows A) immunogenicity in WT FVB/n mice immunized with either MVFHER2(266-296) cyclized (CYC) or non-cyclized (NC) peptide (8 mice/group). B) immunogenicity in 3 Neu over-expressing mice with FVB/n background. Antibody titers are determined by direct ELISA.
Figure 18:
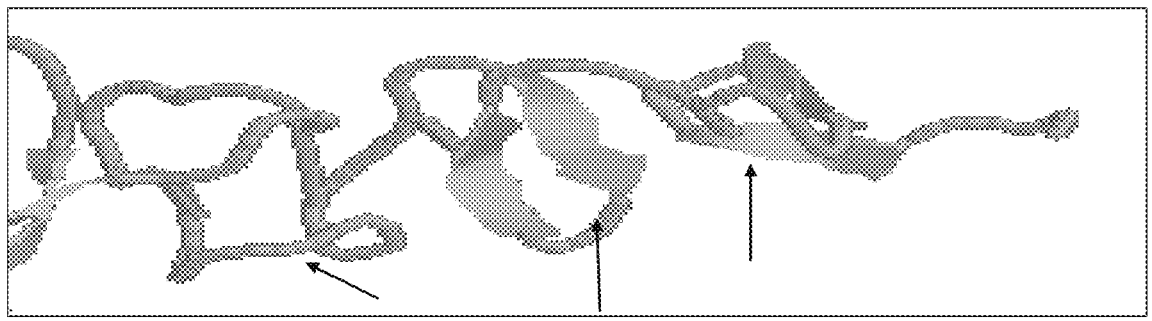
FIG. 18 shows the ribbon structure of the extracellular domain of HER-2 that interacts with herceptin. The arrows show the three loops where HER-2 makes contact with herceptin.
Figure 19:
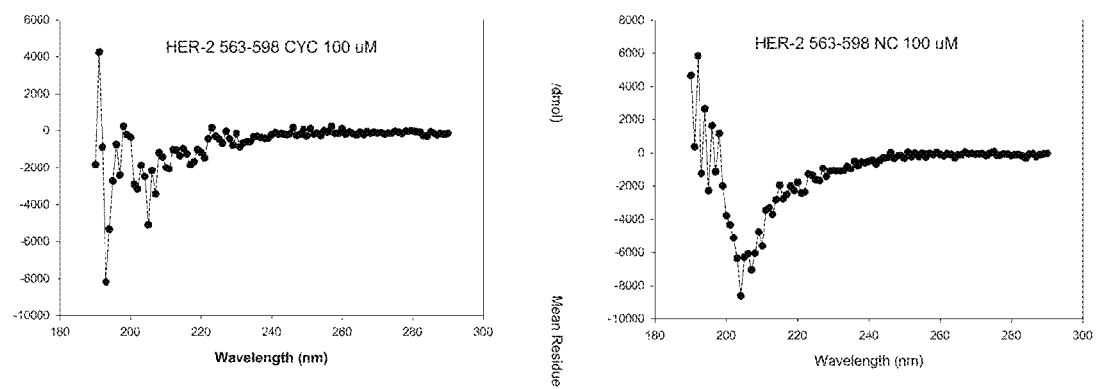
FIG. 19 shows the CD spectroscopy measurements that were performed using 100 uM solution of Her-2563-598 CYC and Her-2563-598 NC in water. Epitope HER-2 563-598 CYC, which is constrained with three disulfide bonds shows CD ellipticity minima at 193 nm, while epitope HER-2 563-598 NC free peptide shows CD ellipticity minima at 204 nm, which demonstrate significant differences in secondary structure.
Figure 20:
FIG. 20 shows the HER-2 563-598 epitope (SEQ ID NO: 29), and strategy for selective oxidation, reduction and disulfide bond analysis using a biotinylation agent, which attacks free sulfhydryl groups and therefore can be used to determine the completion of disulfide pairing.
Figure 21:
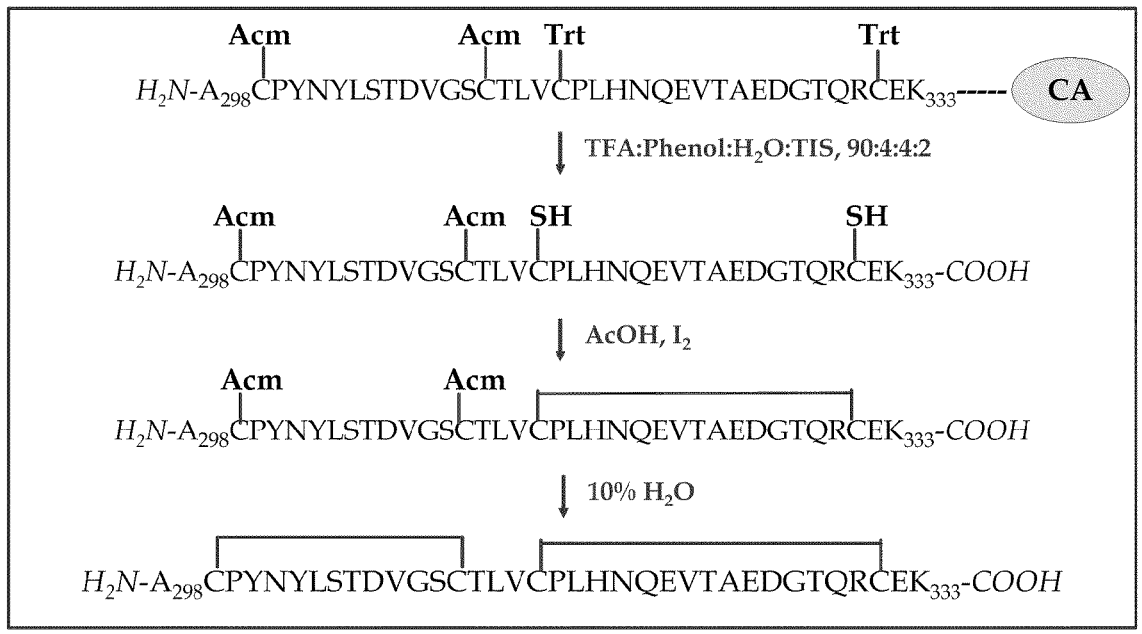
FIG. 21 shows the regioselective disulfide formation. Side chain protection for residues 315 and 331 was trityl, which was conveniently removed upon cleavage from the resin. The side chain of cysteine residues at 299 and 311 was protected with Acm, which can be selectively removed and cyclized by oxidation (12) after the first cyclization (SEQ ID NO: 30)
Figure 22:
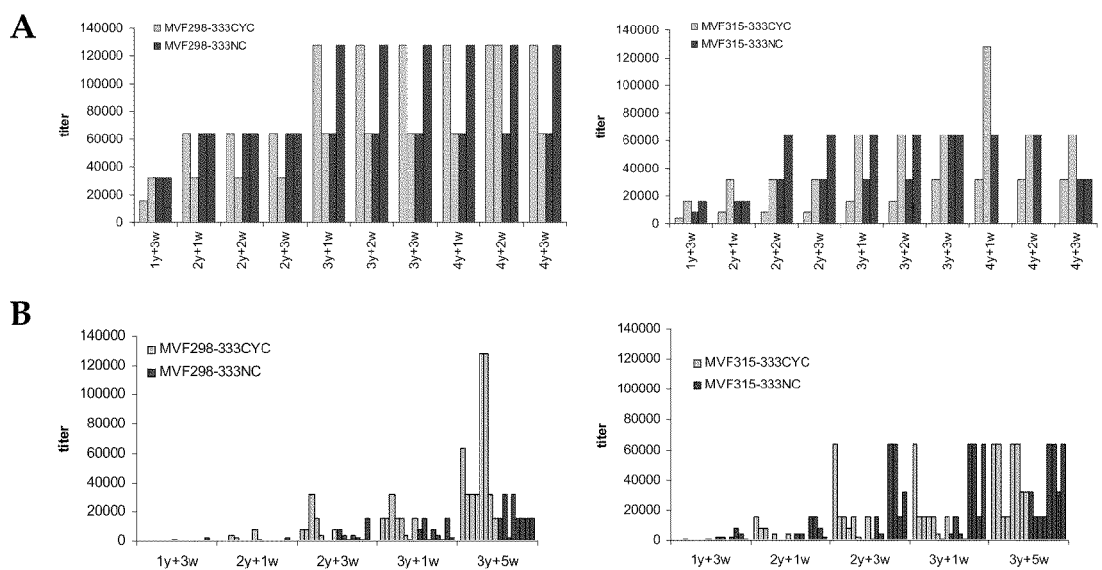
FIG. 22 shows the antibody response against peptides in out bred NZW rabbits (A) and inbred FVB/n mice (B). Direct ELISAs were performed on sera from animals immunized with the cyclized (CYC) and linear (NC) constructs to determine differences in immunogenicity. Antibody titers against the corresponding immunogen were defined as the reciprocal of the highest dilution with absorbance ≧0.2. Each bar represents an individual animal. Designation on the x-axis represents time at which sera was sampled, e.g. 1y+3w corresponds to serum collected three weeks after the first immunization.
Figure 23:
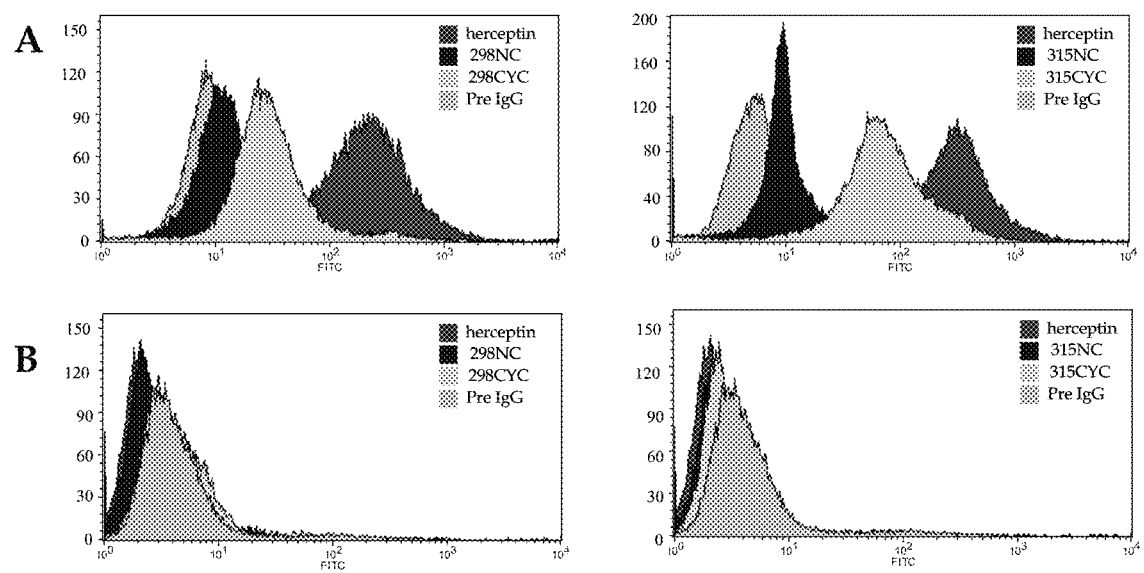
FIG. 23 shows the cross-reactivity of peptide antibodies to HER-2. The reactivity of purified antibodies from immunized rabbit sera was tested with (A) BT474 (HER-2high) and (B) MDA468 (HER-2low) breast cancer cell lines using flow cytometric analysis. Ab binding was detected with goat-anti rabbit FITC-conjugated abs. The x-axis represents fluorescent intensity, and the y-axis represents relative cell number. Each histogram contains an overlay of rabbit pre IgG, peptide antibodies, and herceptin, a human mAb that binds HER-2.
Figure 24:
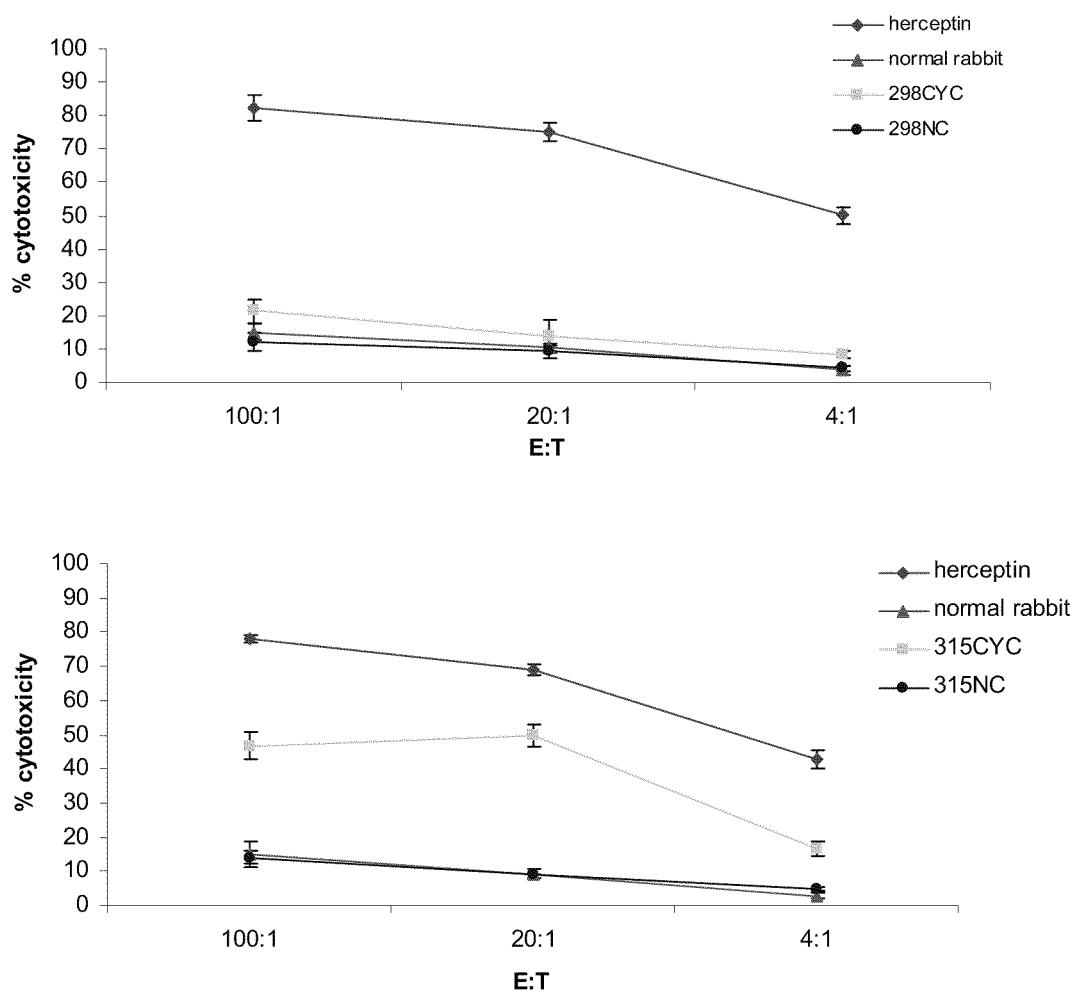
FIG. 24 shows that peptide antibodies induce ADCC (antibody dependent cell-mediated cytotoxicity) against BT474 breast cancer cells in vitro. Target cell line BT474 was incubated with peptide antibodies from rabbits, normal rabbit IgG, or herceptin in the presence of $Na^{51}CrO_4$ for one hour. After three washings target cells were cultured with human PBMC effector cells to give an effector:target (E:T) ratio of 100:1, 20:1, and 4:1 for four hours at 37° C. Supernatant was subsequently harvested and radioactivity determined using a γ-counter. Cytotoxicity was calculated from the formula 100× (A−B)/(C−B) where A represents 51Cr (cpm) from test supernatant, B represents 51Cr (cpm) from target alone in culture (spontaneous), and C represents maximum 51Cr release from cells lysed with 5% SDS. Results represent the average (±SEM) of triplicate samples.
Figure 25:
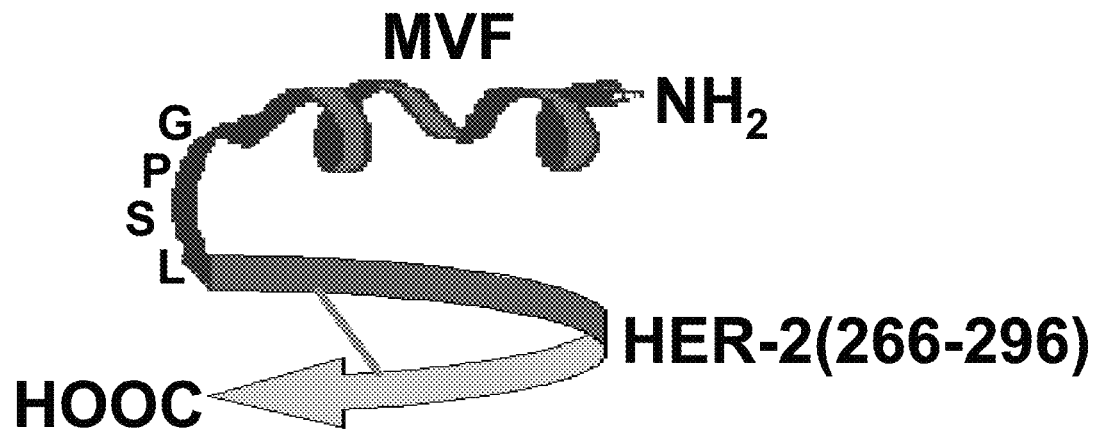
FIG. 25 shows a schematic representation of the chimeric peptide vaccine construct consisting of the 'promiscuous' TH-cell epitope derived from the measles virus fusion protein (MVF, residues 288-302) co-linearly synthesized with the B-cell epitope (HER-2(266-296)) via a flexible linker (GPSL) (SEQ ID NO: 18), allowing independent folding of MVF and the B-cell epitope.
Figure 26:
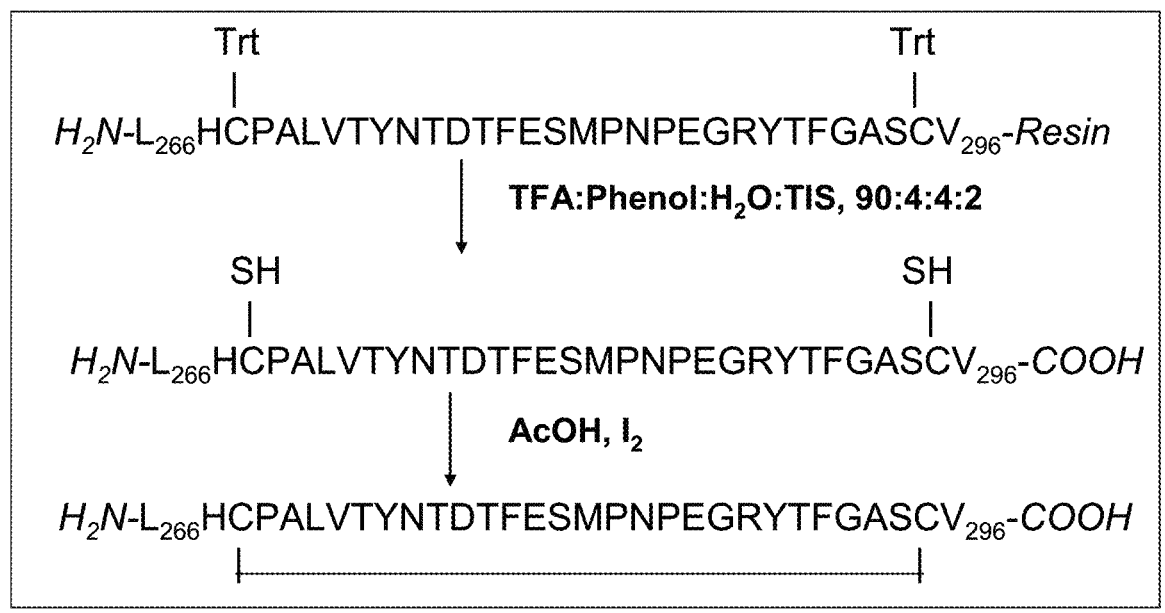
FIG. 26 shows solid-phase peptide synthesis was performed using preloaded Fmoc-Val-CLEAR Acid resin. Peptides were cleaved using Reagent B (TFA:Phenol:$H_2O$:TIS, 90:4:4:1) and crude peptide purified by RP-HPLC. Iodine oxidation was used to form the naturally occurring disulfide bond between Cys268 and Cys295 (SEQ ID NO: 28)
Figure 27:
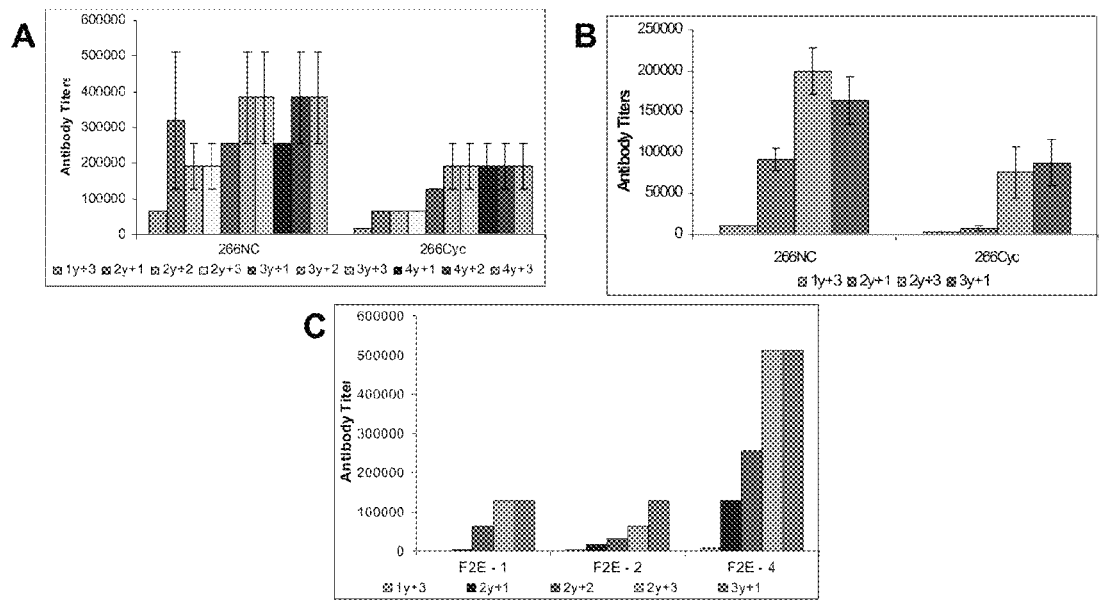
FIG. 27 shows A) Antibody titers of NZW rabbits mice immunized with MVF-HER-2(266-296) non-cyclized and cyclized peptides. B) Antibody titers of wild-type FVB/n mice immunized with MVF-HER-2(266-296) non-cyclized and cyclized peptides. C) Antibody titers of Neu overexpressing FVB/n mice immunized with MVF-HER-2(266-296). Serum was collected weekly and titers determined by direct ELISA.
Figure 28:
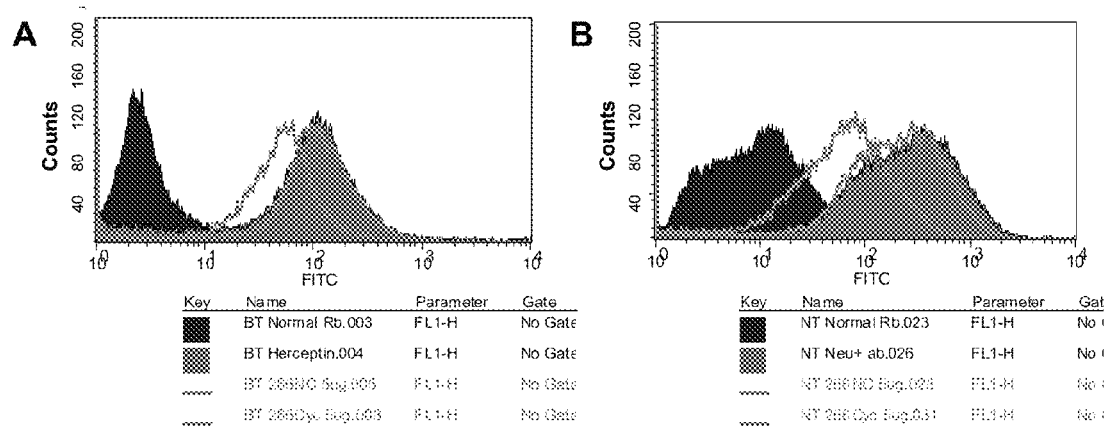
FIG. 28 shows the purified MVF-HER-2(266-296) cyclized and non-cyclized antibodies tested for their ability to bind to the native protein on human BT474 HER-2 overexpressing tumor cells (A) and mouse NT2.5 neu-overexpressing tumor cells (B). Both antibodies were shifted compared to the normal IgG isotype control and had similar binding compared to the positive controls (Herceptin for BT474 and anti-c-ErbB2/c-Neu (Ab-4) for NT2.5)
Figure 29:
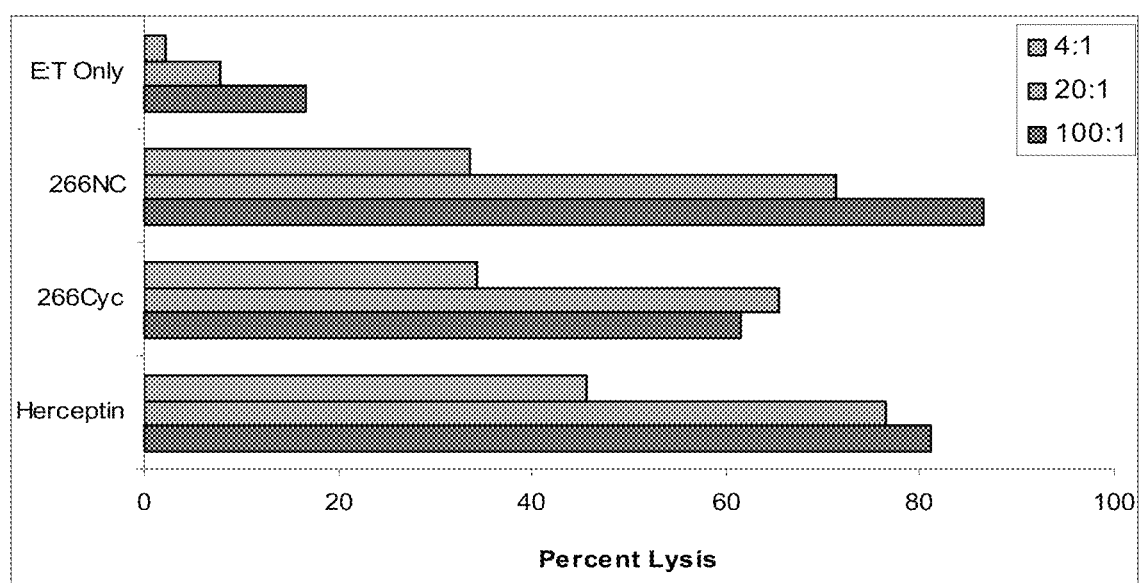
FIG. 29 shows antibody-dependent cell-mediated cytotoxicity determined by incubating BT474 cells with purified MVF-HER-2(266-296) cyclized and non-cyclized antibodies and 51Cr, then exposing the antibody-bound cells to human PBMCs, which perform immunologic lysis on the BT474 cells.
Figure 30:
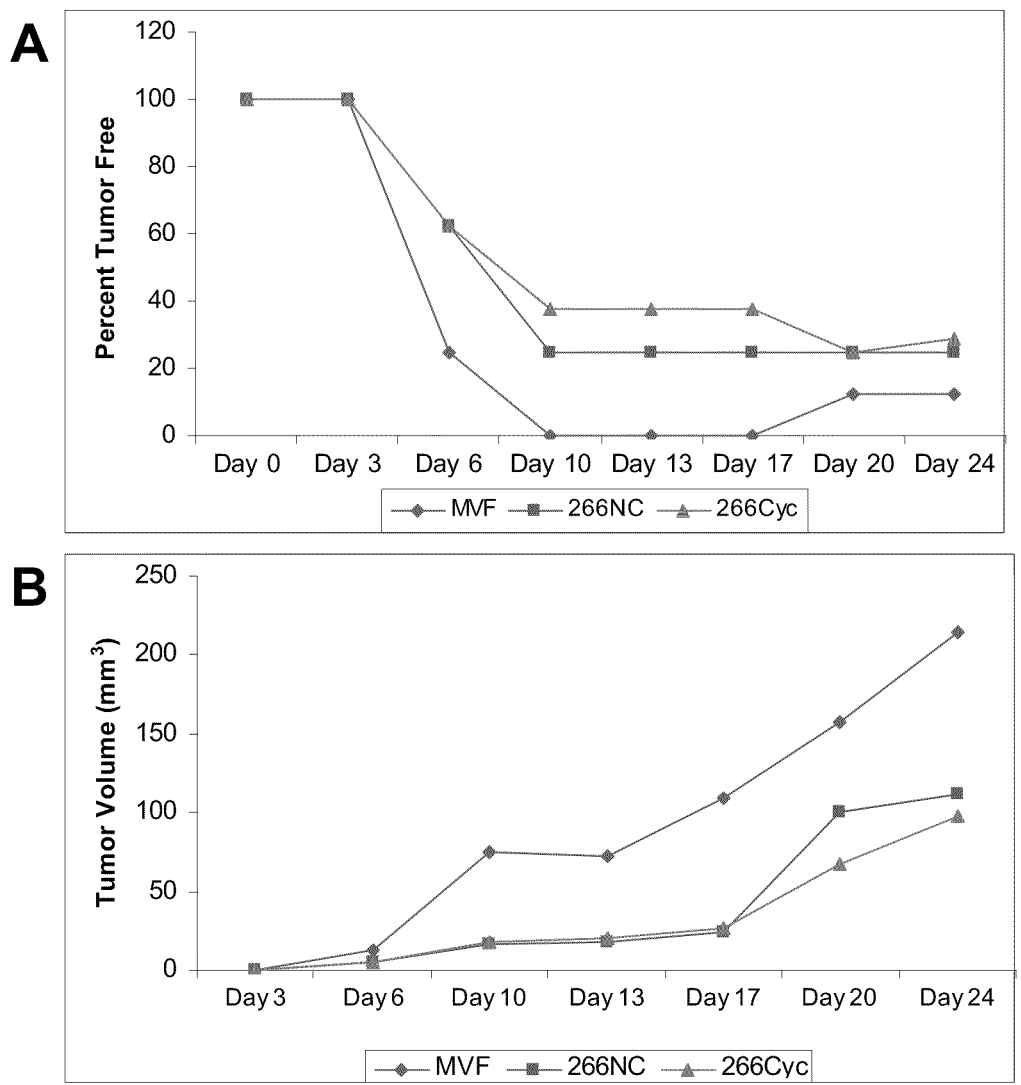
FIG. 30 shows wild-type FVB/n mice from FIG. 3B subcutaneously challenged with 3×106 NT2.5 cells and tumor growth monitored for 24 days. MVF-HER-2(266-296) cyclized- and non-cyclized-treated mice had delayed tumor development (A) and growth (B) as compared to the MVF immunized mice only.

Whether the conformational peptides from trastuzumab binding sites could recognize herceptin by ELISA was tested. As shown in FIG. 4, various peptides in the binding region of 563-626 bound trastuzumab. Maximum binding occurred with cyclized epitope 563-598 which possesses the 3 disulfide pairings. This result is in contrast with the FACS binding of antibodies to HER-2 due to glycosylation.

Example 5

Cross-Reactivity of Peptide Antibodies with HER-2 Protein

To determine if antibodies elicited by the Herceptin-peptide epitopes show differences in their ability to recognize the HER-2 receptor, the binding of FVB/n purified antibodies to the HER-2 over-expressing human breast cancer cell line BT474 was tested. FIG. 5 C, D shows that both the 597-626 and the 613-626 construct are shifted relative to normal mouse antibodies. However the 563-598 and the 585-598 constructs showed little shift compared to normal mouse antibodies (FIG. 5 A, B). The 563-598 contains two of the three contacts that HER-2 makes with trastuzumab. The 597-626 epitope, which contains the last contact point with trastuzumab consist of 11 amino acids that recognize the native protein (FIG. 5C). The shorter version of this sequence 613-

626 also recognizes the native protein in a similar manner (FIG. 5D). A plausible explanation for the lack of recognition of epitope 563-598 and 585-598 is that there is a potential glycosylation site at residues 571-573 (NGS) with the large bulky sugar moiety interfering sterically and prevents binding of that epitope.

Example 6

Tumor Challenge

To better understand the potential clinical benefit associated with introducing conformational constraints into B-cell epitope vaccines, both FVB/n and neu-N transgenic mice were challenged with the tumor cell line NT2.5 derived from a spontaneous mammary tumor isolated from a neu-N transgenic mouse. As a consequence of neu over-expression these mice develop spontaneous mammary adenocarcinomas in a manner similar to that observed in human breast cancer patients, and are therefore a suitable model for human breast cancer studies. Groups of FVB/n mice were challenged with $5\times10^6$ NT2.5 cells s.c. (lower abdomen) two weeks after final immunization. Tumor measurements were taken twice weekly until day 55. Tumor volumes were calculated by the formula (long measurement×short measurement$^2$)/2. Note that after day 30 the tumors in FVB/n mice begin to regress, indicative of rejection of the tumor. With subsequent tumor studies using FVB/n mice, tumors were measured to day 30. Mice immunized with the 563-598 NC and SS constructs had mean tumor volumes at day 30 of 166.517 and 173.7292 $mm^3$ respectively while unimmunized mice had a mean tumor volume of 346.6563 $mm^3$ (data not shown. By day 33 mice immunized with the 613-626 and 585-598CYC showed a reduction in tumor volume compared to both unimmunized and MVF immunized mice. While there appears to be some moderate success in terms of reduction in tumor burden of mice immunized with the trastuzumab B-cell epitopes, nearly all mice developed tumors.

Example 7

Design and Evaluation of Novel Pertuzumab-Binding Conformational B-Cell Epitopes The 3 peptide sequence listed in the Table 2 were designed to further delineate the minimal sequence to elicit an antibody similar to the pertuzumab binding site. These complex conformational peptide epitopes have been synthesized, successfully purified, and cyclized with the correct disulfide pairings. Epitope 266-296 (SH bond between Cys268-Cys295, Epitope 298-333 (SH bond between Cys 299-Cys311, and Epitope 315-333 (SH bond Cys 315-Cys 331) should allow us to delineate the minimal pertuzumab binding epitope.

| Designation | Peptide | Sequence |
| --- | --- | --- |
| MVF 266 CYC | 266-296 | H2N-*KLLSLIKGVIVHRLEGVE*-GPSL-LHCPALVTYNTDTFESMPNPEGRYTFGASCV-COOH |
| MVF 298 CYC | 298-333 | H2N-*KLLSLIKGVIVHRLEGVE*-GPSL-ACPYNYLSTDVGSCTLVCPLHNQEVTAEDGTQRCEK-COOH |

-continued

| Designation | | Peptide Sequence |
|---|---|---|
| MVF 315 CYC | 315-333 | H2N-*KLLSLIKGVIVHRLEGVE*-GPSL-<br>$^C$PLHNQEVTAEDGTQRCEK-COOH |

Table 2 shows engineered HER-2 B chimeric peptides (SEQ ID NOs: 23-25 are disclosed respectively in order of appearance).

Additional results are shown in FIGS. 6-30.

It will be obvious to those skilled in the art that various changes may be made without departing from the scope of the invention, which is not to be considered limited to what is described in the specification.

What is claimed is:

1. An immunogenic composition comprising a chimeric peptide, wherein the chimeric peptide comprises a HER-2 B epitope, a T helper (Th) epitope, and a linker joining the HER-2 B epitope to the Th epitope, wherein:

the HER-2 B epitope consists of the sequence selected from the group consisting of:

```
                                           SEQ ID NO: 2
CHPECQPQNGSVTCFGPEADQCVACAHYKDPPFCVA,;

SEQ ID NO: 3
VACAHYKDPPFCVA,;

SEQ ID NO: 4
VARCPSGVKPDLSYMPIWKFPDEEGACQPL,;

SEQ ID NO: 5
IWKFPDEEGACQPL,;

SEQ ID NO: 7
ACPYNYLSTDVGSCTLVCPLHNQEVTAEDGTQRCEK,;

SEQ ID NO: 8
CPLHNQEVTAEDGTQRCEK,;
and

SEQ ID NO: 9
CPINCTHSCVDLDDKGCPAEQRAS,;
``` the Th epitope comprises the sequence selected from the group consisting of:

```
KLLSLIKGVIVHRLEGVE,;          SEQ ID NO: 10
NSVDDALINSTIYSYFPSV,;         SEQ ID NO: 11
PGINGKAIHLVNNQSSE,;           SEQ ID NO: 12
QYIKANSKFIGITEL,;             SEQ ID NO: 13
FNNFTVSFWLRVPKVSASHLE,;       SEQ ID NO: 14
LSEIKGVIVHRLEGV,;             SEQ ID NO: 15
FFLLTRILTIPQSLN,;             SEQ ID NO: 16
and
TCGVGVRVRSRVNAANKKPE,;        SEQ ID NO: 17
``` the linker comprises a sequence that is from 1 to 15 amino acids in length.

2. The composition according to claim 1 wherein at least one of the HER-2 B epitope, the Th epitope, or the linker is in retro-inverso form.

3. The composition according to claim 1 wherein the linker comprises 2 to 15 amino acids.

4. The composition according to claim 1 wherein the linker comprises GPSL, SEQ ID NO: 18.

5. The composition according to claim 1 wherein the Th epitope has the sequence of KLLSLIKGVIVHRLEGVE, SEQ ID NO: 10.

6. The composition according to claim 1 wherein the Th epitope has the sequence of NSVDDALINSTIYSYFPSV, SEQ ID NO: 11.

7. The composition according to claim 1 wherein the Th epitope has the sequence of PGINGKAIHLVNNQSSE, SEQ ID NO: 12.

8. The composition according to claim 1 wherein the Th epitope has the sequence of QYIKANSKFIGITEL, SEQ ID NO: 13.

9. The composition according to claim 1 wherein the Th epitope has the sequence of FNNFTVSFWLRVP-KVSASHLE, SEQ ID NO: 14.

10. The composition according to claim 1 wherein the Th epitope has the sequence of LSEIKGVIVHRLEGV, SEQ ID NO: 15.

11. The composition according to claim 1 wherein the Th epitope has the sequence of FFLLTRILTIPQSLN, SEQ ID NO: 16.

12. The composition according to claim 1 wherein the Th epitope has the sequence of TCGVGVRVRSRVNAANKKPE, SEQ ID NO: 17.

13. The composition according to claim 1 further comprising a second HER-2 B epitope comprising the sequence selected from the group consisting of:
CHPECQPQNGSVTCFGPEADQC-VACAHYKDPPFCVA, SEQ ID NO: 2;
VACAHYKDPPFCVA, SEQ ID NO: 3;
VARCPSGVKPDLSYMPIWKFPDEEGACQPL, SEQ ID NO: 4;
IWKFPDEEGACQPL, SEQ ID NO: 5;
LHCPALVTYNTDTFESMPNPEGRYTFGASCV, SEQ ID NO: 6;
ACPYNYLSTDVGSCTLVCPLHNQEV-TAEDGTQRCEK, SEQ ID NO: 7;
CPLHNQEVTAEDGTQRCEK, SEQ ID NO: 8; and
CPINCTHSCVDLDDKGCPAEQRAS, SEQ ID NO: 9.

14. The composition according to claim 13 further comprising a second linker joining the first HER-2 B epitope to the second HER-2 B epitope.

15. The composition according to claim 14 wherein the second linker comprises a sequence that is from 1 to 15 amino acids in length.

16. The composition according to claim 15 wherein the second linker comprises GPSL, SEQ ID NO: 18.

17. A method of stimulating an immune response in a subject comprising administering to said subject the composition of claim 1.

18. A method of treating HER-2 expressing cancer in a subject comprising administering to said subject the composition of claim 1.

19. The method according to claim 18 wherein the subject is a human and has one of the following cancers or a predisposition to one of the following cancers: breast cancer; ovarian cancer; lung cancer; prostate cancer; and colon cancer.

20. The method according to claim 19 wherein the cancer is breast cancer.

* * * * *

UNITED STATES PATENT AND TRADEMARK OFFICE
CERTIFICATE OF CORRECTION

PATENT NO. : 8,470,333 B2  
APPLICATION NO. : 12/697578  
DATED : June 25, 2013  
INVENTOR(S) : Pravin Kaumaya Page 1 of 1

It is certified that error appears in the above-identified patent and that said Letters Patent is hereby corrected as shown below:

In the Specification

Column 1, Lines 16-19, cancel the text beginning with "The work described" to and ending "certain rights in this invention." and insert the following language:
--This invention was made with government support under CA084356 awarded by the National Institutes of Health. The government has certain rights in the invention.--

Signed and Sealed this  
Fourth Day of December, 2018

Andrei Iancu  
*Director of the United States Patent and Trademark Office*

UNITED STATES PATENT AND TRADEMARK OFFICE
CERTIFICATE OF CORRECTION

| | | |
|---|---|---|
| PATENT NO. | : 8,470,333 B2 | Page 1 of 1 |
| APPLICATION NO. | : 12/697578 | |
| DATED | : June 25, 2013 | |
| INVENTOR(S) | : Pravin Kaumaya | |

It is certified that error appears in the above-identified patent and that said Letters Patent is hereby corrected as shown below:

In the Specification

Column 1, Lines 16-19 replace the Government Support Clause with:
--This invention was made with government support under grant number CA084356 awarded by the National Institutes of Health. The government has certain rights in the invention.--

This certificate supersedes the Certificate of Correction issued December 4, 2018.

Signed and Sealed this
Sixth Day of October, 2020

Andrei Iancu
*Director of the United States Patent and Trademark Office*

SEQUENCE LISTING

<160> NUMBER OF SEQ ID NOS: 30

<210> SEQ ID NO 1
<211> LENGTH: 1255
<212> TYPE: PRT
<213> ORGANISM: Homo sapiens

<400> SEQUENCE: 1

```
Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300
```

```
Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
        340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Val Ser
                645                 650                 655

Ala Val Val Gly Ile Leu Leu Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735
```

```
Gly Ile Trp Ile Pro Asp Gly Glu Asn Val Lys Ile Pro Val Ala Ile
                740                 745                 750
Lys Val Leu Arg Glu Asn Thr Ser Pro Lys Ala Asn Lys Glu Ile Leu
            755                 760                 765
Asp Glu Ala Tyr Val Met Ala Gly Val Gly Ser Pro Tyr Val Ser Arg
        770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
            820                 825                 830
Met Ser Tyr Leu Glu Asp Val Arg Leu Val His Arg Asp Leu Ala Ala
        835                 840                 845
Arg Asn Val Leu Val Lys Ser Pro Asn His Val Lys Ile Thr Asp Phe
850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                885                 890                 895
Arg Arg Phe Thr His Gln Ser Asp Val Trp Ser Tyr Gly Val Thr Val
            900                 905                 910
Trp Glu Leu Met Thr Phe Gly Ala Lys Pro Tyr Asp Gly Ile Pro Ala
        915                 920                 925
Arg Glu Ile Pro Asp Leu Leu Glu Lys Gly Glu Arg Leu Pro Gln Pro
    930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                965                 970                 975
Ser Arg Met Ala Arg Asp Pro Gln Arg Phe Val Val Ile Gln Asn Glu
            980                 985                 990
Asp Leu Gly Pro Ala Ser Pro Leu Asp Ser Thr Phe Tyr Arg Ser Leu
        995                 1000                1005
Leu Glu Asp Asp Asp Met Gly Asp Leu Val Asp Ala Glu Glu Tyr Leu
    1010                1015                1020
Val Pro Gln Gln Gly Phe Phe Cys Pro Asp Pro Ala Pro Gly Ala Gly
1025                1030                1035                1040
Gly Met Val His His Arg His Arg Ser Ser Ser Thr Arg Ser Gly Gly
                1045                1050                1055
Gly Asp Leu Thr Leu Gly Leu Glu Pro Ser Glu Glu Ala Pro Arg
            1060                1065                1070
Ser Pro Leu Ala Pro Ser Glu Gly Ala Gly Ser Asp Val Phe Asp Gly
        1075                1080                1085
Asp Leu Gly Met Gly Ala Ala Lys Gly Leu Gln Ser Leu Pro Thr His
    1090                1095                1100
Asp Pro Ser Pro Leu Gln Arg Tyr Ser Glu Asp Pro Thr Val Pro Leu
1105                1110                1115                1120
Pro Ser Glu Thr Asp Gly Tyr Val Ala Pro Leu Thr Cys Ser Pro Gln
                1125                1130                1135
Pro Glu Tyr Val Asn Gln Pro Asp Val Arg Pro Gln Pro Pro Ser Pro
            1140                1145                1150
Arg Glu Gly Pro Leu Pro Ala Ala Arg Pro Ala Gly Ala Thr Leu Glu
```

-continued

```
                            1155                1160                1165

Arg Ala Lys Thr Leu Ser Pro Gly Lys Asn Gly Val Val Lys Asp Val
        1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
            1205                1210                1215

Phe Asp Asn Leu Tyr Tyr Trp Asp Gln Asp Pro Pro Glu Arg Gly Ala
                1220                1225                1230

Pro Pro Ser Thr Phe Lys Gly Thr Pro Thr Ala Glu Asn Pro Glu Tyr
        1235                1240                1245

Leu Gly Leu Asp Val Pro Val
    1250                1255

<210> SEQ ID NO 2
<211> LENGTH: 36
<212> TYPE: PRT
<213> ORGANISM: Homo sapiens

<400> SEQUENCE: 2

Cys His Pro Glu Cys Gln Pro Gln Asn Gly Ser Val Thr Cys Phe Gly
1               5                   10                  15

Pro Glu Ala Asp Gln Cys Val Ala Cys Ala His Tyr Lys Asp Pro Pro
            20                  25                  30

Phe Cys Val Ala
        35

<210> SEQ ID NO 3
<211> LENGTH: 14
<212> TYPE: PRT
<213> ORGANISM: Homo sapiens

<400> SEQUENCE: 3

Val Ala Cys Ala His Tyr Lys Asp Pro Pro Phe Cys Val Ala
1               5                   10

<210> SEQ ID NO 4
<211> LENGTH: 30
<212> TYPE: PRT
<213> ORGANISM: Homo sapiens

<400> SEQUENCE: 4

Val Ala Arg Cys Pro Ser Gly Val Lys Pro Asp Leu Ser Tyr Met Pro
1               5                   10                  15

Ile Trp Lys Phe Pro Asp Glu Glu Gly Ala Cys Gln Pro Leu
            20                  25                  30

<210> SEQ ID NO 5
<211> LENGTH: 14
<212> TYPE: PRT
<213> ORGANISM: Homo sapiens

<400> SEQUENCE: 5

Ile Trp Lys Phe Pro Asp Glu Glu Gly Ala Cys Gln Pro Leu
1               5                   10

<210> SEQ ID NO 6
<211> LENGTH: 31
<212> TYPE: PRT
<213> ORGANISM: Homo sapiens

<400> SEQUENCE: 6
```

```
Leu His Cys Pro Ala Leu Val Thr Tyr Asn Thr Asp Thr Phe Glu Ser
 1               5                  10                  15

Met Pro Asn Pro Glu Gly Arg Tyr Thr Phe Gly Ala Ser Cys Val
                20                  25                  30

<210> SEQ ID NO 7
<211> LENGTH: 36
<212> TYPE: PRT
<213> ORGANISM: Homo sapiens

<400> SEQUENCE: 7

Ala Cys Pro Tyr Asn Tyr Leu Ser Thr Asp Val Gly Ser Cys Thr Leu
 1               5                  10                  15

Val Cys Pro Leu His Asn Gln Glu Val Thr Ala Glu Asp Gly Thr Gln
                20                  25                  30

Arg Cys Glu Lys
            35

<210> SEQ ID NO 8
<211> LENGTH: 19
<212> TYPE: PRT
<213> ORGANISM: Homo sapiens

<400> SEQUENCE: 8

Cys Pro Leu His Asn Gln Glu Val Thr Ala Glu Asp Gly Thr Gln Arg
 1               5                  10                  15

Cys Glu Lys

<210> SEQ ID NO 9
<211> LENGTH: 24
<212> TYPE: PRT
<213> ORGANISM: Homo sapiens

<400> SEQUENCE: 9

Cys Pro Ile Asn Cys Thr His Ser Cys Val Asp Leu Asp Asp Lys Gly
 1               5                  10                  15

Cys Pro Ala Glu Gln Arg Ala Ser
                20

<210> SEQ ID NO 10
<211> LENGTH: 18
<212> TYPE: PRT
<213> ORGANISM: Homo sapiens

<400> SEQUENCE: 10

Lys Leu Leu Ser Leu Ile Lys Gly Val Ile Val His Arg Leu Glu Gly
 1               5                  10                  15

Val Glu

<210> SEQ ID NO 11
<211> LENGTH: 19
<212> TYPE: PRT
<213> ORGANISM: Homo sapiens

<400> SEQUENCE: 11

Asn Ser Val Asp Asp Ala Leu Ile Asn Ser Thr Ile Tyr Ser Tyr Phe
 1               5                  10                  15

Pro Ser Val

<210> SEQ ID NO 12
<211> LENGTH: 17
```

```
<212> TYPE: PRT
<213> ORGANISM: Homo sapiens

<400> SEQUENCE: 12

Pro Gly Ile Asn Gly Lys Ala Ile His Leu Val Asn Asn Gln Ser Ser
 1               5                  10                  15

Glu

<210> SEQ ID NO 13
<211> LENGTH: 15
<212> TYPE: PRT
<213> ORGANISM: Homo sapiens

<400> SEQUENCE: 13

Gln Tyr Ile Lys Ala Asn Ser Lys Phe Ile Gly Ile Thr Glu Leu
 1               5                  10                  15

<210> SEQ ID NO 14
<211> LENGTH: 21
<212> TYPE: PRT
<213> ORGANISM: Homo sapiens

<400> SEQUENCE: 14

Phe Asn Asn Phe Thr Val Ser Phe Trp Leu Arg Val Pro Lys Val Ser
 1               5                  10                  15

Ala Ser His Leu Glu
            20

<210> SEQ ID NO 15
<211> LENGTH: 15
<212> TYPE: PRT
<213> ORGANISM: Homo sapiens

<400> SEQUENCE: 15

Leu Ser Glu Ile Lys Gly Val Ile Val His Arg Leu Glu Gly Val
 1               5                  10                  15

<210> SEQ ID NO 16
<211> LENGTH: 15
<212> TYPE: PRT
<213> ORGANISM: Homo sapiens

<400> SEQUENCE: 16

Phe Phe Leu Leu Thr Arg Ile Leu Thr Ile Pro Gln Ser Leu Asn
 1               5                  10                  15

<210> SEQ ID NO 17
<211> LENGTH: 20
<212> TYPE: PRT
<213> ORGANISM: Homo sapiens

<400> SEQUENCE: 17

Thr Cys Gly Val Gly Val Arg Val Arg Ser Arg Val Asn Ala Ala Asn
 1               5                  10                  15

Lys Lys Pro Glu
            20

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide
```

```
<400> SEQUENCE: 18

Gly Pro Ser Leu
 1

<210> SEQ ID NO 19
<211> LENGTH: 58
<212> TYPE: PRT
<213> ORGANISM: Artificial Sequence
<220> FEATURE:
<223> OTHER INFORMATION: Description of Artificial Sequence: Synthetic
      chimeric peptide

<400> SEQUENCE: 19

Lys Leu Leu Ser Leu Ile Lys Gly Val Ile Val His Arg Leu Glu Gly
 1               5                  10                  15

Val Glu Gly Pro Ser Leu Cys His Pro Glu Cys Gln Pro Gln Asn Gly
            20                  25                  30

Ser Val Thr Cys Phe Gly Pro Glu Ala Asp Gln Cys Val Ala Cys Ala
        35                  40                  45

His Tyr Lys Asp Pro Pro Phe Cys Val Ala
    50                  55

<210> SEQ ID NO 20
<211> LENGTH: 36
<212> TYPE: PRT
<213> ORGANISM: Artificial Sequence
<220> FEATURE:
<223> OTHER INFORMATION: Description of Artificial Sequence: Synthetic
      chimeric peptide

<400> SEQUENCE: 20

Lys Leu Leu Ser Leu Ile Lys Gly Val Ile Val His Arg Leu Glu Gly
 1               5                  10                  15

Val Glu Gly Pro Ser Leu Val Ala Cys Ala His Tyr Lys Asp Pro Pro
            20                  25                  30

Phe Cys Val Ala
        35

<210> SEQ ID NO 21
<211> LENGTH: 52
<212> TYPE: PRT
<213> ORGANISM: Artificial Sequence
<220> FEATURE:
<223> OTHER INFORMATION: Description of Artificial Sequence: Synthetic
      chimeric peptide

<400> SEQUENCE: 21

Lys Leu Leu Ser Leu Ile Lys Gly Val Ile Val His Arg Leu Glu Gly
 1               5                  10                  15

Val Glu Gly Pro Ser Leu Val Ala Arg Cys Pro Ser Gly Val Lys Pro
            20                  25                  30

Asp Leu Ser Tyr Met Pro Ile Trp Lys Phe Pro Asp Glu Glu Gly Ala
        35                  40                  45

Cys Gln Pro Leu
    50

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Synthetic
      chimeric peptide
```

```
-continued

<400> SEQUENCE: 22

Lys Leu Leu Ser Leu Ile Lys Gly Val Ile Val His Arg Leu Glu Gly
 1               5                  10                  15

Val Glu Gly Pro Ser Leu Ile Trp Lys Phe Pro Asp Glu Glu Gly Ala
            20                  25                  30

Cys Gln Pro Leu
        35

<210> SEQ ID NO 23
<211> LENGTH: 53
<212> TYPE: PRT
<213> ORGANISM: Artificial Sequence
<220> FEATURE:
<223> OTHER INFORMATION: Description of Artificial Sequence: Synthetic
      chimeric peptide

<400> SEQUENCE: 23

Lys Leu Leu Ser Leu Ile Lys Gly Val Ile Val His Arg Leu Glu Gly
 1               5                  10                  15

Val Glu Gly Pro Ser Leu Leu His Cys Pro Ala Leu Val Thr Tyr Asn
            20                  25                  30

Thr Asp Thr Phe Glu Ser Met Pro Asn Pro Gly Arg Tyr Thr Phe
        35                  40                  45

Gly Ala Ser Cys Val
        50

<210> SEQ ID NO 24
<211> LENGTH: 58
<212> TYPE: PRT
<213> ORGANISM: Artificial Sequence
<220> FEATURE:
<223> OTHER INFORMATION: Description of Artificial Sequence: Synthetic
      chimeric peptide

<400> SEQUENCE: 24

Lys Leu Leu Ser Leu Ile Lys Gly Val Ile Val His Arg Leu Glu Gly
 1               5                  10                  15

Val Glu Gly Pro Ser Leu Ala Cys Pro Tyr Asn Tyr Leu Ser Thr Asp
            20                  25                  30

Val Gly Ser Cys Thr Leu Val Cys Pro Leu His Asn Gln Glu Val Thr
        35                  40                  45

Ala Glu Asp Gly Thr Gln Arg Cys Glu Lys
        50                  55

<210> SEQ ID NO 25
<211> LENGTH: 41
<212> TYPE: PRT
<213> ORGANISM: Artificial Sequence
<220> FEATURE:
<223> OTHER INFORMATION: Description of Artificial Sequence: Synthetic
      chimeric peptide

<400> SEQUENCE: 25

Lys Leu Leu Ser Leu Ile Lys Gly Val Ile Val His Arg Leu Glu Gly
 1               5                  10                  15

Val Glu Gly Pro Ser Leu Cys Pro Leu His Asn Gln Glu Val Thr Ala
            20                  25                  30

Glu Asp Gly Thr Gln Arg Cys Glu Lys
        35                  40

<210> SEQ ID NO 26
<211> LENGTH: 46
```

-continued

```
<212> TYPE: PRT
<213> ORGANISM: Artificial Sequence
<220> FEATURE:
<223> OTHER INFORMATION: Description of Artificial Sequence: Synthetic
      chimeric peptide

<400> SEQUENCE: 26

Lys Leu Leu Ser Leu Ile Lys Gly Val Ile His Arg Leu Glu Gly
 1               5                  10                  15

Val Glu Gly Pro Ser Leu Cys Pro Ile Asn Cys Thr His Ser Cys Val
                20                  25                  30

Asp Leu Asp Asp Lys Gly Cys Pro Ala Glu Gln Arg Ala Ser
            35                  40                  45

<210> SEQ ID NO 27
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

His Pro Glu Cys Gln Pro Gln Asn Gly Ser Val Thr Cys Phe Gly Pro
 1               5                  10                  15

Glu Ala Asp Gln Cys Val Ala Cys Ala His Tyr Lys Asp Pro Pro Phe
                20                  25                  30

Cys Val Ala
        35

<210> SEQ ID NO 28
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

His Cys Pro Ala Leu Val Thr Tyr Asn Thr Asp Thr Phe Glu Ser Met
 1               5                  10                  15

Pro Asn Pro Glu Gly Arg Tyr Thr Phe Gly Ala Ser Cys Val
                20                  25                  30

<210> SEQ ID NO 29
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys His Pro Glu Cys Gln Pro Gln Asn Gly Ser Val Thr Cys Phe Gly
 1               5                  10                  15

Pro Glu Ala Asp Gln Cys Val Ala Cys Ala His Tyr Lys Asp Pro Pro
                20                  25                  30

Phe Cys Val Ala
        35

<210> SEQ ID NO 30
<211> LENGTH: 35
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 30

Cys Pro Tyr Asn Tyr Leu Ser Thr Asp Val Gly Ser Cys Thr Leu Val
 1               5                  10                  15

Cys Pro Leu His Asn Gln Glu Val Thr Ala Glu Asp Gly Thr Gln Arg
                20                  25                  30

Cys Glu Lys
        35
```